(12) United States Patent
Aebi et al.

(10) Patent No.: US 9,187,429 B2
(45) Date of Patent: Nov. 17, 2015

(54) PHENYL-TETRAHYDROISOQUINOLINE DERIVATIVES

(71) Applicant: Hoffmann-La Roche Inc., Nutley, NJ (US)

(72) Inventors: Johannes Aebi, Binningen (CH); Kurt Amrein, Itingen (CH); Benoit Hornsperger, Altkirch (FR); Bernd Kuhn, Reinach (CH); Yongfu Liu, Shanghai (CN); Hans P. Maerki, Basel (CH); Rainer E. Martin, Basel (CH); Alexander V. Mayweg, Shanghai (CN); Peter Mohr, Basel (CH); Xuefei Tan, Shanghai (CH)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 13/864,889

(22) Filed: Apr. 17, 2013

(65) Prior Publication Data

US 2013/0274287 A1    Oct. 17, 2013

Related U.S. Application Data

(63) Continuation of application No. PCT/CN2012/074170, filed on Apr. 17, 2012.

(51) Int. Cl.
| | |
|---|---|
| C07D 217/22 | (2006.01) |
| C07D 217/24 | (2006.01) |
| A61K 31/47 | (2006.01) |
| C07D 217/14 | (2006.01) |
| C07D 221/04 | (2006.01) |
| C07D 405/12 | (2006.01) |
| C07D 221/16 | (2006.01) |

(52) U.S. Cl.
CPC ............ *C07D 217/14* (2013.01); *C07D 217/22* (2013.01); *C07D 217/24* (2013.01); *C07D 221/04* (2013.01); *C07D 221/16* (2013.01); *C07D 405/12* (2013.01)

(58) Field of Classification Search
None
See application file for complete search history.

(56) References Cited

U.S. PATENT DOCUMENTS

| 5,480,883 A * | 1/1996 | Spada et al. ................ 514/249 |
| 2009/0221591 A1 * | 9/2009 | Hartmann et al. ............ 514/249 |

* cited by examiner

*Primary Examiner* — Zinna Northington Davis
(74) *Attorney, Agent, or Firm* — Robert C. Hall

(57) ABSTRACT

The invention provides novel compounds having the general formula (I)

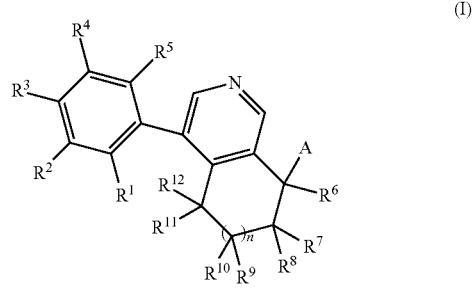

wherein $R^1$, $R^2$, $R^3$, $R^4$, $R^5$, $R^6$, $R^7$, $R^8$, $R^9$, $R^{10}$, $R^{11}$, $R^{12}$, A and n are as described herein, compositions including the compounds and methods of using the compounds.

42 Claims, No Drawings

PHENYL-TETRAHYDROISOQUINOLINE DERIVATIVES

CROSS REFERENCE TO RELATED APPLICATIONS

This application claims priority under 35 USC §120, or alternatively under 35 USC §119, to PCT/CN2012/074170 filed on Apr. 17, 2012, the disclosure of which is incorporated herein by reference.

FIELD OF THE INVENTION

The present invention relates to organic compounds useful for therapy or prophylaxis in a mammal, and in particular to aldosterone synthase (CYP11B2 or CYP11B1) inhibitors for the treatment or prophylaxis of chronic kidney disease, congestive heart failure, hypertension, primary aldosteronism and Cushing syndrome.

SUMMARY OF THE INVENTION

The present invention provides novel compounds of formula (I)

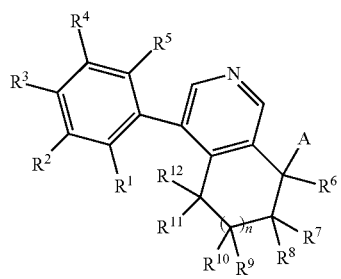

(I)

wherein
$R^1$, $R^2$, $R^3$ and $R^4$ are independently selected from H, halogen, cyano, nitro, alkoxycarbonyl, cycloalkoxycarbonyl, substituted aminocarbonyl, substituted aminosulfonyl, alkyl, haloalkyl, cycloalkyl, alkoxy, haloalkoxy and cycloalkoxy, wherein substituted aminocarbonyl and substituted aminosulfonyl are substituted on the nitrogen atom with one to two substituents independently selected from H, alkyl, cycloalkyl, hydroxyalkyl and alkoxyalkyl;
$R^5$ is H, halogen, alkyl or cycloalkyl;
$R^6$ is H, alkyl, haloalkyl, cycloalkyl, substituted aryl or substituted heteroaryl, wherein substituted aryl or substituted heteroaryl are substituted with $R^{19}$, $R^{20}$ and $R^{21}$;
$R^7$, $R^8$, $R^9$, $R^{10}$, $R^{11}$ and $R^{12}$ are independently selected from H, halogen, alkyl and haloalkyl;
A is —$(CR^{13}R^{14})_p$—$NR^{15}R^{16}$ or —$(CR^{13}R^{14})_p$—$OR^{16}$;
$R^{13}$ and $R^{14}$ are independently selected from H, alkyl, haloalkyl, cycloalkyl and halocycloalkyl;
$R^{15}$ is H, alkyl, haloalkyl, cycloalkyl, hydroxyalkyl, alkoxyalkyl or haloalkoxyalkyl;
$R^{16}$ is H, alkyl, haloalkyl, cycloalkyl, hydroxyalkyl, alkoxyalkyl, haloalkoxyalkyl, oxetanylalkyl, —$CH_2$—C(O)OH, —$CH_2$—C(O)$OR^{17}$, —$CH_2$—C(O)—$NR^{17}R^{18}$, —S(O)$R^{17}$, —S(O)$_2R^{17}$, —S(O)$_2OR^{17}$, —S(O)$_2NR^{17}R^{18}$, —C(O)$R^{17}$, —C(O)$OR^{17}$ or —C(O)$NR^{17}R^{18}$;

$R^{17}$ is alkyl, hydroxyalkyl, haloalkyl, cycloalkyl, alkylcycloalkyl, alkylcycloalkylalkyl, cycloalkylalkyl, cycloalkoxyalkyl, cycloalkylalkoxyalkyl, alkoxyalkyl, haloalkoxyalkyl, alkoxyalkoxyalkyl or substituted heteroaryl, wherein substituted heteroaryl is substituted with $R^{22}$, $R^{23}$ and $R^{24}$;
$R^{18}$ is H, alkyl, haloalkyl, cycloalkyl, alkoxyalkyl, haloalkoxyalkyl or hydroxyalkyl;
$R^{19}$, $R^{20}$, $R^{21}$, $R^{22}$, $R^{23}$ and $R^{24}$ are independently selected from H, halogen, alkyl, haloalkyl, cycloalkyl, alkoxy and haloalkoxy;
n is zero, 1 or 2;
p is zero or 1;
or pharmaceutically acceptable salts or esters.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of chronic kidney disease, congestive heart failure, hypertension, primary aldosteronism and Cushing syndrome and the use of the said compounds, salts or esters for the production of medicaments for the treatment or prophylaxis of chronic kidney disease, congestive heart failure, hypertension, primary aldosteronism and Cushing syndrome.

BACKGROUND OF THE INVENTION

Hypertension affects about 20% of the adult population in developed countries. In persons 60 years and older, this percentage increases to above 60%. Hypertensive subjects display an increased risk of other physiological complications including stroke, myocardial infarction, atrial fibrillation, heart failure, peripheral vascular disease and renal impairment. The renin angiotensin aldosterone system is a pathway that has been linked to hypertension, volume and salt balance and more recently to contribute directly to end organ damage in advanced stages of heart failure or kidney disease. ACE inhibitors and angiotensin receptor blockers (ARBs) are successfully used to improve duration and quality of life of patients. These drugs are not yielding maximum protection. In a relatively large number of patients ACE and ARB's lead to so-called aldosterone breakthrough, a phenomenon where aldosterone levels, after a first initial decline, return to pathological levels. It has been demonstrated that the deleterious consequences of inappropriately increased aldosterone levels (in relation to salt intake/levels) can be minimized by aldosterone blockade with mineralocorticoid receptor antagonists. A direct inhibition of aldosterone synthesis is expected to provide even better protection as it will also reduce non-genomic effects of aldosterone as well.

The effects of aldosterone on Na/K transport lead to increased re-absorption of sodium and water and the secretion of potassium in the kidneys. Overall this results in increased blood volume and, therefore, increased blood pressure. Beyond its role in the regulation of renal sodium re-absorption aldosterone can exert deleterious effects on the kidney, the heart and the vascular system especially in a "high sodium" context. It has been shown that under such conditions aldosterone leads to increased oxidative stress which ultimately may contribute to organ damage. Infusion of aldosterone into renally compromised rats (either by high salt treatment or by unilaterally nephrectomy) induces a wide array of injuries to the kidney including glomerular expansion, podocyte injury, interstitial inflammation, mesangial cell proliferation and fibrosis reflected by proteinuria. More specifically aldosterone was shown to increase the expression of the adhesion molecule ICAM-1 in the kidney. ICAM-1 is critically involved in glomerular inflammation. Similarly, aldosterone was shown to increase the expression of inflammatory cytokines, such as interleukin IL-1b and IL-6, MCP-1 and osteopontin. On a cellular level it was demonstrated that in vascular fibroblasts aldosterone increased the expression of type I collagen mRNA, a mediator of fibrosis. Aldosterone also stimulates type IV collagen accumulation in rat mesangial cells and induces plasminogen activator inhibitor-1 (PAI-1) expression in smooth muscle cells. In summary aldosterone has emerged as a key hormone involved in renal damage. Aldosterone plays an equally important role in mediating cardiovascular risk.

There is ample preclinical evidence that MR-antagonists (spironolactone and eplerenone) improve blood pressure, cardiac and renal function in various pre-clinical models.

More recently preclinical studies highlight the important contribution of CYP11B2 to cardiovascular and renal morbidity and mortality. The CYP11B2 inhibitor FAD286 and the MR antagonist spironolactone were evaluated in a rat model of chronic kidney disease (high angiotensin II exposure; high salt and uni-nephrectomy). Angiotensin II and high salt treatment caused albuminuria, azotemia, renovascular hypertrophy, glomerular injury, increased PAI-1, and osteopontin mRNA expression, as well as tubulointerstitial fibrosis. Both drugs prevented these renal effects and attenuated cardiac and aortic medial hypertrophy. Following 4 weeks of treatment with FAD286, plasma aldosterone was reduced, whereas spironolactone increased aldosterone at 4 and 8 weeks of treatment. Similarly only spironolactone but not FAD286 enhanced angiotensin II and salt-stimulated PAI-1 mRNA expression in the aorta and the heart. In other studies the CYP11B2 inhibitor FAD286 improved blood pressure and cardiovascular function and structure in rats with experimental heart failure. In the same studies FAD286 was shown to improve kidney function and morphology.

Administration of an orally active CYP11B2 inhibitor, LCI699, to patients with primary aldosteronism, lead to the conclusion that it effectively inhibits CYP11B2 in patients with primary aldosteronism resulting in significantly lower circulating aldosterone levels and that it corrected the hypokalemia and mildly decreased blood pressure. The effects on the glucocorticoid axis were consistent with a poor selectivity of the compound and a latent inhibition of cortisol synthesis. Taken together these data support the concept that a CYP11B2 inhibitor can lower inappropriately high aldosterone levels. Achieving good selectivity against CYP11B1 is important to be free of undesired side effects on the HPA axis and will differentiate different CYP11B2 inhibitors.

DETAILED DESCRIPTION OF THE INVENTION

Herein we describe inhibitors of aldosterone synthase that have the potential to protect from organ/tissue damage caused by an absolute or relative excess of aldosterone.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy.

The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl, ethoxypropyl and isopropoxymethyl. Particular alkoxyalkyl group include methoxymethyl, methoxyethyl and isopropoxymethyl.

The term "alkoxycarbonyl" denotes a group of the formula —C(O)—R', wherein R' is an alkoxy group. Examples of alkoxycarbonyl groups include groups of the formula —C(O)—R', wherein R' is methoxy, ethoxy, n-propoxy, isopropoxy, n-butoxy, isobutoxy and tert-butoxy. Particular alkoxycarbonyl group is a group of the formula —C(O)—R', wherein R' is methoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, and. Particular alkyl groups include methyl, ethyl, propyl and isopropyl. More particular alkyl groups are methyl, ethyl and propyl.

The term "alkylcycloalkyl" denotes a cycloalkyl group wherein at least one of the hydrogen atoms of the cycloalkyl group is replaced by an alkyl group. Examples of alkylcycloalkyl include methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular alkylcycloalkyl groups include methyl-cyclopropyl and dimethyl-cyclopropyl.

The term "alkylcycloalkylalkyl" denotes an alkyl group wherein at least one of the hydrogen atoms of the alkyl group is replaced by an alkylcycloalkyl group. Examples of alkylcycloalkylalkyl include methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethyl-cyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "amino" denotes a —NH$_2$ group.
The term "aminocarbonyl" denotes a —C(O)NH$_2$ group.
The term "aminosulfonyl" denotes a —S(O)$_2$NH$_2$ group.
The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "carbonyl" denotes a —C(O)— group.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl group include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkoxycarbonyl" denotes a group of the formula —C(O)—R', wherein R' is a cycloalkoxy group. Examples of cycloalkoxycarbonyl groups include groups of the formula —C(O)—R', wherein R' is cyclopropoxy.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means consisting of two saturated carbocycles having two carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl. More articular monocyclic cycloalkyl group is cyclopropyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxyethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl and cyclopentylbutyl. Particular examples of cycloalkylalkyl groups are cyclopropylmethyl, cyclopropylbutyl and 2-cyclopropylbutyl.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy and 2,2-difluoroethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl. Particular haloalkoxyalkyl is 2,2-difluoroethoxyethyl.

The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl groups include fluorocyclopropyl, difluorocyclopropyl, fluorocyclobutyl and difluorocyclobutyl.

The term "halogen" and "halo" are used interchangeably herein and denote fluoro, chloro, bromo, or iodo. Particular halogens are chloro and fluoro.

In the case of $R^7$, $R^8$, $R^9$, $R^{10}$, $R^{11}$ and $R^{12}$, further particular halogen is fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyridazinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl groups include pyrrolyl, pyrazolyl, imidazolyl, triazolyl, benzoimidazolyl, indazolyl, indolyl, pyridinyl, isooxazolyl and oxazolyl.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxy-1-methylethyl, hydroxypropyl, hydroxymethylpropyl and dihydroxypropyl. Particular examples are hydroxymethyl and hydroxyethyl. Further particular example is hydroxyethyl.

The term "nitro" denotes a —NO$_2$ group.

The term "oxetanylalkyl" denotes an alkyl group wherein at least one of the hydrogen atoms of the alkyl group has been replaced an oxetanyl group. Particular oxetanylalkyl group is methyloxetanylmethyl. The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The abbreviation uM means microMolar and is equivalent to the symbol µM.

The compounds of formula (I) can contain several asymmetric centers and can be present in the form of optically pure enantiomers, mixtures of enantiomers such as, for example, racemates, optically pure diastereisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

The invention provides novel compounds of formula (I)

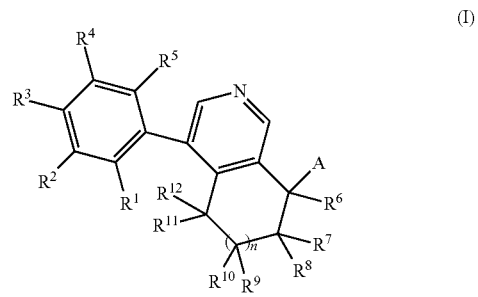

wherein
$R^1$, $R^2$, $R^3$ and $R^4$ are independently selected from H, halogen, cyano, nitro, alkoxycarbonyl, cycloalkoxycarbonyl, substituted aminocarbonyl, substituted aminosulfonyl, alkyl, haloalkyl, cycloalkyl, alkoxy, haloalkoxy and cycloalkoxy, wherein substituted aminocarbonyl and substituted aminosulfonyl are substituted on the nitrogen atom with one to two substituents independently selected from H, alkyl, cycloalkyl, hydroxyalkyl and alkoxyalkyl;
$R^5$ is H, halogen, alkyl or cycloalkyl;
$R^6$ is H, alkyl, haloalkyl, cycloalkyl, substituted aryl or substituted heteroaryl, wherein substituted aryl or substituted heteroaryl are substituted with $R^{19}$, $R^{20}$ and $R^{21}$;
$R^7$, $R^8$, $R^9$, $R^{10}$, $R^{11}$ and $R^{12}$ are independently selected from H, halogen, alkyl and haloalkyl;
A is $-(CR^{13}R^{14})_p-NR^{15}R^{16}$ or $-(CR^{13}R^{14})_p-OR^{16}$;
$R^{13}$ and $R^{14}$ are independently selected from H, alkyl, haloalkyl, cycloalkyl and halocycloalkyl;
$R^{15}$ is H, alkyl, haloalkyl, cycloalkyl, hydroxyalkyl, alkoxyalkyl or haloalkoxyalkyl;
$R^{16}$ is H, alkyl, haloalkyl, cycloalkyl, hydroxyalkyl, alkoxyalkyl, haloalkoxyalkyl, oxetanylalkyl, $-CH_2-C(O)OH$, $-CH_2-C(O)OR^{17}$, $-CH_2-C(O)-NR^{17}R^{18}$, $-S(O)R^{17}$, $-S(O)_2R^{17}$, $-S(O)_2OR^{17}$, $-S(O)_2NR^{17}R^{18}$, $-C(O)R^{17}$, $-C(O)OR^{17}$ or $-C(O)NR^{17}R^{18}$;
$R^{17}$ is alkyl, hydroxyalkyl, haloalkyl, cycloalkyl, alkylcycloalkyl, alkylcycloalkylalkyl, cycloalkylalkyl, cycloalkoxyalkyl, cycloalkylalkoxyalkyl, alkoxyalkyl, haloalkoxyalkyl, alkoxyalkoxyalkyl or substituted heteroaryl, wherein substituted heteroaryl is substituted with $R^{22}$, $R^{23}$ and $R^{24}$;
$R^{18}$ is H, alkyl, haloalkyl, cycloalkyl, alkoxyalkyl, haloalkoxyalkyl or hydroxyalkyl;
$R^{19}$, $R^{20}$, $R^{21}$, $R^{22}$, $R^{23}$ and $R^{24}$ are independently selected from H, halogen, alkyl, haloalkyl, cycloalkyl, alkoxy and haloalkoxy;
n is zero, 1 or 2;
p is zero or 1;
or pharmaceutically acceptable salts or esters.

Another embodiment of the present invention are compounds according to formula (I) as described herein, wherein $R^1$, $R^2$, $R^3$ and $R^4$ are independently selected from H, halogen, cyano, nitro, alkoxycarbonyl, cycloalkoxycarbonyl, substituted aminocarbonyl, substituted aminosulfonyl, alkyl, haloalkyl, cycloalkyl, alkoxy, haloalkoxy and cycloalkoxy, wherein substituted aminocarbonyl and substituted aminosulfonyl are substituted on the nitrogen atom with one to two substituents independently selected from H, alkyl, cycloalkyl, hydroxyalkyl and alkoxyalkyl;

$R^5$ is H, halogen, alkyl or cycloalkyl;

$R^6$ is H, alkyl, haloalkyl, cycloalkyl, substituted aryl or substituted heteroaryl, wherein substituted aryl or substituted heteroaryl are substituted with $R^{19}$, $R^{20}$ and $R^{21}$;

$R^7$, $R^8$, $R^9$, $R^{10}$, $R^{11}$ and $R^{12}$ are independently selected from H, halogen, alkyl and haloalkyl;

A is —$(CR^{13}R^{14})_p$—$NR^{15}R^{16}$ or —$(CR^{13}R^{14})_p$—$OR^{16}$;

$R^{13}$ and $R^{14}$ are independently selected from H, alkyl, haloalkyl, cycloalkyl and halocycloalkyl;

$R^{15}$ is H, alkyl, haloalkyl, cycloalkyl, hydroxyalkyl, alkoxyalkyl or haloalkoxyalkyl;

$R^{16}$ is H, alkyl, haloalkyl, cycloalkyl, hydroxyalkyl, alkoxyalkyl, haloalkoxyalkyl, —$S(O)R^{17}$, —$S(O)_2R^{17}$, —$S(O)_2OR^{17}$, —$S(O)_2NR^{17}R^{18}$, —$C(O)R^{17}$, —$C(O)OR^{17}$ or —$C(O)NR^{17}R^{18}$;

$R^{17}$ is alkyl, hydroxyalkyl, haloalkyl, cycloalkyl, alkylcycloalkyl, alkylcycloalkylalkyl, cycloalkylalkyl, cycloalkoxyalkyl, cycloalkylalkoxyalkyl, alkoxyalkyl, haloalkoxyalkyl, alkoxyalkoxyalkyl or substituted heteroaryl, wherein substituted heteroaryl is substituted with $R^{22}$, $R^{23}$ and $R^{24}$;

$R^{18}$ is H, alkyl, haloalkyl, cycloalkyl, alkoxyalkyl, haloalkoxyalkyl or hydroxyalkyl;

$R^{19}$, $R^{20}$, $R^{21}$, $R^{22}$, $R^{23}$ and $R^{24}$ are independently selected from H, halogen, alkyl, haloalkyl, cycloalkyl, alkoxy and haloalkoxy;

n is zero, 1 or 2;

p is zero or 1;

or pharmaceutically acceptable salts or esters.

A further embodiment of the present invention are compounds according to formula (I) as described herein, wherein $R^1$, $R^2$, $R^3$ and $R^4$ are independently selected from H, halogen, cyano, alkyl and haloalkyl.

A particular embodiment of the present invention are compounds according to formula (I) as described herein, wherein $R^1$ is H or halogen.

In a further embodiment of the present invention are compounds according to formula (I) as described herein, wherein $R^2$ is H, alkyl or halogen.

Another further embodiment of the present invention are compounds according to formula (I) as described herein, wherein $R^2$ is H or halogen.

Another embodiment of the present invention are compounds according to formula (I) as described herein, wherein $R^3$ is halogen, cyano or haloalkyl.

The present invention also relates to compounds according to formula (I) as described herein, wherein $R^3$ is cyano or haloalkyl.

A further particular embodiment of the present invention are compounds according to formula (I) as described herein, wherein $R^3$ is haloalkyl.

A more particular embodiment of the present invention are compounds according to formula (I) as described herein, wherein $R^4$ is H or halogen.

Also an embodiment of the present invention are compounds according to formula (I) as described herein, wherein $R^4$ is H.

The present invention also relates to compounds according to formula (I) as described herein, wherein $R^5$ is H.

Another embodiment of the present invention are compounds according to formula (I) as described herein, wherein $R^6$ is H or aryl substituted with $R^{19}$, $R^{20}$ and $R^{21}$.

A further particular embodiment of the present invention are compounds according to formula (I) as described herein, wherein $R^6$ is H, deuterium, alkyl, haloalkyl, cycloalkyl, substituted aryl or substituted heteroaryl, wherein substituted aryl or substituted heteroaryl are substituted with $R^{19}$, $R^{20}$ and $R^{21}$.

A further particular embodiment of the present invention are compounds according to formula (I) as described herein, wherein $R^6$ is H.

A further particular embodiment of the present invention are compounds according to formula (I) as described herein, wherein $R^6$ is deuterium.

A particular embodiment of the present invention are compounds according to formula (I) as described herein, wherein $R^7$, $R^8$, $R^9$, $R^{10}$, $R^{11}$ and $R^{12}$ are independently selected from H, deuterium, halogen, alkyl and haloalkyl.

A particular embodiment of the present invention are compounds according to formula (I) as described herein, wherein $R^7$, $R^8$, $R^9$, $R^{10}$, $R^{11}$ and $R^{12}$ are independently selected from H and alkyl.

A particular embodiment of the present invention are compounds according to formula (I) as described herein, wherein $R^7$, $R^8$, $R^9$, $R^{10}$, $R^{11}$ and $R^{12}$ are independently selected from H and deuterium.

Also an embodiment of the present invention are compounds according to formula (I) as described herein, wherein $R^7$ is H or alkyl.

The present invention also relates to compounds according to formula (I) as described herein, wherein $R^8$, $R^9$, $R^{10}$, $R^{11}$ and $R^{12}$ are H.

A particular embodiment of the present invention are compounds according to formula (I) as described herein, wherein $R^8$, $R^9$, $R^{10}$, $R^{11}$ and $R^{12}$ are independently selected from H and deuterium.

Another embodiment of the present invention are compounds according to formula (I) as described herein, wherein A is —$(CR^{13}R^{14})_p$—$NR^{15}R^{16}$.

The present invention also relates to compounds according to formula (I) as described herein, wherein A is —$(CR^{13}R^{14})_p$—$OR^{16}$.

Also an embodiment of the present invention are compounds according to formula (I) as described herein, wherein $R^{15}$ is H.

Another embodiment of the present invention are compounds according to formula (I) as described herein, wherein $R^{16}$ is H, alkyl, —$S(O)_2R^{17}$, —$S(O)_2NR^{17}R^{18}$, —$C(O)R^{17}$, —$C(O)OR^{17}$ or —$C(O)NR^{17}R^{18}$.

Also an embodiment of the present invention are compounds according to formula (I) as described herein, wherein in case A is —$(CR^{13}R^{14})_p$—$NR^{15}R^{16}$, then $R^{16}$ is H, —$S(O)_2R^{17}$, —$S(O)_2NR^{17}R^{18}$, —$C(O)R^1$, —$C(O)OR^{17}$ or —$C(O)NR^{17}R^{18}$.

A particular embodiment of the present invention are compounds according to formula (I) as described herein, wherein in case A is or —$(CR^{13}R^{14})_p$—$OR^{16}$, then $R^{16}$ is H, alkyl or —$C(O)NR^{17}R^{18}$.

A further particular embodiment of the present invention are compounds according to formula (I) as described herein, wherein $R^{16}$ is —$S(O)_2R^{17}$ or —$C(O)R^{17}$.

A more particular embodiment of the present invention are compounds according to formula (I) as described herein, wherein $R^{16}$ is —$C(O)R^{17}$.

Another more particular embodiment of the present invention are compounds according to formula (I) as described herein, wherein $R^{16}$ is —$S(O)_2R^{17}$.

A more particular embodiment of the present invention are compounds according to formula (I) as described herein, wherein $R^{17}$ is alkyl or hydroxyalkyl.

Also a particular embodiment of the present invention are compounds according to formula (I) as described herein, wherein $R^{18}$ is H.

Also a particular embodiment of the present invention are compounds according to formula (I) as described herein, wherein $R^{19}$, $R^{20}$ and $R^{21}$ are independently selected from H and alkyl.

Another embodiment of the present invention are compounds according to formula (I) as described herein, wherein $R^{19}$ is H or alkyl.

Another embodiment of the present invention are compounds according to formula (I) as described herein, wherein $R^{20}$ is H or alkyl.

Also an embodiment of the present invention are compounds according to formula (I) as described herein, wherein $R^{21}$ is H.

Also an embodiment of the present invention are compounds according to formula (I) as described herein, wherein n is zero or 1.

Also an embodiment of the present invention are compounds according to formula (I) as described herein, wherein n is zero.

Also an embodiment of the present invention are compounds according to formula (I) as described herein, wherein n is 1.

A further embodiment of the present invention are compounds according to formula (I) as described herein, wherein p is 0.

Particular examples of compounds of formula (I) as described herein are selected from (rac)-4-(8-Amino-5,6,7,8-tetrahydroisoquinolin-4-yl)benzonitrile;
(rac)-N-(4-(4-Cyanophenyl)-5,6,7,8-tetrahydroisoquinolin-8-yl)ethanesulfonamide;
(rac)-N-[4-(4-Cyanophenyl)-5,6,7,8-tetrahydroisoquinolin-8-yl]-N'-propylsulfuric diamide;
(rac)-1-(4-(4-Cyanophenyl)-5,6,7,8-tetrahydroisoquinolin-8-yl)-3-ethylurea;
(rac)-N-(4-(4-Cyanophenyl)-5,6,7,8-tetrahydroisoquinolin-8-yl)propionamide;
(−)-(S or R)—N-(4-(4-Cyanophenyl)-5,6,7,8-tetrahydroisoquinolin-8-yl)propionamide;
(+)-(R or S)—N-(4-(4-Cyanophenyl)-5,6,7,8-tetrahydroisoquinolin-8-yl)propionamide;
(rac)-N-(4-(4-Cyanophenyl)-5,6,7,8-tetrahydroisoquinolin-8-yl)acetamide;
(rac)-N-(4-(4-Cyanophenyl)-5,6,7,8-tetrahydroisoquinolin-8-yl)isobutyramide;
(rac)-Ethyl 4-(4-cyanophenyl)-5,6,7,8-tetrahydroisoquinolin-8-ylcarbamate;
(rac)-4-(8-Hydroxy-5,6,7,8-tetrahydroisoquinolin-4-yl)benzonitrile;
(rac)-4-(4-Cyanophenyl)-5,6,7,8-tetrahydroisoquinolin-8-yl ethylcarbamate;
(rac)-4-(8-Methoxy-5,6,7,8-tetrahydroisoquinolin-4-yl)benzonitrile;
(rac)-4-(8-(3,4-Dimethylphenyl)-8-hydroxy-5,6,7,8-tetrahydroisoquinolin-4-yl)benzonitrile;
(+)-(S or R)-4-(8-(3,4-Dimethylphenyl)-8-hydroxy-5,6,7,8-tetrahydroisoquinolin-4-yl)benzonitrile;
(−)-(R or S)-4-(8-(3,4-Dimethylphenyl)-8-hydroxy-5,6,7,8-tetrahydroisoquinolin-4-yl)benzonitrile;
(rac)-N-(4-(4-Cyanophenyl)-6,7-dihydro-5H-cyclopenta[c]pyridin-7-yl)propionamide;
(−)-(S or R)—N-(4-(4-Cyanophenyl)-6,7-dihydro-5H-cyclopenta[c]pyridin-7-yl)propionamide;
(+)-(R or S)—N-(4-(4-Cyanophenyl)-6,7-dihydro-5H-cyclopenta[c]pyridin-7-yl)propionamide;
(rac)-N-(4-(3-Chloro-4-fluorophenyl)-5,6,7,8-tetrahydroisoquinolin-8-yl)propionamide;
(rac)-N-(4-(4-(Trifluoromethyl)phenyl)-5,6,7,8-tetrahydroisoquinolin-8-yl)propionamide;
(−)-(S or R)—N-(4-(4-(Trifluoromethyl)phenyl)-5,6,7,8-tetrahydroisoquinolin-8-yl)propionamide;
(+)-(R or S)—N-(4-(4-(Trifluoromethyl)phenyl)-5,6,7,8-tetrahydroisoquinolin-8-yl)propionamide;
(rac)-N-(4-(4-Chlorophenyl)-5,6,7,8-tetrahydroisoquinolin-8-yl)propionamide;
(−)-(S or R)—N-(4-(4-Chlorophenyl)-5,6,7,8-tetrahydroisoquinolin-8-yl)propionamide;
(+)-(R or S)—N-(4-(4-Chlorophenyl)-5,6,7,8-tetrahydroisoquinolin-8-yl)propionamide;
(rac)-N-(4-(4-Fluoro-3-methylphenyl)-5,6,7,8-tetrahydroisoquinolin-8-yl)propionamide;
(−)-(S or R)—N-(4-(4-Fluoro-3-methylphenyl)-5,6,7,8-tetrahydroisoquinolin-8-yl)propionamide;
(+)-(R or S)—N-(4-(4-Fluoro-3-methylphenyl)-5,6,7,8-tetrahydroisoquinolin-8-yl)propionamide;
(rac)-N-(4-(4-Chloro-2-fluorophenyl)-5,6,7,8-tetrahydroisoquinolin-8-yl)propionamide;
(−)-(S or R)—N-(4-(4-Chloro-2-fluorophenyl)-5,6,7,8-tetrahydroisoquinolin-8-yl)propionamide;
(+)-(R or S)—N-(4-(4-Chloro-2-fluorophenyl)-5,6,7,8-tetrahydroisoquinolin-8-yl)propionamide;
(rac)-N-(4-(2-Fluoro-4-(trifluoromethyl)phenyl)-5,6,7,8-tetrahydroisoquinolin-8-yl)propionamide;
(−)-(S or R)—N-(4-(2-Fluoro-4-(trifluoromethyl)phenyl)-5,6,7,8-tetrahydroisoquinolin-8-yl)propionamide;
(+)-(R or S)—N-(4-(2-Fluoro-4-(trifluoromethyl)phenyl)-5,6,7,8-tetrahydroisoquinolin-8-yl)propionamide;
(rac)-N-(4-(4-Chloro-3-fluorophenyl)-5,6,7,8-tetrahydroisoquinolin-8-yl)propionamide;
(−)-(S or R)—N-(4-(4-Chloro-3-fluorophenyl)-5,6,7,8-tetrahydroisoquinolin-8-yl)propionamide;
(+)-(R or S)—N-(4-(4-Chloro-3-fluorophenyl)-5,6,7,8-tetrahydroisoquinolin-8-yl)propionamide;
(rac)-N-(4-(3-Fluoro-4-(trifluoromethyl)phenyl)-5,6,7,8-tetrahydroisoquinolin-8-yl)propionamide;
(−)-(S or R)—N-(4-(3-Fluoro-4-(trifluoromethyl)phenyl)-5,6,7,8-tetrahydroisoquinolin-8-yl)propionamide;
(+)-(R or S)—N-(4-(3-Fluoro-4-(trifluoromethyl)phenyl)-5,6,7,8-tetrahydroisoquinolin-8-yl)propionamide;
(rac)-N-(4-(2,4-Difluorophenyl)-5,6,7,8-tetrahydroisoquinolin-8-yl)propionamide;
(rac)-N-(4-(2,4,5-Trifluorophenyl)-5,6,7,8-tetrahydroisoquinolin-8-yl)propionamide;
(rac)-N-(4-(3,4-Difluorophenyl)-5,6,7,8-tetrahydroisoquinolin-8-yl)propionamide;
(rac)-N-(4-(3,4-Dichlorophenyl)-5,6,7,8-tetrahydroisoquinolin-8-yl)propionamide;
(R)-2-Hydroxy-N—[(S,R)-4-(4-trifluoromethyl-phenyl)-5,6,7,8-tetrahydro-isoquinolin-8-yl]-propionamide;
(+)-(R)-2-Hydroxy-N—[(R or S)-4-(4-trifluoromethyl-phenyl)-5,6,7,8-tetrahydro-isoquinolin-8-yl]-propionamide;
(−)-(R)-2-Hydroxy-N—[(S or R)-4-(4-trifluoromethyl-phenyl)-5,6,7,8-tetrahydro-isoquinolin-8-yl]-propionamide;
(rac)-N-(4-(4-(Trifluoromethyl)phenyl)-6,7-dihydro-5H-cyclopenta[c]pyridin-7-yl)propionamide;
(−)-(S or R)—N-(4-(4-(Trifluoromethyl)phenyl)-6,7-dihydro-5H-cyclopenta[c]pyridin-7-yl)propionamide;
(+)-(R or S)—N-(4-(4-(Trifluoromethyl)phenyl)-6,7-dihydro-5H-cyclopenta[c]pyridin-7-yl)propionamide;

(R)-2-Hydroxy-N—((R,S)-4-(4-(trifluoromethyl)phenyl)-6,7-dihydro-5H-cyclopenta[c]pyridin-7-yl)propanamide;
(−)-(R)-2-Hydroxy-N—((S or R)-4-(4-(trifluoromethyl)phenyl)-6,7-dihydro-5H-cyclopenta[c]pyridin-7-yl)propanamide;
(+)-(R)-2-Hydroxy-N—((R or S)-4-(4-(trifluoromethyl)phenyl)-6,7-dihydro-5H-cyclopenta[c]pyridin-7-yl)propanamide;
(rac)-N-(4-(4-Chloro-3-fluorophenyl)-6,7-dihydro-5H-cyclopenta[c]pyridin-7-yl)propionamide;
(−)-(S or R)—N-(4-(4-Chloro-3-fluorophenyl)-6,7-dihydro-5H-cyclopenta[c]pyridin-7-yl)propionamide;
(+)-(R or S)—N-(4-(4-Chloro-3-fluorophenyl)-6,7-dihydro-5H-cyclopenta[c]pyridin-7-yl)propionamide;
(rac)-N-(4-(4-Fluoro-3-methylphenyl)-6,7-dihydro-5H-cyclopenta[c]pyridin-7-yl)propionamide;
(−)-(S or R)—N-(4-(4-Fluoro-3-methylphenyl)-6,7-dihydro-5H-cyclopenta[c]pyridin-7-yl)propionamide;
(+)-(R or S)—N-(4-(4-Fluoro-3-methylphenyl)-6,7-dihydro-5H-cyclopenta[c]pyridin-7-yl)propionamide;
(rac)-N-(4-(2-Fluoro-4-(trifluoromethyl)phenyl)-6,7-dihydro-5H-cyclopenta[c]pyridin-7-yl)propionamide;
(−)-(S or R)—N-(4-(2-Fluoro-4-(trifluoromethyl)phenyl)-6,7-dihydro-5H-cyclopenta[c]pyridin-7-yl)propionamide;
(+)-(R or S)—N-(4-(2-Fluoro-4-(trifluoromethyl)phenyl)-6,7-dihydro-5H-cyclopenta[c]pyridin-7-yl)propionamide;
(rac)-N-(4-(4-(Trifluoromethyl)phenyl)-6,7-dihydro-5H-cyclopenta[c]pyridin-7-yl)ethanesulfonamide;
(−)-(S or R)—N-(4-(4-(Trifluoromethyl)phenyl)-6,7-dihydro-5H-cyclopenta[c]pyridin-7-yl)ethanesulfonamide;
(+)-(R or S)—N-(4-(4-(Trifluoromethyl)phenyl)-6,7-dihydro-5H-cyclopenta[c]pyridin-7-yl)ethanesulfonamide;
N-[(7R,8S or 7S,8R)-7-Methyl-4-(4-trifluoromethyl-phenyl)-5,6,7,8-tetrahydro-isoquinolin-8-yl]-propionamide;
N-[(7S,8S or 7R,8R)-7-Methyl-4-(4-trifluoromethyl-phenyl)-5,6,7,8-tetrahydro-isoquinolin-8-yl]-propionamide;
N-[(7S,8R or 7R,8S)-7-Methyl-4-(4-trifluoromethyl-phenyl)-5,6,7,8-tetrahydro-isoquinolin-8-yl]-propionamide;
N-[(7R,8R or 7S,8S)-7-Methyl-4-(4-trifluoromethyl-phenyl)-5,6,7,8-tetrahydro-isoquinolin-8-yl]-propionamide;
and pharmaceutically acceptable salts thereof.

Also particular examples of compounds of formula (I) as described herein are selected from
(rac)-N-(4-(3-Fluoro-4-(trifluoromethyl)phenyl)-6,7-dihydro-5H-cyclopenta[c]pyridin-7-yl)ethanesulfonamide;
(−)-(S or R)—N-(4-(3-Fluoro-4-(trifluoromethyl)phenyl)-6,7-dihydro-5H-cyclopenta[c]pyridin-7-yl)ethanesulfonamide;
(+)-(R or S)—N-(4-(3-Fluoro-4-(trifluoromethyl)phenyl)-6,7-dihydro-5H-cyclopenta[c]pyridin-7-yl)ethanesulfonamide;
(+)-(R)-4-(2-Fluoro-4-(trifluoromethyl)phenyl)-5,6,7,8-tetrahydroisoquinolin-8-amine;
(+)-(R)—N-(4-(2-Fluoro-4-(trifluoromethyl)phenyl)-5,6,7,8-tetrahydroisoquinolin-8-yl)acetamide;
(+)-(R)—N-(4-(2-Fluoro-4-(trifluoromethyl)phenyl)-5,6,7,8-tetrahydroisoquinolin-8-yl)methanesulfonamide;
(+)-(R)—N-(4-(4-(Trifluoromethyl)phenyl)-5,6,7,8-tetrahydroisoquinolin-8-yl)acetamide;
(+)-(R)—N-(4-(4-Cyanophenyl)-5,6,7,8-tetrahydroisoquinolin-8-yl)acetamide;
(+)-(R)—N-(4-(3-Fluoro-4-(trifluoromethyl)phenyl)-5,6,7,8-tetrahydroisoquinolin-8-yl)acetamide;
(rac)-4-(2-Fluoro-4-(trifluoromethyl)phenyl)-6,7-dihydro-5H-cyclopenta[c]pyridin-7-ol;
(rac)-4-(7-Hydroxy-6,7-dihydro-5H-cyclopenta[c]pyridin-4-yl)benzonitrile;
(rac)-4-(3-Fluoro-4-(trifluoromethyl)phenyl)-6,7-dihydro-5H-cyclopenta[c]pyridin-7-ol;
(rac)-4-(4-(Trifluoromethyl)phenyl)-6,7-dihydro-5H-cyclopenta[c]pyridin-7-ol;
(rac)-7-methyl-4-(4-(Trifluoromethyl)phenyl)-6,7-dihydro-5H-cyclopenta[c]pyridin-7-ol;
(+)-(7R or 7S)-6,6-Dimethyl-4-[4-(trifluoromethyl)phenyl]-5,7-dihydrocyclopenta[c]pyridin-7-ol;
(−)-(7S or 7R)-6,6-Dimethyl-4-[4-(trifluoromethyl)phenyl]-5,7-dihydrocyclopenta[c]pyridin-7-ol;
(+)-4-[(7R or 7S)-7-Hydroxy-6,6-dimethyl-5,7-dihydrocyclopenta[c]pyridin-4-yl]benzonitrile;
(−)-4-[(7S or 7R)-7-Hydroxy-6,6-dimethyl-5,7-dihydrocyclopenta[c]pyridin-4-yl]benzonitrile;
(rac)-4-(3-Fluoro-4-trifluoromethyl-phenyl)-6,7-dihydro-5H-[2]pyrindin-7-ylamine;
(rac)-N-(4-(3-Fluoro-4-(trifluoromethyl)phenyl)-6,7-dihydro-5H-cyclopenta[c]pyridin-7-yl)propionamide;
(rac)-Cyclopropanesulfonic acid [4-(3-fluoro-4-trifluoromethyl-phenyl)-6,7-dihydro-5H-[2]pyrindin-7-yl]-amide;
(rac)-Propionic acid 4-(3-fluoro-4-trifluoromethyl-phenyl)-6,7-dihydro-5H-[2]pyrindin-7-yl ester;
(rac)-4-(4-(Trifluoromethyl)phenyl)-6,7-dihydro-5H-cyclopenta[c]pyridin-7-amine;
(rac)-N-(4-(4-(Trifluoromethyl)phenyl)-6,7-dihydro-5H-cyclopenta[c]pyridin-7-yl)cyclopropanesulfonamide;
(rac)-N-(4-(4-(Trifluoromethyl)phenyl)-6,7-dihydro-5H-cyclopenta[c]pyridin-7-yl)methanesulfonamide;
(rac)-N-(4-(4-(Trifluoromethyl)phenyl)-6,7-dihydro-5H-cyclopenta[c]pyridin-7-yl)propane-1-sulfonamide;
(rac)-tert-Butyl 2-(4-(4-(trifluoromethyl)phenyl)-6,7-dihydro-5H-cyclopenta[c]pyridin-7-yloxy)acetate;
(rac)-Methyl 2-(4-(4-(trifluoromethyl)phenyl)-6,7-dihydro-5H-cyclopenta[c]pyridin-7-yloxy)acetate;
(rac)-2-(4-(4-(Trifluoromethyl)phenyl)-6,7-dihydro-5H-cyclopenta[c]pyridin-7-yloxy)acetic acid hydrochloride;
(rac)-N-Methyl-2-(4-(4-(trifluoromethyl)phenyl)-6,7-dihydro-5H-cyclopenta[c]pyridin-7-yloxy)acetamide;
(rac)-N,N-Dimethyl-2-(4-(4-(trifluoromethyl)phenyl)-6,7-dihydro-5H-cyclopenta[c]pyridin-7-yloxy)acetamide;
(rac)-2-(4-(4-(Trifluoromethyl)phenyl)-6,7-dihydro-5H-cyclopenta[c]pyridin-7-yloxy)acetamide;
(rac)-7-((3-Methyloxetan-3-yl)methoxy)-4-(4-(trifluoromethyl)phenyl)-6,7-dihydro-5H-cyclopenta[c]pyridine;
(rac)-4-(4-(Trifluoromethyl)phenyl)-5,6,7,8-tetrahydroisoquinolin-8-ol;
(−)-(S)-4-(4-(Trifluoromethyl)phenyl)-5,6,7,8-tetrahydroisoquinolin-8-ol;
(+)-(R)-4-(4-(Trifluoromethyl)phenyl)-5,6,7,8-tetrahydroisoquinolin-8-ol;
(R)—N-(4-(2-Cyclopropyl-4-(trifluoromethyl)phenyl)-5,6,7,8-tetrahydroisoquinolin-8-yl)propionamide;
(+)-(7R or 7S)-4-[3-Fluoro-4-(trifluoromethyl)phenyl]-6,6-dimethyl-5,7-dihydrocyclopenta[c]-pyridin-7-ol;
(−)-(7S or 7R)-4-[3-Fluoro-4-(trifluoromethyl)phenyl]-6,6-dimethyl-5,7-dihydrocyclopenta[c]-pyridin-7-ol;
and pharmaceutically acceptable salts thereof.

Further particular examples of compounds of formula (I) as described herein are selected from
(+)-(R or S)—N-(4-(4-Cyanophenyl)-5,6,7,8-tetrahydroisoquinolin-8-yl)propionamide;
(+)-(R or S)—N-(4-(4-(Trifluoromethyl)phenyl)-5,6,7,8-tetrahydroisoquinolin-8-yl)propionamide;
(+)-(R or S)—N-(4-(2-Fluoro-4-(trifluoromethyl)phenyl)-5,6,7,8-tetrahydroisoquinolin-8-yl)propionamide;
(+)-(R or S)—N-(4-(3-Fluoro-4-(trifluoromethyl)phenyl)-5,6,7,8-tetrahydroisoquinolin-8-yl)propionamide;

(+)-(R or S)—N-(4-(4-(Trifluoromethyl)phenyl)-6,7-dihydro-5H-cyclopenta[c]pyridin-7-yl)propionamide;
(+)-(R or S)—N-(4-(2-Fluoro-4-(trifluoromethyl)phenyl)-6,7-dihydro-5H-cyclopenta[c]pyridin-7-yl)propionamide;
N-[(7S,8R or 7R,8S)-7-Methyl-4-(4-trifluoromethyl-phenyl)-5,6,7,8-tetrahydro-isoquinolin-8-yl]-propionamide;
and pharmaceutically acceptable salts thereof.

Also further particular examples of compounds of formula (I) as described herein are selected from
(rac)-4-(2-Fluoro-4-(trifluoromethyl)phenyl)-6,7-dihydro-5H-cyclopenta[c]pyridin-7-ol;
(+)-(7R or 7S)-6,6-Dimethyl-4-[4-(trifluoromethyl)phenyl]-5,7-dihydrocyclopenta[c]pyridin-7-ol;
(rac)-N-(4-(3-Fluoro-4-(trifluoromethyl)phenyl)-6,7-dihydro-5H-cyclopenta[c]pyridin-7-yl)propionamide;
(rac)-N,N-Dimethyl-2-(4-(4-(trifluoromethyl)phenyl)-6,7-dihydro-5H-cyclopenta[c]pyridin-7-yloxy)acetamide;
(+)-(7R or 7S)-4-[3-Fluoro-4-(trifluoromethyl)phenyl]-6,6-dimethyl-5,7-dihydrocyclopenta[c]-pyridin-7-ol;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

The following abbreviations are used in the present text:
AcOH=acetic acid, BOC=t-butyloxycarbonyl, BuLi=butyllithium, CDI=1,1-carbonyldiimidazole, $CH_2Cl_2$=dichloromethane, DBU=2,3,4,6,7,8,9,10-octahydro-pyrimido[1,2-a]azepine, DCE=1,2-dichloroethane, DIBALH=di-i-butylaluminium hydride, DCC=N,N'-dicyclohexylcarbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, $Et_2O$=diethylether, $Et_3N$=triethylamine, eq=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=$iPr_2NEt$=N-ethyl diisopropylamine, IPC=in process control, LAH=lithium aluminium hydride, LDA=lithium diisopropylamide, HMDS=hexamethydisilazane, $LiBH_4$=lithium borohydride, MeOH=methanol, $NaBH_3CN$=sodium cyanoborohydride, $NaBH_4$=sodium borohydride, NaI=sodium iodide, Red-Al=sodium bis(2-methoxyethoxy) aluminium hydride, RT=room temperature, TBDMSCl=t-butyldimethylsilyl chloride, TFA=trifluoroacetic acid, THF=tetrahydrofuran, quant=quantitative.

Intermediates described in the Schemes which are deprotonated and alkylated afterwards can also be deuterated by addition of $D_2O$, MeOD or AcOD, a reaction preferably performed between −78° C. and room temperature to give deuterium analogue intermediates.

Phenyl compounds 2 (Scheme 1) are known or can be prepared by methods described herein or known to the man skilled in the art.

Reaction of phenyl 2 with e.g. 4,4,4',4',5,5,5',5'-octamethyl-2,2'-bi(1,3,2-5 dioxaborolane) in solvents like dimethylsulfoxide or dioxane in the presence of potassium acetate and catalysts like (1,1'-bis-diphenylphosphino)-ferrocene) palladium-(II)dichloride (1:1 complex with dichloromethane) at temperatures up to about 100° C. gives boronic ester compounds 3 (step b). Condensation of boronic ester compounds 3 with suitable aryl halides 4 (for possible syntheses of aryl halides or triflates see Schemes 2a, 2b, 2c and 2d) can be performed using Suzuki conditions, e.g. in the presence of catalysts, such as tri-o-tolylphosphine/palladium (II)acetate, tetrakis-(triphenylphosphine)-palladium, bis (triphenylphosphine)palladium(II)chloride or dichloro[1,1'-bis(diphenylphosphino)-ferrocene]palladium(II) optionally in the form of a dichloromethane complex (1:1), and in the presence of a base, such as aqueous or non aqueous potassium phosphate, sodium or potassium carbonate, in a solvent, such as dimethylsulfoxide, toluene, ethanol, dioxane, tetrahydrofuran or N,N-dimethylformamide, optionally mixed with water and in an inert atmosphere such as argon or nitrogen, in a temperature range preferably between room temperature and about 130° C. leading to products 5 (steps c). Substituent A in 5 can further be transformed as described in Scheme 2c and Scheme 2d

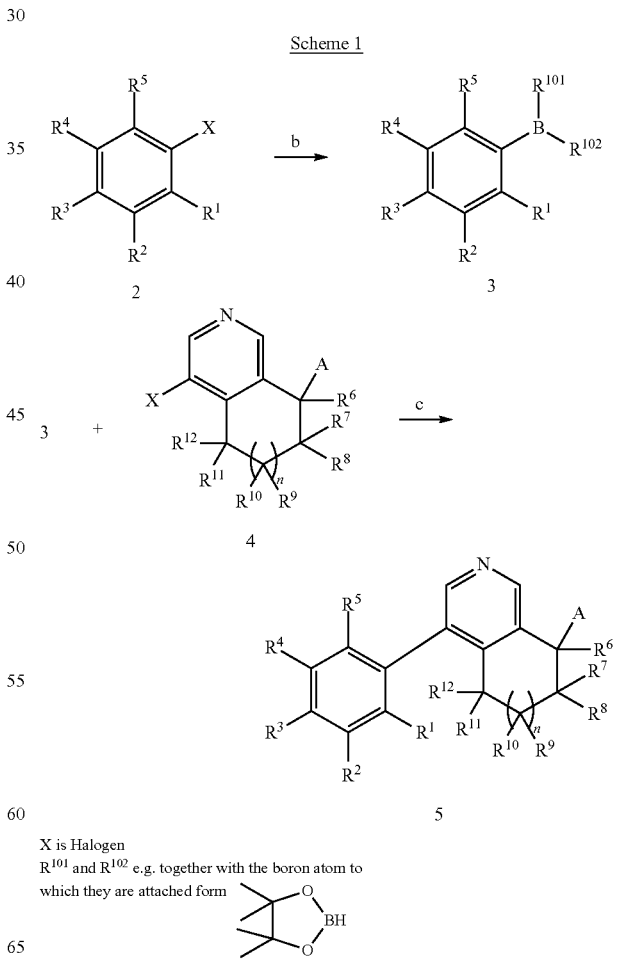

Schemes 2a, 2b, 2c and 2d describe the preparation of compounds that can serve as intermediates 4, such as compounds 104, 106, 108, 109, 110, 113, 114 and 115.

Ketones 101a (Scheme 3a), 101b (Scheme 3a), 101c (Scheme 3b), 101d (Scheme 3c), 101e (Scheme 3d) with X=halogen can be transformed via Suzuki reaction described in Scheme 1 (step c) wherein X becomes phenyl substituted by R1, R2, R3, R4 and R5, each substituents being optionally protected by a protecting group known to the man skilled in the art.

Treatment of ketones 101a and 101f (scheme 3e) (n is zero), 101b (n is 1), 101d (n is 2) and 101c or 101e by a Wittig reaction using (methoxymethyl)-triphenylphosphonium chloride as reagent (scheme 2a, step a), subsequent reaction of the Wittig product 102 with acid (step b) and oxidation of the aldehyde formed gives the corresponding acids (step c with e.g. using sodium chlorate, sodium dihydrogen-phosphate in a mixture of tert-butanol and water and in the presence of 3-methyl-2-butene at temperatures around room temperature), which can be converted into suitable ester compounds 103, wherein $R^6$ is H (step d). Compounds 103, wherein $R^6$ is H, can optionally be treated with a base like LDA or lithium or potassium HMDS in solvents like tetrahydrofuran or 1,2-dimethoxyethane, followed by addition of an alkyl, haloalkyl or cycloalkyl halide, mesylate or tosylate, a reaction preferably performed between −78° C. and room temperature to give compounds 103, wherein $R^6$ is alkyl, haloalkyl or cycloalkyl, (step e). Compounds 103 can be converted into amino compounds 104 via formation of the corresponding primary amides (step f, e.g. by amide formation with ammonia in a suitable solvent as methanol, or by saponification followed by standard amide coupling with ammonia) followed by a Hofmann rearrangement: treatment with sodium hydroxide and bromine in a solvent like ethanol preferably between about 0° C. and the reflux temperature of the solvent (step g).

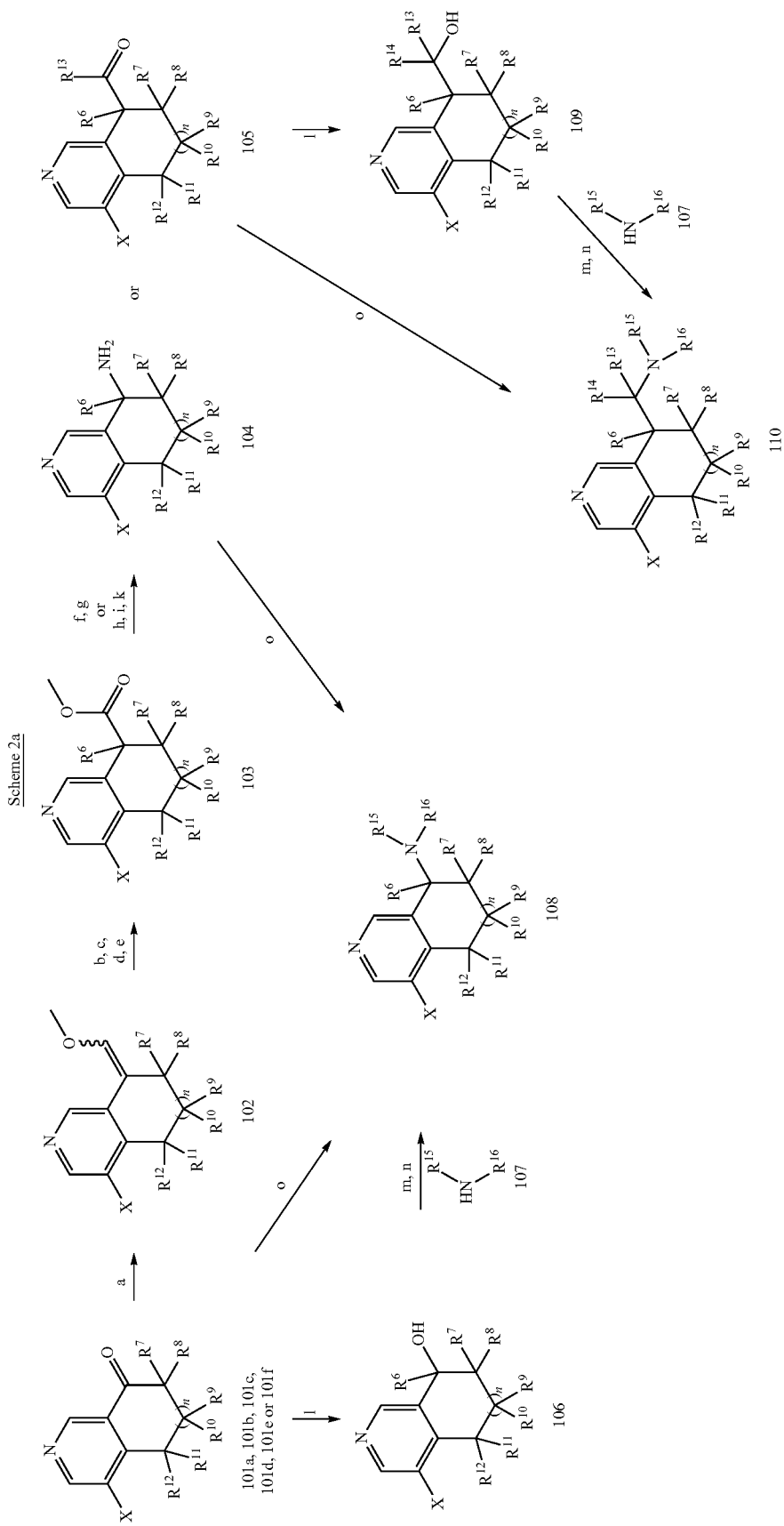

Alternatively, ester compounds 103 can converted into ketones 105 (scheme 2a), wherein $R^{13}$ is alkyl, haloalkyl, cycloalkyl or halocycloalkyl, via Weinreb amides: hydrolysis of ester 103 (step h), transformation into methoxy-N-methyl-amides (step i) followed by reaction with Grignard reagents $R^{13}MgX$ or lithium reagents $R^{13}Li$ in solvents like THF in a temperature range between −78° C. and room temperature (step k) gives ketones 105. Compounds 101 and 105 can react with a hydride reducing agent like sodium borohydride (e.g. in methanol around room temperature) or with a Grignard reagent $R^6MgX$ or $R^{14}MgX$ or with a lithium reagent $R^6Li$ or $R^{14}Li$ in solvents like THF in a temperature range between −78° C. to compounds 106 or 109 by methods well known in the art (steps l). The hydroxy substituent in 106 or 109 can be converted into a leaving group such as halogen, tosylate, mesylate or triflate by method known in the art (step m) and subsequently reacted with amino compounds 107, optionally in the presence of a base like Huenig's base or sodium hydride in solvents like DMF, DMA or 1-methyl-2-pyrrolidone in a temperature range between 0° C. and about 100° C. to give substituted amino compounds 108 or 110 (step n).

Optionally, suitable reductive amination procedures can convert aldehydes or ketones 101 or 105 (scheme 2a) into compounds 108, wherein $R^6$ is H or compounds 110, wherein $R^{13}$ and $R^{14}$ are H, e.g. by treatment with suitable amines, e.g. $NH_4OAc/NaBH(OAc)_3$ in a one step procedure in a solvent like methanol preferably around room temperature to reflux temperature or in a two step procedure by first treatment with suitable amines, e.g. ammonia in methanol and titanium (IV) isopropoxide with no additional solvent between 0° C. and room temperature or in solvents like methanol or toluene preferably at temperatures between room temperature and the reflux temperature of the solvents followed by reaction with $NaBH_4$ preferably between 0° C. and room temperature (step o).

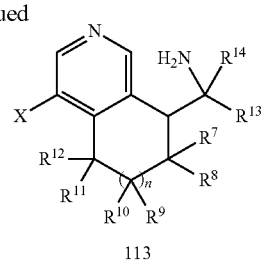

113

X is Halogen or phenyl substituted by R1, R2, R3, R4 and R5

Treatment of ketones 101a and 101f (n is zero), 101b (n is 1), 101d (n is 2) and 101c or 101e (scheme 2b) by a Horner-Emmons reactions using e.g. reagents like dimethyl(methoxycarbonyl)methylphosphonate, optionally carrying an additional $R^{13}$ substituent at the methylene group, and a base like sodium hydride in a solvent like tetrahydrofuran preferable between about 0° C. and the reflux temperature of the solvent to give unsaturated esters 111 (step q). Reduction of the double bond in unsaturated esters 111 can be performed e.g. by using a mixture of nickel chloride and sodium borohydride as reducing agents in solvents like methanol preferably between about 0° C. and room temperature and is leading to ester compounds 112, wherein $R^{14}$ is H (step r). Optional treatment of ester compounds 112, wherein $R^{14}$ is H, with a base like LDA or lithium or potassium HMDS in solvents like tetrahydrofuran or 1,2-dimethoxyethane, followed by addition of one or sequentially two different alkyl, haloalky, cycloalkyl and halocycloalkyl halides, mesylates or tosylates, a reaction preferably performed between −78° C. and room temperature gives ester compounds 112, wherein $R^{14}$ is not H (step s). Amide formation (step f) and Hofmann degradation (step g) from compound 112 gives compounds 113.

Scheme 2b

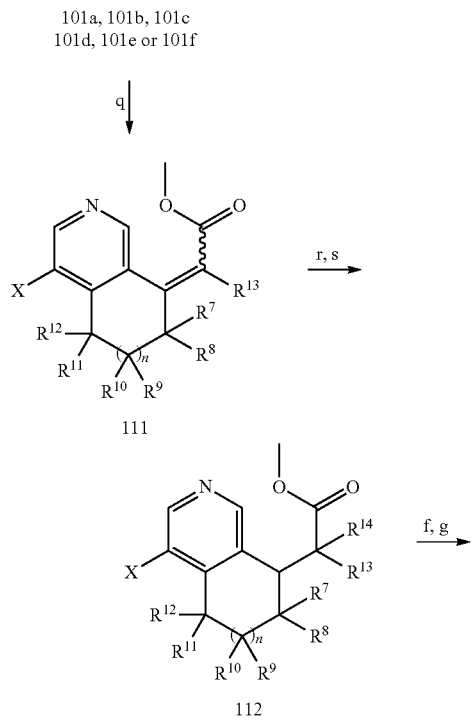

Scheme 2c

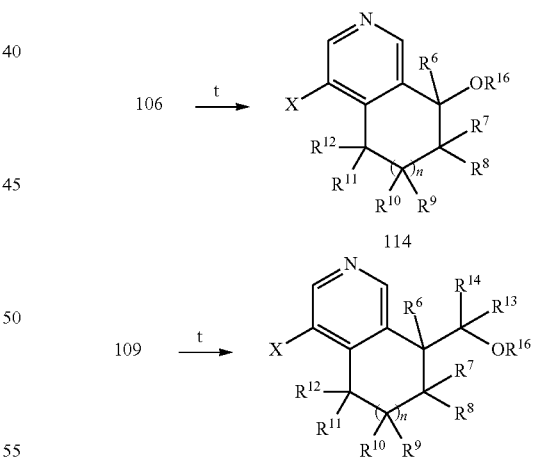

X is Halogen or phenyl substituted by R1, R2, R3, R4 and R5

Building blocks 106 and 109 (scheme 2c) can further be transformed to ethers 114 and 115, wherein $R^{16}$ is alkyl, haloalkyl, cycloalkyl, hydroxyalkyl, alkoxyalkyl or haloalkoxyalkyl, using corresponding $R^{16}$-halides, $R^{16}$-mesylates or $R^{16}$-tosylates in the presence of a base like sodium hydride or after anion formation e.g. with sodium hydride in solvents like DMF, DMA or 1-methyl-2-pyrrolidone in a temperature range between 0° C. and about 100° C. (step t).

Compounds 106 or 109 (scheme 2c) react with carboxylic acid chlorides ClC(O)R$^{17}$, chloroformates ClC(O)OR$^{17}$, isocyanates O=C=NR$^{17}$, carbamoyl chlorides ClC(O)NR$^{17}$R$^{18}$, sulfonyl chlorides —S(O)$_2$R$^{17}$, as well as with ClS(O)$_2$OR$^{17}$ and ClS(O)$_2$NR$^{17}$R$^{18}$ to the corresponding acyl- or sulfonyl-compounds compounds 114 and 115, wherein R$^{16}$ is —C(O)R$^{17}$, —C(O)OR$^{17}$—C(O)NR$^{17}$R$^{18}$, —S(O)R, —S(O)$_2$R, —S(O)$_2$OR, or —S(O)$_2$NR$^{17}$R$^{18}$, in the presence of a base like triethylamine or Huenig's base in solvents like CH$_2$Cl$_2$, THF, N,N-dimethylformamide, pyridine and optionally a catalyst like DMAP in a temperature range between about 0° C. and the reflux temperature of the solvents (step t).

Compounds 104 or 113 (scheme 2d) react with carboxylic acid chlorides ClC(O)R$^{17}$, chloroformates ClC(O)OR$^{17}$, isocyanates O=C=NR$^{17}$, carbamoyl chlorides ClC(O)NR$^{17}$R$^{18}$, sulfonyl chlorides —S(O)$_2$R$^{17}$, as well as with ClS(O)$_2$OR$^{17}$ and ClS(O)$_2$NR$^{17}$R$^{18}$ to the corresponding acyl- or sulfonyl-compounds 108 or 110, wherein R$^{16}$ is —S(O)R$^{17}$, —S(O)$_2$R$^{17}$, —S(O)$_2$OR$^{17}$, —S(O)$_2$NR$^{17}$R$^{18}$, —C(O)R$^{17}$, —C(O)OR$^{17}$ or —C(O)NR$^{17}$R$^{18}$, respectively in the presence of a base like triethylamine or Huenig's base in solvents like THF, N,N-dimethylformamide, pyridine and optionally a catalyst like DMAP in a temperature range between about 0° C. and the reflux temperature of the solvents (step a). Alternatively, amide compounds 108 or 110, wherein R$^{16}$ is —S(O)$_2$R$^{17}$ or —C(O)R$^{17}$ can be formed by amide coupling reactions between compounds 104 or 113 and acids HOC(O)R$^{17}$ by using well known coupling methods like e.g. using EDCI optionally in the presence of HOBT or DMAP and a base like Huenig's base in solvents like N,N-dimethylformamide preferably between 0° C. and room temperature or by use of HATU, triethylamine, in N,N-dimethylformamide preferably between 0° C. and room temperature (step a).

Substituents R$^{15}$ and R$^{16}$ can then be attached to amino compounds 104 and 113 using methods well known to persons skilled in the art. Substituents R$^{15}$ alkyl, haloalkyl, cycloalkyl, hydroxyalkyl, alkoxyalkyl and haloalkoxyalkyl can be introduced into compound 104 and 113 or in compounds 108 and 110 using corresponding halides, mesylates or tosylates in the presence of a base like sodium hydride or after anion formation e.g. with sodium hydride in solvents like DMF, DMA or 1-methyl-2-pyrrolidone in a temperature range between 0° C. to room temperature (step b). Step b can be carried out before step a (scheme 2d).

Alternatively, the procedures described in scheme 2d can be applied to starting material 104 and 113, wherein X is phenyl substituted by R$^1$, R$^2$, R$^3$, R$^4$ and R$^5$, each substituents being optionally protected by a protecting group known to the man skilled in the art.

5-Halo-nicotinic acid compounds 201 or 206 (Scheme 3a) react with acrylic acid ester compounds 202 or 207 after deprotonation with base like LDA or lithium or potassium HMDS in solvents like THF preferably around −78° C. giving cyclic beta keto ester compounds 203 and 208 (step a). Treatment of beta keto-ester compounds 203 or 208 with aqueous acid preferably at reflux temperature induces ester hydrolysis and subsequent decarboxylation providing ketones 101a and 101b (step b). Ester compounds 203 or 208 can be treated with a base like NaH, LDA or lithium or potassium HMDS in solvents like DMF (for NaH), tetrahydrofuran or 1,2-dimethoxyethane, followed by addition of an alkyl or cycloalkyl halide, mesylate or tosylate, or e.g. N-halobenzensulfonamide, a reaction preferably performed between −78° C. and room temperature, to give ester compounds 205 or 210 carrying a substituent R$^7$ different from H (step c). Depending on the equivalents of added bases like LDA or lithium or potassium HMDS additional R$^{11}$ and R$^{12}$ can be introduce for 205 or 210. Hydrolyses and decarboxylation as described above gives ketones 101a or 101b (step b).

Scheme 3a

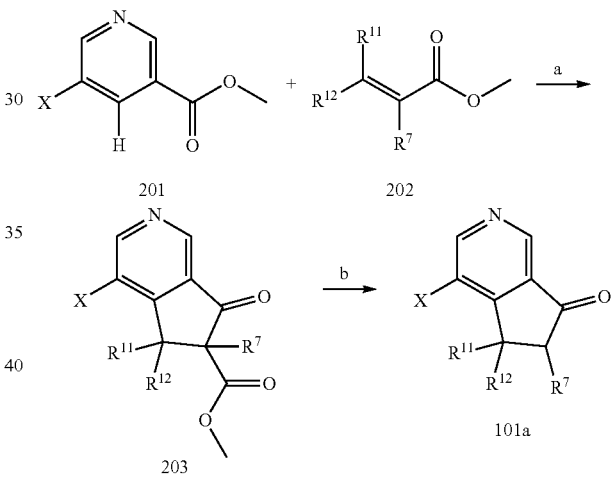

Scheme 2d

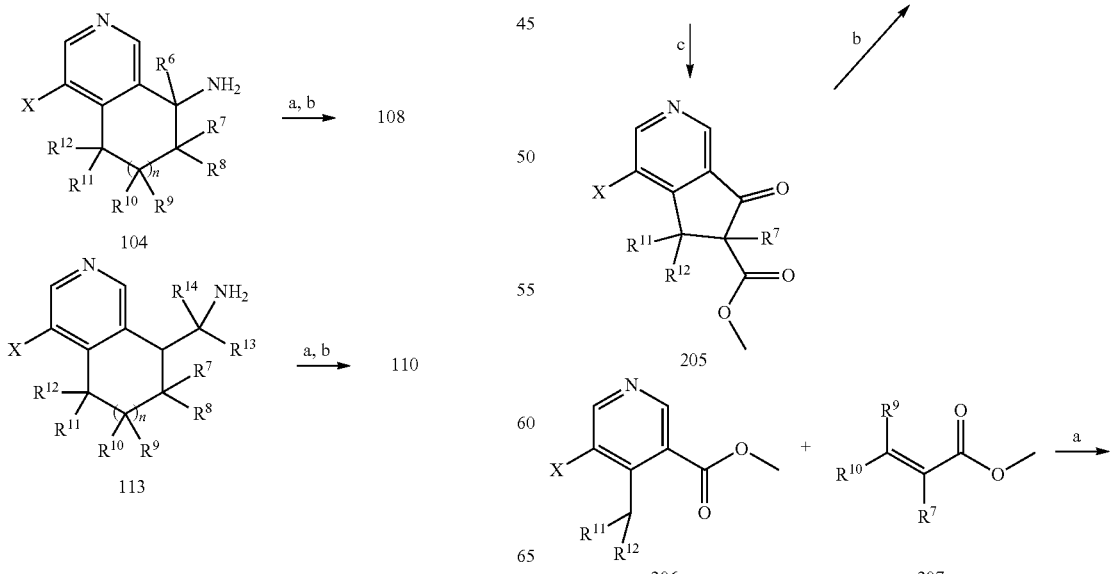

X is Halogen or phenyl substituted by R1, R2, R3, R4 and R5

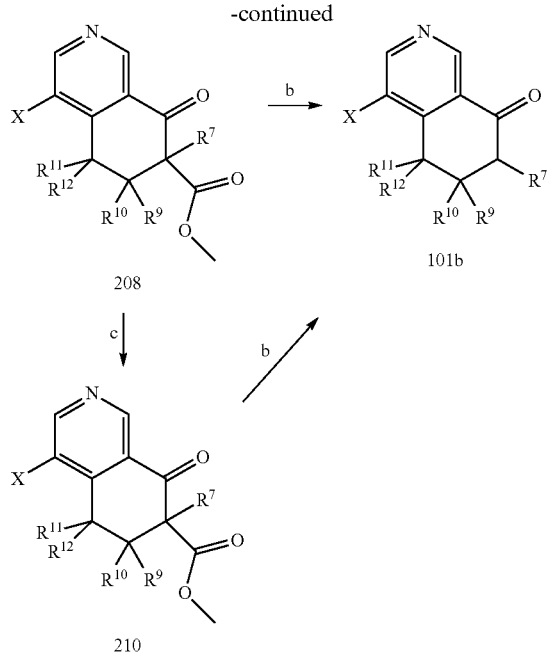

Imines 253 (scheme 3b) can be synthesized with amine $R^aNH_2$, wherein $R^a$ is e.g. alkyl, in an alcohol e.g. ethanol in the presence of a catalyst like pyridinium p-toluenesulfonate or p-toluenesulfonic acid at room temperature to reflux temperature (step a). Fluorination with N-fluorobenzenesulfonimide using $K_2CO_3$ or triethylamine as base in solvents like DMF or acetonitrile or mixtures thereof, in the presence of molecular sieve at room temperature gives compounds 101c, wherein $R^8$ is F (step b). On the other hand deprotonation and addition of an alkyl or haloalkyl halide, mesylate or tosylate, a reaction preferably performed between −78° C. and room temperature gives intermediates 101c, wherein $R^8$ is alkyl or haloalkyl. Hydrolysis with e.g. concentrated aqueous HCl in acetonitrile provides the final building blocks 101c (step c). Alternatively, 209 can be treated with a base like LDA, lithium or potassium HMDS, NaH, potassium ter-butylate or NaOH with phase transfert conditions in solvents like tetrahydrofuran, 1,2-dimethoxyethane, or in case NaH is used DMF or DMA, or in case phase transfer conditions are used, water/toluene, followed by addition of an alkyl or haloalkyl halide, mesylate or tosylate, a reaction preferably performed between −78° C. and room temperature to give ketones 101c carrying a substituent $R^8$ different from H (step d). This step can be repeated to introduce two different substituents 101c, wherein $R^8$ and $R^7$ are not H.

Scheme 3b

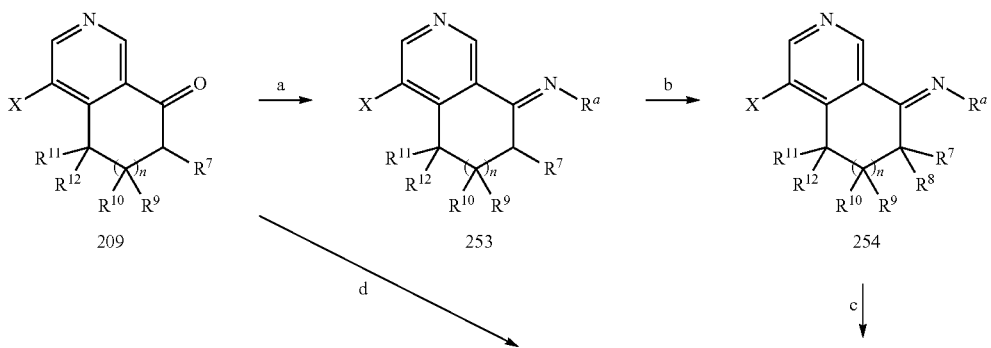

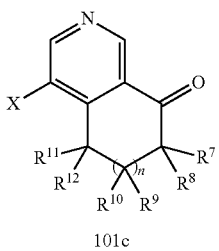

X is Halogen or phenyl substituted by R1, R2, R3, R4 and R5

5-Halo-nicotinic acid compounds 206 (Scheme 3c) react with alkene compounds 300 after deprotonation with base like LDA or lithium or potassium HMDS in solvents like THF preferably around −78° C. giving alkene 301 (step a). Diester 302 (step b) can be synthesized by methods known to persons skilled in the art such as e.g. by ozonolysis of alkenes 301 in the presence of methanolic NaOH to give compounds 302 which can be cyclized using Dieckmann condensation conditions to give beta keto-esters 303 (step c). Treatment of compounds 303 with aqueous acid preferably at reflux temperature induces ester hydrolysis and subsequent decarboxylation providing ketones 101d (step e). Ester compounds 303 can be treated with a base like NaH, LDA or lithium or potassium HMDS in solvents like DMF (for NaH), tetrahydrofuran or 1,2-dimethoxyethane, followed by addition of an alkyl or cycloalkyl halide, mesylate or tosylate, or e.g. N-halobenzensulfonamide, a reaction preferably performed between −78° C. and room temperature, to give ester compounds 303 carrying a substituent $R^7$ different from H (step d). Depending on the equivalents of added bases like LDA or lithium or potassium HMDS additional $R^{11}$ and $R^{12}$ can be introduce for 303. Hydrolyses and decarboxylation as described above gives ketones 101d (step e).

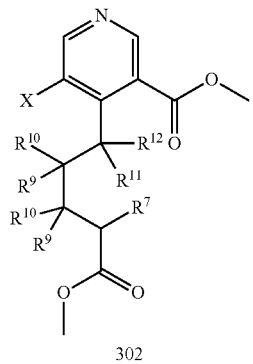

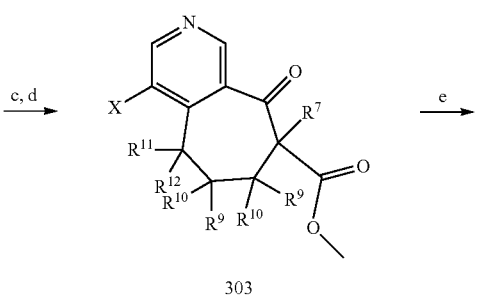

X is halogen
$X^1$ is halogen, mesylate or tosylate

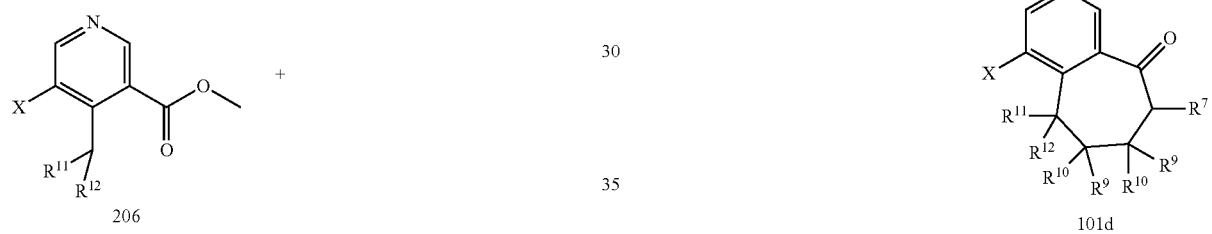

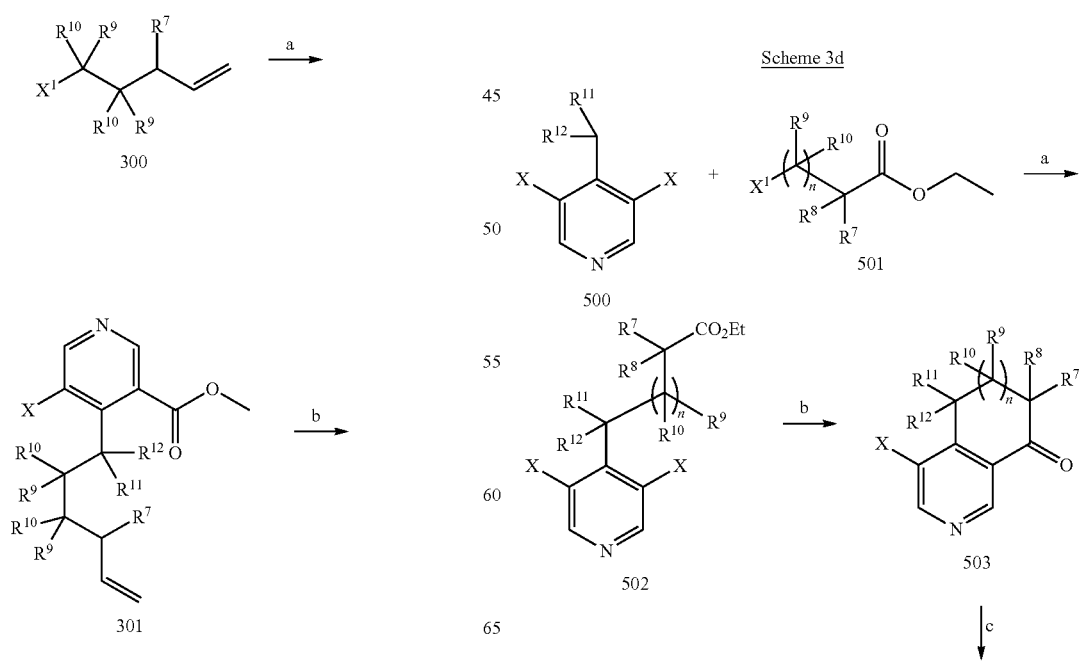

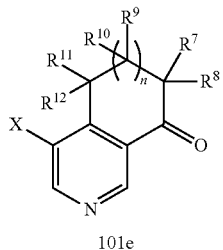

101e

X = Halogen
n = 0, 1

Alternatively, 3,5-dihalo-4-methyl-pyridine or $R^{11}$, $R^{12}$ substituted compounds 500 were deprotonated with a base like n-butyllithium, LDA or lithium or potassium HMDS in solvents like THF preferably below −70° C. can be reacted with electrophiles 501 to give ester compounds 502 (Scheme 3d, step a). Subsequent ring cyclization mediated by halogen-lithium exchange at low temperature preferably below −60° C. gives cyclized ketones 503 (step b). It can be treated with a base like NaH, LDA or lithium or potassium HMDS in solvents like DMF (for NaH), THF or 1,2-dimethoxyethane, followed by the addition of a $R^7$-halogenide or -mesylate or -tosylate followed by a second deprotonation and addition of $R^8$-halogenide or -mesylate or -tosylate (or an excess of $R^7$-halogenide if $R^7$ and $R^8$ are the same), a reaction preferably performed between −78° C. and room temperature, to give ketone compounds 101e carrying substituent $R^7$, $R^8$, and $R^9$ (n=0), $R^{10}$ (n=0) different from H (step c).

Alternatively, compounds of formula (I) can be prepared by cycloaddition reaction of oxazoles 400 with cyclopropanes 401 at elevated temperatures (Scheme 3e). This hetero Diels-Alder reaction is also known as the Kondrat'eva reaction (see: J. I. Levin, S. M. Weinreb, *J. Org. Chem.* 1984, 49, 4325) and provides convenient access to annulated pyridine systems. Oxazoles substituted in position 5 (400) are either commercially available or can be prepared by methods known to persons skilled in the art such as from aryl aldehydes and TOSMIC (toluenesulfonylmethyl isocyanide; F. Besselièvre, F. Mahuteau-Betzer, D. S. Grierson, S. Piguel, *J. Org. Chem.* 2008, 73, 3278) in the presence of a base such as potassium carbonate and a solvent like methanol or by direct regioselective palladium(0)-catalyzed arylation of oxazole in the presence of a base such as potassium carbonate, pivalic acid, a phosphine ligand like 3,4,5,6-tetramethyl-tert-Bu-X-Phos in a polar solvent such as dimethyl acetamide or dimethyl formamide (N. A. Strotman, H. R. Chobanian, Y. Guo, J. He, J. E. Wilson, *Org. Lett.* 2010, 12, 3578). The Kondrat'eva reaction can be conducted under batch conditions (i.e. using microwave heating) or more preferably under continuous flow conditions, particularly due to the high volatility (i.e. low boiling point) of alkenes of general structure 401. Preferably the reaction is conducted in an apolar solvent such as toluene, chlorobenzene or trifluoromethyl benzene and in a temperature range between 150° C. and 200° C., more preferably between 200° C. and 280° C., and in the presence of an acid such as trifluoro-acetic acid. Annulated pyridines 402 can be oxidized under mild conditions in the benzylic position to the desired ketones 101f with tert-butyl hydroperoxide (TBHP) as an oxidizing agent and a mixed-valent dirhodium(II, III) tetrakis caprolactamate catalyst (preparation of catalyst described in: M. P. Doyle, L. J. Westrum, W. N. E. Wolthuis, M. M. See, W. P. Boone, V. Bagheri, M. M. Pearson, *J. Am. Chem. Soc.* 1993, 115, 958) in the presence of a base such as sodium bicarbonate (A. J. Catino, J. M. Nichols, H. Choi, S. Gottipamula, M. P. Doyle, *Org. Lett.* 2005, 7, 5167). Ketones 101f are then transformed to the corresponding intermediate amines using methods already described in Scheme 2a (step o) and finally converted to the target compounds of formula (I) such as annulated pyridine amides and sulfonamides according to the procedures outlined in Scheme 2d (step a and b).

Scheme 3e

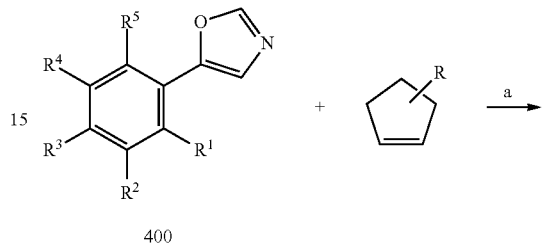

400

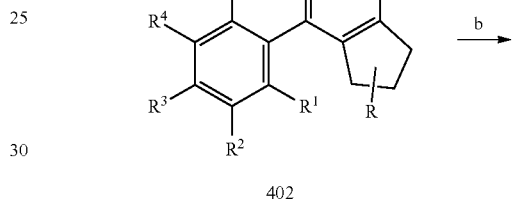

402

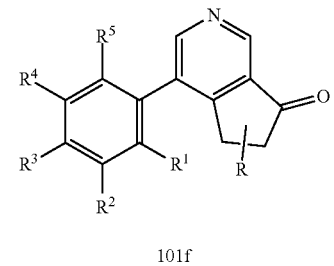

101f

Also an embodiment of the present invention is a process to prepare a compound of formula (I) as defined above comprising the reaction of a compound of formula (II) in the presence of a compound of formula (III);

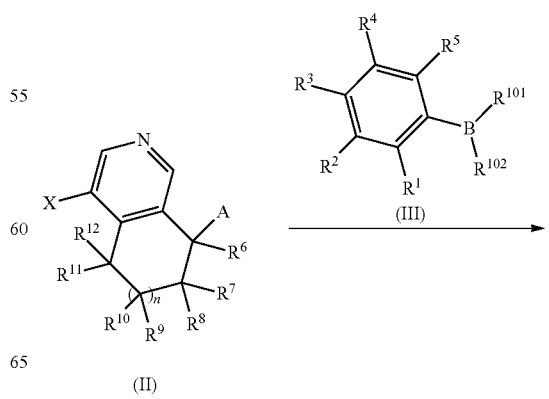

(II)

-continued

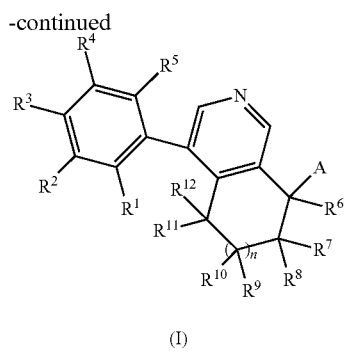

(I)

wherein $R^1$, $R^2$, $R^3$, $R^4$, $R^5$, $R^6$, $R^7$, $R^8$, $R^9$, $R^{10}$, $R^{11}$, $R^{12}$, A and n are as defined above, R101 and R102 are independently selected from alkyl and cycloalkyl, or $R^{101}$ and $R^{102}$ together with the boron atom to which they are attached form a borolane and X is halogen or triflate.

In particular, in a solvent, such as dimethylsulfoxide, toluene, ethanol, dioxane, tetrahydrofuran or N,N-dimethylformamide, optionally with water, particularly ethanol or DMF, in the presence of catalysts, such as tri-o-tolylphosphine/palladium(II)acetate, tetrakis-(triphenylphosphine)-palladium, bis(triphenylphosphine)palladium(II)chloride or dichloro[1,1'-bis(diphenylphosphino)-ferrocene]palladium (II), particularly tetrakis-(triphenylphosphine)-palladium or bis(triphenylphosphine)palladium(II)chloride, in the presence of a base, such as aqueous or non-aqueous potassium phosphate, sodium or potassium carbonate, particularly aqueous sodium carbonate, in an inert atmosphere such as argon or nitrogen, in a temperature range preferably between RT and reflux, particularly between RT and 130° C.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

The present invention also relates to the use of a compound according to formula (I) as described herein for the treatment or prophylaxis of chronic kidney disease, congestive heart failure, hypertension, primary aldosteronism and Cushing syndrome.

The present invention also relates to the use of a compound according to formula (I) as described herein for the treatment or prophylaxis of chronic kidney disease.

The present invention also relates to the use of a compound according to formula (I) as described herein for the treatment or prophylaxis of congestive heart failure.

The present invention also relates to the use of a compound according to formula (I) as described herein for the treatment or prophylaxis of hypertension.

The present invention also relates to the use of a compound according to formula (I) as described herein for the treatment or prophylaxis of primary aldosteronism.

A particular embodiment of the present invention is a compound according to formula (I) as described herein for the treatment or prophylaxis of chronic kidney disease, congestive heart failure, hypertension, primary aldosteronism and Cushing syndrome.

Also a particular embodiment of the present invention is a compound according to formula (I) as described herein for the treatment or prophylaxis of chronic kidney disease.

Also a particular embodiment of the present invention is a compound according to formula (I) as described herein for the treatment or prophylaxis of congestive heart failure.

Also a particular embodiment of the present invention is a compound according to formula (I) as described herein for the treatment or prophylaxis of hypertension.

Also a particular embodiment of the present invention is a compound according to formula (I) as described herein for the treatment or prophylaxis of primary aldosteronism.

The present invention also relates to the use of a compound according to formula (I) as described herein for the preparation of a medicament for the treatment or prophylaxis of chronic kidney disease, congestive heart failure, hypertension, primary aldosteronism and Cushing syndrome.

Also an embodiment of the present invention is the use of a compound according to formula (I) as described herein for the preparation of a medicament for the treatment or prophylaxis of chronic kidney disease.

Also an embodiment of the present invention is the use of a compound according to formula (I) as described herein for the preparation of a medicament for the treatment or prophylaxis of congestive heart failure.

Also an embodiment of the present invention is the use of a compound according to formula (I) as described herein for the preparation of a medicament for the treatment or prophylaxis of hypertension.

Also an embodiment of the present invention is the use of a compound according to formula (I) as described herein for the preparation of a medicament for the treatment or prophylaxis of primary aldosteronism.

Also an object of the invention is a method for the treatment or prophylaxis of chronic kidney disease, congestive heart failure, hypertension, primary aldosteronism and Cushing syndrome, which method comprises administering an effective amount of a compound according to formula (I) as described herein.

Also an embodiment of the present invention is a method for the treatment or prophylaxis of chronic kidney disease, which method comprises administering an effective amount of a compound according to formula (I) as described herein.

Also an embodiment of the present invention is a method for the treatment or prophylaxis of congestive heart failure, which method comprises administering an effective amount of a compound according to formula (I) as described herein.

Also an embodiment of the present invention is a method for the treatment or prophylaxis of hypertension, which method comprises administering an effective amount of a compound according to formula (I) as described herein.

Also an embodiment of the present invention is a method for the treatment or prophylaxis of primary aldosteronism, which method comprises administering an effective amount of a compound according to formula (I) as described herein. formula (I) as described herein, when manufactured according to any one of the described processes.

Assay Procedures

Herein we identified the use of the G-402 cell line as a host cell to ectopically express (transiently or stably) enzymes of the CYP11 family. Specifically we developed stable G-402 cells expressing ectopically human CYP11B1, human CYP11B2, human CYP11A1, cynmolgus CYP11B1 or cynomolgus CYP11B2 enzyme activity. Importantly the identified cell line G-402 expresses co-factors (adrenodoxin and adrenodoxin reductase) important for the activity of the CYP11 family and no relevant enzyme activity of the CYP11 family (in comparison to H295R cells) was detected in these cells. Therefore the G-402 cell line is uniquely suited as a host cell for the ectopic expression of enzymes from the CYP11 family.

G-402 cells can be obtained from ATCC(CRL-1440) and were originally derived from a renal leiomyoblastoma.

The expression plasmids contains the ORF for either human/cyno CYP11B1 or CYP11B2 under the control of a suitable promoter (CMV-promoter) and a suitable resistance marker (neomycin). Using standard techniques the expression plasmid is transfected into G-402 cells and these cells are then selected for expressing the given resistance markers. Individual cell-clones are then selected and assessed for displaying the desired enzymatic activity using 11-Deoxycorticosterone (Cyp 11B2) or 11-Deoxycortisol (Cyp 11B1) as a substrate.

G-402 cells expressing CYP11 constructs were established as described above and maintained in McCoy's 5a Medium Modified, ATCC Catalog No. 30-2007 containing 10% FCS and 400 μg/ml G418 (Geneticin) at 37° C. under an atmosphere of 5% CO2/95% air. Cellular enzyme assays were performed in DMEM/F12 medium containing 2.5% charcoal treated FCS and appropriate concentration of substrate (0.3-10 uM 11-Deoxycorticosterone, 11-Deoxycortisol or Corticosterone). For assaying enzymatic activity, cells were plated onto 96 well plates and incubated for 16 h. An aliquot of the supernatant is then transferred and analyzed for the concentration of the expected product (Aldosterone for CYP11B2; Cortisol for CYP11B1). The concentrations of these steroids can be determined using HTRF assays from CisBio analyzing either Aldosterone or Cortisol.

Inhibition of the release of produced steroids can be used as a measure of the respective enzyme inhibition by test compounds added during the cellular enzyme assay. The dose dependent inhibition of enzymatic activity by a compound is calculated by means of plotting added inhibitor concentrations (x-axes) vs. measured steroid/product level (y-axes). The inhibition is then calculated by fitting the following 4-parameter sigmoidal function (Morgan-Mercer-Flodin (MMF) model) to the raw data points using the least squares method:

$$y = \frac{AB + Cx^D}{B + x^D}$$

wherein, A is the maximum y value, B is the EC50 factor determined using XLFit, C is the minimum y value and D is the slope value.

The maximum value A corresponds to the amount of steroid produced in the absence of an inhibitor, the value C corresponds to the amount of steroid detected when the enzyme is fully inhibited.

EC50 values for compounds claimed herein were tested with the G402-based assay system described. Cyp 11B2 enzyme activity was tested in presence of 1 μM Deoxycorticosterone and variable amounts of inhibitors; Cyp 11B1 enzyme activity was tested in presence of 1 μM Deoxycortisol and variable amounts of inhibitors.

| Example | EC50 human CYP11B1 μM | EC50 human CYP11B2 μM |
| --- | --- | --- |
| 1 | 0.173 | 0.042 |
| 2 | 1.094 | 0.207 |
| 3 | 0.291 | 0.052 |

-continued

| Example | EC50 human CYP11B1 μM | EC50 human CYP11B2 μM |
| --- | --- | --- |
| 4 | 2.173 | 0.220 |
| 5 | 0.760 | 0.025 |
| 6 | 11.711 | 0.942 |
| 7 | 0.263 | 0.010 |
| 8 | 0.422 | 0.043 |
| 9 | 4.187 | 0.123 |
| 10 | 0.658 | 0.067 |
| 11 | 0.031 | 0.008 |
| 12 | 0.030 | 0.025 |
| 13 | 0.008 | 0.010 |
| 14 | 0.073 | 0.016 |
| 15 | 0.021 | 0.005 |
| 16 | 0.488 | 0.072 |
| 17 | 0.511 | 0.022 |
| 18 | 7.220 | 0.879 |
| 19 | 0.174 | 0.012 |
| 20 | 0.480 | 0.024 |
| 21 | 7.089 | 0.082 |
| 22 |  | 6.377 |
| 23 | 3.691 | 0.031 |
| 24 | 1.423 | 0.031 |
| 25 | 23.123 | 0.467 |
| 26 | 0.503 | 0.017 |
| 27 | 0.625 | 0.014 |
| 28 | 30.396 | 0.226 |
| 29 | 0.241 | 0.004 |
| 30 | 1.503 | 0.028 |
| 31 |  | 1.224 |
| 32 | 0.617 | 0.019 |
| 33 | 14.732 | 0.159 |
| 34 | 42.446 | 4.489 |
| 35 | 6.681 | 0.071 |
| 36 | 1.013 | 0.014 |
| 37 | 31.356 | 1.260 |
| 38 | 0.214 | 0.007 |
| 39 | 3.236 | 0.029 |
| 40 | 32.542 | 4.848 |
| 41 | 1.813 | 0.016 |
| 42 | 2.397 | 0.109 |
| 43 | 1.148 | 0.027 |
| 44 | 0.826 | 0.047 |
| 45 | 0.177 | 0.003 |
| 46 | 3.758 | 0.160 |
| 47 |  | 5.751 |
| 48 | 2.098 | 0.079 |
| 49 | 4.044 | 0.079 |
| 50 |  | 5.773 |
| 51 | 2.255 | 0.025 |
| 52 | 3.710 | 0.203 |
| 53 |  | 9.100 |
| 54 | 3.171 | 0.089 |
| 55 | 0.184 | 0.012 |
| 56 | 38.266 | 3.209 |
| 57 | 0.103 | 0.007 |
| 58 | 0.156 | 0.010 |
| 59 |  | 1.656 |
| 60 | 0.064 | 0.002 |
| 61 | 3.607 | 0.044 |
| 62 | 14.651 | 1.677 |
| 63 | 1.718 | 0.030 |
| 64 | 12.692 | 0.730 |
| 65 | 1.080 | 1.630 |
| 66 | 14.200 | 0.280 |
| 67 | 8.469 | 0.764 |
| 68 | 10.690 | 0.658 |
| 69 | 0.742 | 0.011 |
| 70 | 3.030 | 0.042 |
| 71 | 3.023 | 0.242 |
| 72 |  | 16.4788 |
| 73 | 1.866 | 0.0444 |
| 74 | 1.225 | 0.0328 |
| 75 | 3.543 | 0.0512 |
| 76 | 23.199 | 0.1185 |
| 77 | 2.243 | 0.0588 |

-continued

| Example | EC50 human CYP11B1 μM | EC50 human CYP11B2 μM |
|---|---|---|
| 78 | 0.276 | 0.0233 |
| 79 | 1.777 | 0.0356 |
| 80 | 0.427 | 0.0045 |
| 81 | 0.012 | 0.0013 |
| 82 | 0.071 | 0.0052 |
| 83 | 0.740 | 0.0169 |
| 84 | 0.005 | 0.0048 |
| 85 | 2.701 | 0.0152 |
| 86 | 1.638 | 0.0304 |
| 87 | 0.028 | 0.0022 |
| 88 | 0.627 | 0.0121 |
| 89 | 1.3787 | 0.0547 |
| 90 | 1.9026 | 0.0267 |
| 91 | 0.3893 | 0.3007 |
| 92 | 0.4405 | 0.0164 |
| 93 | 0.3637 | 0.0863 |
| 94 | 2.3284 | 0.1481 |
| 95 | 1.9619 | 1.8039 |
| 96 | 3.8704 | 0.3731 |
| 97 | 0.0724 | 0.0014 |
| 98 | 0.628 | 0.0196 |
| 99 | 1.1897 | 0.0659 |
| 100 | 0.4301 | 0.0129 |
| 101 | 1.2662 | 0.0269 |
| 102 | 0.040769 | 0.0011 |
| 103 | 0.0023 | 0.0002 |
| 104 | 0.7097 | 0.0146 |
| 105 | 1.6689 | 0.107 |
| 106 | 0.1589 | 0.0046 |
| 107 | 7.829043 | 0.964009 |
| 108 | 0.3036 | 0.0031 |
| 109 | 0.7915 | 0.0303 |

Compounds of formula (I) and their pharmaceutically acceptable salts or esters thereof as described herein have $EC_{50}$ (CYP11B2) values between 0.000001 uM and 1000 uM, particular compounds have $EC_{50}$ (CYP11B2) values between 0.00005 uM and 500 uM, further particular compounds have $EC_{50}$ (CYP11B2) values between 0.0005 uM and 50 uM, more particular compounds have $EC_{50}$ (CYP11B2) values between 0.0005 uM and 5 uM. These results have been obtained by using the described enzymatic assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of aldosterone mediated diseases.

The compounds of formula (I) or their pharmaceutically acceptable salts and esters herein display also variable inhibition of CYP11B1. These compounds may be used for the inhibition of CYP11B1 in combination with variable inhibition of CYP11B2. Such compounds may be used for treatment or prophylaxis of conditions displaying excessive cortisol production/levels or both excessive cortisol and aldosterone levels (for ex. Cushing syndrome, burn trauma patients, depression, post-traumatic stress disorders, chronic stress, corticotrophic adenomas, Morbus Cushing).

In accordance with the invention, the compounds of formula (I) or their pharmaceutically acceptable salts and esters can be used for the treatment or prophylaxis of cardiovascular conditions (including hypertension and heart failure), renal conditions, liver conditions, vascular conditions, inflammatory conditions, pain, retinopathy, neuropathy (such as peripheral neuropathy), insulinopathy, edema, endothelial dysfunction, baroreceptor dysfunction; fibrotic diseases, depression and the like.

Cardiovascular conditions include congestive heart failure, coronary heart disease, arrhythmia, arterial fibrillation, cardiac lesions, decreased ejection fraction, diastolic and systolic heart dysfunction, fibrinoid necrosis of coronary arteries, heart failure, hypertrophic cardiomyopathy, impaired arterial compliance, impaired diastolic filling, ischemia, left ventricular hypertrophy, myocardial and vascular fibrosis, myocardial infarction, myocardial necrotic lesions, myocardial necrotic lesions cardiac arrhythmias, prevention of sudden cardiac death, restenosis, stroke, vascular damage.

Renal conditions include acute and chronic renal failure, end-stage renal disease, decreased creatinine clearance, decreased glomerular filtration rate, diabetic nephropathy, expansion of reticulated mesangial matrix with or without significant hypercellularity, focal thrombosis of glomerular capillaries, global fibrinoid necrosis, glomerulosclerosis, ischemic lesions, malignant nephrosclerosis (such as ischemic retraction, microalbuminuria, nephropathy, proteinuria, reduced renal blood flow, renal arteriopathy, swelling and proliferation of intracapillary (endothelial and mesangial) and/or extracapillary cells (crescents).

Liver conditions include, but are not limited to, liver cirrhosis, liver ascites, hepatic congestion, nonalcoholic steatohepatitis and the like.

Vascular conditions include, but are not limited to, thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction, and the like.

Inflammatory conditions include, but are not limited to, arthritis (for example, osteoarthritis), inflammatory airways diseases (for example, chronic obstructive pulmonary disease (COPD)), and the like.

Pain includes, but is not limited to, acute pain, chronic pain (for example, arthralgia), and the like.

Edema includes, but is not limited to, peripheral tissue edema, hepatic congestion, splenic congestion, liver ascites, respiratory or lung congestion, and the like.

Insulinopathies include, but are not limited to, insulin resistance, Type I diabetes mellitus, Type II diabetes mellitus, glucose sensitivity, pre-diabetic state, syndrome X, and the like.

Fibrotic diseases include, but are not limited to myocardial and intrarenal fibrosis, renal interstitial fibrosis and liver fibrosis.

Furthermore, the compounds of formula (I) or their pharmaceutically acceptable salts and esters as described herein can also be used for the treatment or prophylaxis of cardiovascular condition selected from the group consisting of hypertension, heart failure (particularly heart failure post myocardial infarction), left ventricular hypertrophy, and stroke.

In another embodiment, the cardiovascular condition is hypertension.

In another embodiment, the cardiovascular condition is heart failure.

In another embodiment, the cardiovascular condition is left ventricular hypertrophy.

In another embodiment, the cardiovascular condition is stroke.

In another embodiment, the compounds of formula (I) or their pharmaceutically acceptable salts and esters can be used for the treatment or prophylaxis renal condition.

In another embodiment, the renal condition is nephropathy.

In another embodiment, the compounds of formula (I) or their pharmaceutically acceptable salts and esters can be used for the treatment or prophylaxis Type II diabetes mellitus In another embodiment, the compounds of formula (I) or their pharmaceutically acceptable salts and esters can be used for the treatment or prophylaxis Type I diabetes mellitus The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

All examples and intermediates were prepared under argon atmosphere if not specified otherwise.

Intermediate A-1

(rac)-N-(4-Bromo-5,6,7,8-tetrahydroisoquinolin-8-yl)propionamide

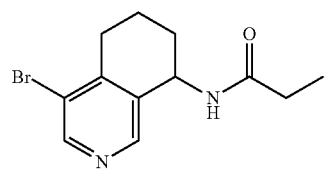 [SMILES: CCC(=O)NC1CCCc2c(Br)cncc21]

[A] Ethyl 5-bromo-4-methylnicotinate

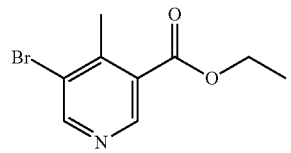

To a stirred light brown suspension of 5-bromo-4-methylnicotinic acid (10.00 g, 46.3 mmol) and ethanol (2.35 g, 2.97 mL, 50.9 mmol) in $CH_2Cl_2$ (231 mL) at 0° C. under Argon was added EDCI (10.9 g, 55.5 mmol) and DMAP (566 mg, 4.63 mmol), stirring was continued over night and the reaction mixture was allowed to warm up to RT. The reaction mixture was poured on aq. 10% $KH_2PO_4$ solution followed by extraction with AcOEt (3×). The organic phases were washed once with aq. 10% $KH_2PO_4$, aq. sat. $NaHCO_3$ and with aq. sat. NaCl solution. The combined organic phases were dried ($Na_2SO_4$), filtered and evaporated to afford the title compound (9.49 g, 84%) as brown solid. MS: 244.0 (M+H⁺, 1 Br).

[B] Methyl 4-bromo-8-oxo-5,6,7,8-tetrahydroisoquinoline-7-carboxylate

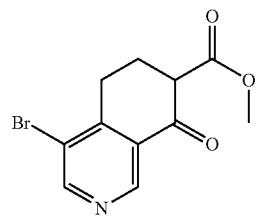 [SMILES: COC(=O)C1CCc2c(Br)cncc2C1=O]

Ethyl 5-bromo-4-methylnicotinate (7.04 g, 28.8 mmol) in THF (28.8 mL) was added over a period of 20 min to a solution of LDA (31.7 mmol) [generated from N,N-diisopropylamine (4.52 mL, 31.7 mmol) and n-butyllithium (19.8 mL, 31.7 mmol, 1.6M in hexane) in THF (144 mL)] at −78° C. The resulting dark red solution was stirred for 20 min, then methyl acrylate (6.5 mL, 72.1 mmol) in THF (28.8 mL) was added over 15 min. The reaction was stirred an additional 1.5 h, then aq. 10% AcOH (57.8 mL, 101 mmol) was added (pH 4-5) and the reaction was allowed to warm to room temperature. After evaporation, the residue was partitioned between aq. sat. NaHCO$_3$ and EtOAc and extracted with EtOAc (3×). The combined organic layers were dried (Na$_2$SO$_4$) and concentrated to afford the title compound (7.80 g, 95% in 70% purity with 30% starting material) as brown solid. MS: 280.0 (M+H$^+$, 1 Br).

[C] 4-Bromo-6,7-dihydroisoquinolin-8(5H)-one

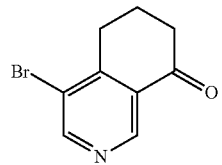

The crude methyl 4-bromo-8-oxo-5,6,7,8-tetrahydroisoquinoline-7-carboxylate (7.79 g, 27.4 mmol) was dissolved (small amount of not dissolved material) in aq. 6M HCl (84.1 mL, 505 mmol) and heated at reflux for 2.5 h (dark brown solution, no more SM visible on TLC). The acidic solution was concentrated in vacuo, suspended in water (ca. 25 mL), cooled in ice, and basified with 6.0 M KOH. The aqueous solution was washed with Et$_2$O (2×) and CH$_2$Cl$_2$ (3×), the combined organic layers were dried over Na$_2$SO$_4$, filtered and concentrated to afford after high vacuum drying the title compound (4.30 g, 69%) as brown solid. MS: 226.0 (M+H$^+$, 1 Br).

[D] (rac)-4-Bromo-5,6,7,8-tetrahydroisoquinolin-8-amine

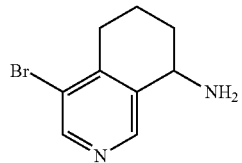 [SMILES: NC1CCCc2c(Br)cncc21]

4-Bromo-6,7-dihydroisoquinolin-8(5H)-one (4.81 g, 21.3 mmol), titanium (IV) isopropoxide (12.5 mL, 42.6 mmol) and ammonia, 2.0 M solution in MeOH (53.2 mL, 106 mmol) were stirred at RT for 5 h. The reaction was cooled to 0° C. and NaBH$_4$ (1.21 g, 31.9 mmol) was added portionwise over 10 min; the resulting mixture was stirred at RT for an additional 2 h. The reaction was quenched by pouring it into aq. ammonium hydroxide (25%), the precipitate was filtered and washed with EtOAc (3×, each time suspended in AcOEt and stirred for 5 min). The organic layer was separated and the remaining aqueous layer was extracted with EtOAc. The combined organic extracts were extracted with 1 M HCl. The acidic aqueous extracts were washed with ethyl acetate (1×), then treated with aqueous sodium hydroxide (2 M) to give pH 10-12, and extracted with EtOAc (3×). The combined second organic extracts were washed with brine, dried (Na$_2$SO$_4$), and concentrated in vacuo to afford the title compound (4.11 g, 85%) as brown solid. MS: 225 (M$^+$, 1 Br).

[E] (rac)-N-(4-bromo-5,6,7,8-tetrahydroisoquinolin-8-yl)propionamide

To a stirred black solution of (rac)-4-bromo-5,6,7,8-tetrahydroisoquinolin-8-amine (317 mg, 1.4 mmol) and propionic acid (115 µL, 1.54 mmol) in CH$_2$Cl$_2$ (7.0 mL) at 0° C. was added EDCI (295 mg, 1.54 mmol), stirring was continued over night and the reaction mixture was allowed to warm up to RT. The reaction mixture was poured on aq. 10% KH$_2$PO$_4$ solution followed by extraction with AcOEt (3×). The organic phases were washed once with aq. 10% KH$_2$PO$_4$, aq. sat. NaHCO$_3$ and with aq. sat. NaCl solution. The combined organic phases were dried over Na$_2$SO$_4$, filtered, evaporated and purified by precipitation CH$_2$Cl$_2$/n-pentane to afford the title compound (365 mg, 92%) as light brown solid. MS: 283.0 (M+H$^+$, 1 Br).

Intermediate A-2

(rac)-4-Bromo-5,6,7,8-tetrahydroisoquinolin-8-ol

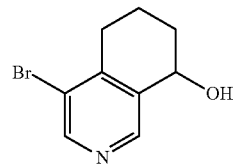 [SMILES: OC1CCCc2c(Br)cncc21]

A suspension of 4-bromo-6,7-dihydroisoquinolin-8(5H)-one (intermediate A-1[C]) (2.135 g, 9.44 mmol) in MeOH (18.9 mL) was cooled to 0° C. and treated with NaBH$_4$ (357 mg, 9.44 mmol) in 5 portions over 30 min. The reaction was stirred for ¾ h at 0° C., then AcOH was added dropwise until pH ~5-6 and the reaction mixture was evaporated. The residue was diluted with water and poured on aq. sat. NaHCO$_3$-solution followed by extraction with EtOAc (3×). The organic layers are washed once with aq. sat. NaHCO$_3$ and aq. 10% NaCl solution, dried over Na$_2$SO$_4$ and concentrated in vacuo. The residue was precipitated with CH$_2$Cl$_2$/n-pentane to afford the title compound (1.98 g, 92%) as dark brown viscous oil. MS: 227 (M$^+$, 1 Br).

Intermediate A-3

(rac)-4-Bromo-8-(3,4-dimethylphenyl)-5,6,7,8-tetrahydroisoquinolin-8-ol

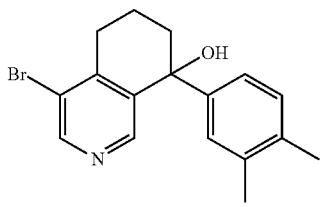 [SMILES: Cc1ccc(C2(O)CCCc3c(Br)cncc32)cc1C]

A solution of 4-bromo-1,2-dimethylbenzene (78.6 mg, 425 μmol) in THF (1.3 mL) was cooled (−78° C.) and treated with n-BuLi (1.6 M in n-hexane, 265 μL, 425 μmol). After 15 min a solution of 4-bromo-6,7-dihydroisoquinolin-8(5H)-one (intermediate A-1[C]) (80 mg, 354 μmol) in THF (1.3 mL) was added and after 1 h the brown suspension was warmed up 0° C. The mixture was poured on aq. sat. NH$_4$Cl-solution and extracted with EtOAc (3×). The organic layers were washed with aq. sat. NaHCO$_3$ and aq. sat. NaCl solution, dried over Na$_2$SO$_4$ and concentrated in vacuo. Purification by flash chromatography (50 g SiO$_2$, Telos-cartridge, CH$_2$Cl$_2$/MeOH (1 to 2%)) gave the title compound (75 mg, 64%) as off-white foam. MS: 332.1 (M+H$^+$, 1 Br).

Intermediate A-4

(rac)-N-(4-Bromo-6,7-dihydro-5H-cyclopenta[c]pyridin-7-yl)propionamide

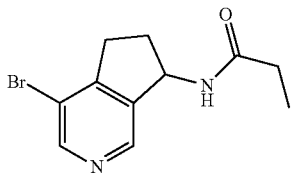

[A] Lithium 4-bromo-6-(methoxycarbonyl)-5H-cyclopenta[c]pyridin-7-olate

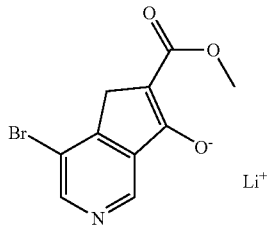

Ethyl 5-bromonicotinate (5 g, 21.7 mmol) in THF (22 mL) was added over a period of 20 min to a solution of LDA (23.9 mmol) [generated from N,N-diisopropylamine (3.41 mL, 23.9 mmol) and n-butyllithium (14.9 mL, 23.9 mmol, 1.6M in hexane) in THF (95 mL)] at −78° C. The resulting dark red solution was stirred for 30 min, then methyl acrylate (4.9 mL, 54.3 mmol) in THF (22 mL) was added over 15 min. The reaction was stirred an additional 1.5 h, then aq. 10% AcOH (43.5 mL, 76.1 mmol) was added (giving a pH of 4-5) and the reaction was allowed to warm to room temperature. Evaporation under reduced pressure afforded the title compound (in 50% purity, determined by $^1$H-NMR) as dark green amorphous solid. MS: 270.0 (M+H$^+$, 1 Br).

[B] 4-Bromo-5H-cyclopenta[c]pyridin-7(6H)-one

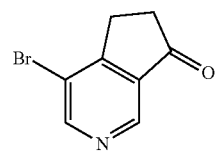

The crude sodium 4-bromo-6-(methoxycarbonyl)-5H-cyclopenta[c]pyridin-7-olate (20.0 mmol) was dissolved in aq. 6 M HCl, (54 mL) and heated at reflux for 1.5 h. The acidic solution was cooled in ice, poured into Et$_2$O, basified with aq. 6 M KOH (to give a pH of −9) and extracted with Et$_2$O (2×). The Et$_2$O phases were collected, dried over Na$_2$SO$_4$, concentrated and purified by flash chromatography (20 g SiO$_2$, i-PrOH (1%)/CH$_2$Cl$_2$) to afford after trituration with a small amount of Et$_2$O the title compound (0.69 g, 16% over 2 steps) as pink solid. MS: 212.0 (M+H$^-$, 1 Br).

[C] (rac)-4-Bromo-6,7-dihydro-5H-cyclopenta[c]pyridin-7-amine and [C2](rac)-4-Bromo-6,7-dihydro-5H-cyclopenta[c]pyridin-7-ol Intermediate A-4 [C]

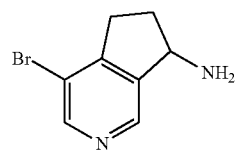

Intermediate A-4 [C2]

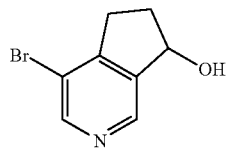

4-Bromo-5H-cyclopenta[c]pyridin-7(6H)-one (1.01 g, 4.76 mmol), titanium (IV) isopropoxide (2.79 mL, 9.53 mmol) and ammonia, 2M solution in MeOH (11.9 mL, 23.8 mmol) were stirred at RT for 5 h. The reaction mixture was cooled to 0° C. and NaBH$_4$ (270 mg, 7.14 mmol) was added in three portions over 20 min; the resulting mixture was stirred at RT for an additional 1.5 h. The reaction was quenched by pouring it into ammonium hydroxide (25%) (24.8 mL, pH 9-10), the precipitate was filtered and washed with AcOEt (3×, each time suspended in AcOEt and stirred for 5 min). The organic layer was separated and the remaining aqueous layer was extracted with EtOAc. The combined organic extracts were extracted with aq. 1 M HCl. The acidic aqueous extracts were washed with EtOAc (1×), then treated with aq. sodium hydroxide (2 M) to give a pH of 10-12, and extracted with EtOAc (3×). The combined second organic extracts were washed with brine, dried (Na₂SO₄) and concentrated in vacuo to afford the title compound (530 mg, 52% yield in 70% purity, determined by $^1$H-NMR) of (rac)-4-bromo-6,7-dihydro-5H-cyclopenta[c]pyridin-7-amine (Intermediate A-4 [C]) as dark green amorphous solid. MS: 213.0 (M+H⁺, 1 Br).

The acidic EtOAc-wash was evaporated and purified by flash chromatography (SiO₂, Telos-cartridge, CH₂Cl₂/2-propanol (2.5 to 20%)) to afford and 116 mg (11% yield in 88% purity, determined by $^1$H-NMR) of (rac)-4-bromo-6,7-dihydro-5H-cyclopenta[c]pyridin-7-ol (Intermediate A-4 [C2]) as black solid. MS: 215.0 (M+H⁺, 1 Br).

[D] (rac)-N-(4-Bromo-6,7-dihydro-5H-cyclopenta[c]pyridin-7-yl)propionamide

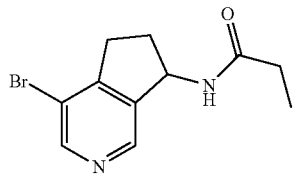

To a stirred black solution of (rac)-4-bromo-6,7-dihydro-5H-cyclopenta[c]pyridin-7-amine (intermediate A-4 [C]) (213 mg, 1 mmol) and propionic acid (82.1 µL, 1.1 mmol) in CH₂Cl₂ (5.0 mL) at 0° C. was added EDCI (230 mg, 1.2 mmol), stirring was continued over night and the reaction mixture was allowed to warm up to RT. The reaction mixture was poured on aq. 10% KH₂PO₄ solution followed by extraction with AcOEt (3×). The organic phases were washed once with aq. 10% KH₂PO₄, aq. sat. NaHCO₃ and aq. sat. NaCl solution. The combined organic phases were dried over Na₂SO₄, filtered, evaporated and purified by flash chromatography (75 g SiO₂, Telos-cartridge, CH₂Cl₂/MeOH (2%)) to afford the title compound (105 mg, 39%) as a dark grey solid. MS: 269.0 (M+H⁺, 1 Br).

Intermediate A-5

(R)—N—((R,S)-4-Bromo-5,6,7,8-tetrahydro-isoquinolin-8-yl)-2-hydroxy-propionamide

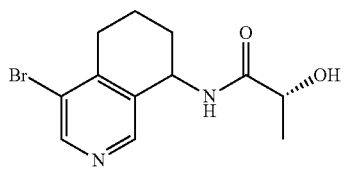 [SMILES: C[C@@H](O)C(=O)NC1CCCc2c(Br)cncc21]

To a stirred yellow solution of (rac)-4-bromo-5,6,7,8-tetrahydroisoquinolin-8-amine (intermediate A-1[D]) (182.0 mg, 0.80 mmol), 1-hydroxylbenzotriazol.monohydrate (138.0 mg, 0.88 mmol), (R)-2-hydroxypropanoic acid (86.5 mg, 0.96 mmol) and N,N-diisopropylethylamine (0.168 mL, 0.96 mmol) in CH₂Cl₂ (6.4 mL) at 0° C. under Argon was added EDCI (184.0 mg, 0.96 mmol). Stirring was continued over night and the reaction mixture was allowed to warm up to room temperature. The reaction mixture was poured into aq. 10% KH₂PO₄ solution followed by extraction with AcOEt (3×). The organic phases were washed once with aq. 10% KH₂PO₄, aq. sat. NaHCO₃ and with aq. sat. NaCl solution; the combined organic phases were dried over Na₂SO₄, filtered, evaporated and precipitated from CH₂Cl₂/Et₂O to give the title compound (183 mg, 77%) as a light yellow powder. MS: 299.0 (M+H⁺, 1 Br).

Intermediate A-6

(R)—N—((R,S)-4-Bromo-6,7-dihydro-5H-[2]pyridin-7-yl)-2-hydroxy-propionamide

In analogy to the procedure described for the preparation for intermediate A5, (rac)-4-bromo-6,7-dihydro-5H-cyclopenta[c]pyridin-7-amine (intermediate A-4 [C]) and (R)-2-hydroxypropanoic acid gave after flash chromatography (SiO₂, Telos-cartridge, CH₂Cl₂/MeOH (2.5 to 3%)) the title compound as dark green solid in 29% yield. MS: 285.0 (M+H⁺, 1 Br).

Intermediate A-7

(rac)-N-(4-Bromo-6,7-dihydro-5H-cyclopenta[c]pyridin-7-yl)ethanesulfonamide

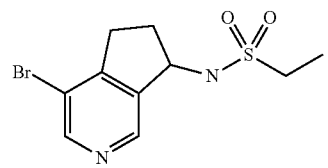 [SMILES: CCS(=O)(=O)NC1CCc2c(Br)cncc21]

In analogy to the procedure described for the preparation of example 2, (rac)-4-bromo-6,7-dihydro-5H-cyclopenta[c]pyridin-7-amine (intermediate A-4 [C]) and ethanesulfonyl chloride gave the title compound as a grey solid in 94% yield. MS: 304.99 (M+H⁺, 1 Br).

Intermediate A-8

(all rac)-N-(4-Bromo-7-methyl-5,6,7,8-tetrahydro-isoquinolin-8-yl)-propionamide

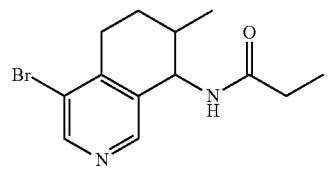 [SMILES: CCC(=O)NC1c2cncc(Br)c2CCC1C]

[A] (rac)-4-Bromo-7-methyl-8-oxo-5,6,7,8-tetrahydro-isoquinoline-7-carboxylic acid methyl ester

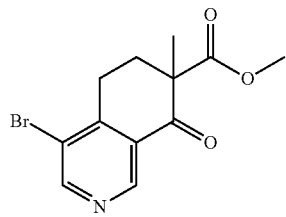 [SMILES: COC(=O)C1(C)CCc2c(Br)cncc2C1=O]

To a stirred solution of (rac)-methyl 4-bromo-8-oxo-5,6,7,8-tetrahydroisoquinoline-7-carboxylate (3.5 g, 12.3 mmol) (intermediate A-1[B]) in DMF (10 mL) and THF (50 mL) was added 60% NaH (750 mg, 18.5 mmol) in portions at 0° C. The reaction mixture was stirred at 0° C. for 15 min before methyl iodide (1.6 mL, 24.6 mmol) was added and the resulting reaction mixture was allowed to warm up to room temperature and stirred over night. The reaction mixture was then diluted with water (10 mL) and extracted with EtOAc (2×). Combined organics were washed with brine, dried over $Na_2SO_4$, filtered and evaporated to dryness. The residue was purified by silica gel flash chromatography eluting with a 0 to 30% EtOAc-heptane gradient to give the title compound (3.3 g, 90% yield) as a light yellow solid. MS: 297.9 & 299.9 $(M+H)^+$.

[B] (rac)-4-Bromo-7-methyl-6,7-dihydro-5H-isoquinolin-8-one

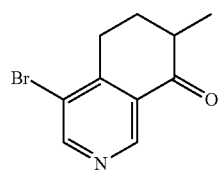

(rac)-4-Bromo-7-methyl-8-oxo-5,6,7,8-tetrahydro-isoquinoline-7-carboxylic acid methyl ester (3.3 g, 11.0 mmol) was dissolved in aq. 6 N HCl (28.0 mL, 168 mmol) and heated at reflux for 2.5 h. The acidic solution was concentrated in vacuo, re-suspended in water (ca. 25 mL), cooled in an ice-water bath, and basified with 6 N aq. KOH solution. The aqueous solution was then washed with $Et_2O$ (2×) and $CH_2Cl_2$ (3×). The combined organic layers were dried over $Na_2SO_4$, filtered and concentrated in vacuo to afford the title compound (2.38 g, 90% yield) as a brown solid. MS: 240.1 & 242.1 $(M+H)^+$.

[C] (all rac)-4-Bromo-7-methyl-5,6,7,8-tetrahydro-isoquinolin-8-ylamine

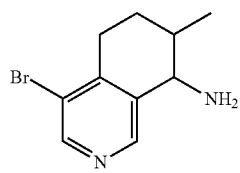

A mixture of (rac)-4-bromo-7-methyl-6,7-dihydro-5H-isoquinolin-8-one (2.2 g, 9.2 mmol), $NaBH_3CN$ (864 mg, 13.8 mmol) and $CH_3COONH_4$ (7.1 g, 92 mmol) in isopropanol (20 mL) was refluxed for 3 hr. Afterwards, the solution was cooled to room temperature; it was then concentrated in vacuo to afford a yellow oil, which was extracted with water/EtOAc (2×). Combined organics were washed with brine, dried over $Na_2SO_4$, filtered and concentrated in vacuo to afford the title compound (1.77 g, 80% yield) as a brown solid. MS: 241.1 & 243.1 $(M+H)^+$.

[D] (all rac)-N-(4-Bromo-7-methyl-5,6,7,8-tetrahydro-isoquinolin-8-yl)-propionamide

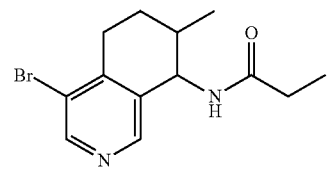 [SMILES: CCC(=O)NC1c2cncc(Br)c2CCC1C]

To a stirred solution of (all rac)-4-bromo-7-methyl-5,6,7,8-tetrahydro-isoquinolin-8-ylamine (1.7 g, 7.1 mmol) and $Et_3N$ (1.0 mL) in $CH_2Cl_2$ (20 mL) was added propionyl chloride (0.74 mL, 8.52 mmol) at 0° C. and the mixture was stirred for 1 h. It was then extracted with water/EtOAc (2×) and combined organics were washed with brine, dried over $Na_2SO_4$, filtered and concentrated in vacuo. The residue was purified by silica gel flash chromatography eluting with a 0 to 30% EtOAc-heptane gradient to give the title compound (1.2 g, 57% yield) as a light yellow solid. MS: 297.1 & 299.1 $(M+H)^+$.

Intermediate A-9a

N-((7R,8S or 7S,8R)-4-Bromo-7-methyl-5,6,7,8-tetrahydro-isoquinolin-8-yl)-propionamide

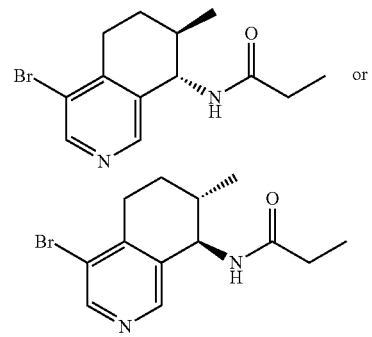

Intermediate A-9b

N-((7S,8S or 7R,8R)-4-Bromo-7-methyl-5,6,7,8-tetrahydro-isoquinolin-8-yl)-propionamide

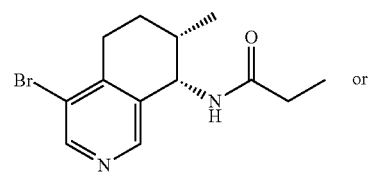

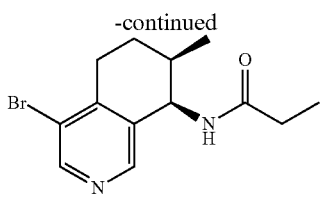

Intermediate A-9c

N-((7S,8R or 7R,8S)-4-Bromo-7-methyl-5,6,7,8-tetrahydro-isoquinolin-8-yl)-propionamide

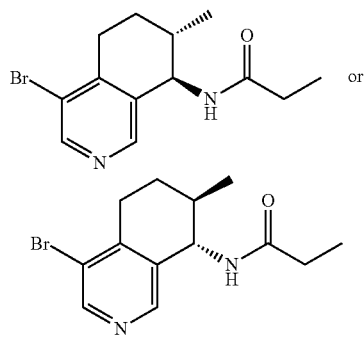

Intermediate A-9d

N-((7R,8R or 7S,8S)-4-Bromo-7-methyl-5,6,7,8-tetrahydro-isoquinolin-8-yl)-propionamide

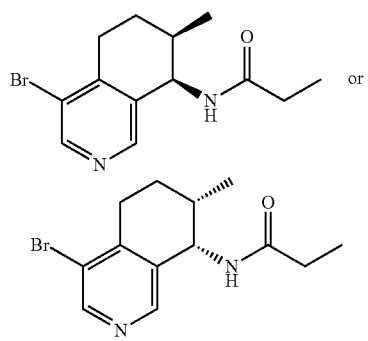

The title intermediates were prepared by chiral separation of (all rac)-N-(4-bromo-7-methyl-5,6,7,8-tetrahydro-isoquinolin-8-yl)-propionamide (intermediate A-8, 1.2 g) on a Chiralpak AD column (40% ethanol in n-hexane) to give 34% of N-((7R,8S or 7S,8R)-4-bromo-7-methyl-5,6,7,8-tetrahydro-isoquinolin-8-yl)-propionamide (intermediate A-9a) as light yellow oil, MS: 297.1 & 299.1 (M+H$^+$) and 35% of N-((7S,8S or 7R,8R)-4-bromo-7-methyl-5,6,7,8-tetrahydro-isoquinolin-8-yl)-propionamide (intermediate A-9b) as off-white solid, MS: 297.1 & 299.1 (M+H$^+$) and 33% of N-((7S,8R or 7R,8S)-4-bromo-7-methyl-5,6,7,8-tetrahydro-isoquinolin-8-yl)-propionamide (intermediate A-9c) as light yellow oil, MS: 297.1 & 299.1 (M+H$^+$) and 38% of N-((7R,8R or 7S,8S)-4-bromo-7-methyl-5,6,7,8-tetrahydro-isoquinolin-8-yl)-propionamide (intermediate A-9d) as off-white solid, MS: 297.1 & 299.1 (M+H)$^+$.

Intermediate A-10 and A-11

(−)-(S)-4-Bromo-5,6,7,8-tetrahydroisoquinolin-8-amine and (+)-(R)-4-Bromo-5,6,7,8-tetrahydroisoquinolin-8-amine

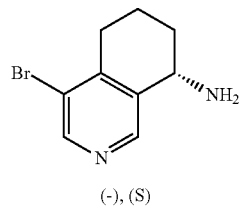

(−), (S)

Intermediate A-10

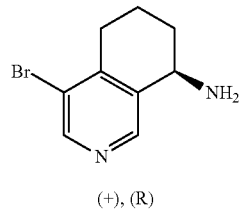

(+), (R)

Intermediate A-11

The title compounds were prepared by chiral separation of (rac)-4-bromo-5,6,7,8-tetrahydroisoquinolin-8-amine (intermediate A-1[D]) on a Chiralpak AD column (40% 2-propanol in n-heptane) to give after precipitation from CH$_2$Cl$_2$ with n-pentane 37% of (−)-(S)-4-bromo-5,6,7,8-tetrahydroisoquinolin-8-amine (intermediate A-10) as light brown crystals; MS: 227.0 (M+H$^+$, 1 Br), $[\alpha]^D_{(20\ deg)}$=−8.72, (c=0.41 in MeOH); and 36% of (+)-(R)-4-bromo-5,6,7,8-tetrahydroisoquinolin-8-amine (intermediate A-11) as light brown crystals. MS: 227.0 (M+H$^+$, 1Br), $[\alpha]^D_{(20\ deg)}$=+7.998, (c=1.0 in MeOH).

Crystallization of (−)-(S)-4-bromo-5,6,7,8-tetrahydroisoquinolin-8-amine (intermediate A-10) from n-pentane gave single crystals; X-ray crystallographic analysis allowed to assign the absolute configuration (S).

Intermediate A-12

(+)-(R)—N-(4-Bromo-5,6,7,8-tetrahydroisoquinolin-8-yl)acetamide

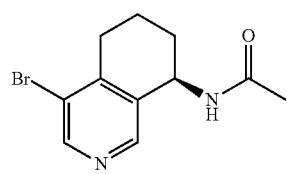

Chiral

In analogy to the procedure described for the preparation of intermediate A-4 [D], (+)-(R)-4-bromo-5,6,7,8-tetrahydroisoquinolin-8-amine (intermediate A-11) and acetic acid gave the title compound as off-white solid in 91% yield. MS: 269.0 (M+H⁺, 1Br).

Intermediate A-13

(rac)-4-bromo-7-methyl-6,7-dihydro-5H-cyclopenta[c]pyridin-7-ol

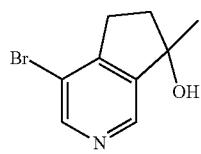

A brown suspension of 4-bromo-5H-cyclopenta[c]pyridin-7(6H)-one (intermediate A-4[B]) (424 mg, 2.0 mmol) in THF (5 mL) was cooled (−78° C.) and treated during 10 min with methylmagnesium bromide (2.1 mL, 3.0 mmol, 1.4 M in THF:toluene 1:3). The reaction was allowed to warm up to RT over 3 h then stirred for 1.5 h at RT. The mixture was poured on aq. sat. NH₄Cl-solution and extracted with EtOAc (3×). The organic layer was dried over Na₂SO₄ and concentrated in vacuo. Purification by flash chromatography (50 g SiO₂, Telos-cartridge, CH₂Cl₂/MeOH (4%)) gave the title compound (180 mg, 40%) as dark green viscous oil. MS: 228.0 (M+H⁺, 1Br).

Intermediate A-14 [C1] and A-14 [C2]

4-(3-Fluoro-4-trifluoromethyl-phenyl)-5,6-dihydro-[2]pyrindin-7-one and 4-(3-Fluoro-4-trifluoromethyl-phenyl)-5,6-dihydro-[2]pyrindin-5-one Intermediate A-14 [C1]

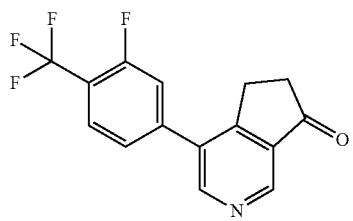

Intermediate A-14 [C2]

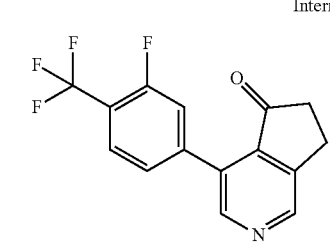

[A] 5-(3-Fluoro-4-trifluoromethyl-phenyl)-oxazole

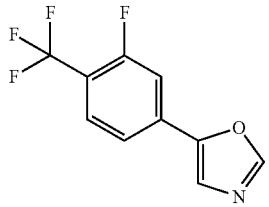 [SMILES: Fc1cc(-c2cnco2)ccc1C(F)(F)F]

A solution of 3-fluoro-4-(trifluoromethyl)benzaldehyde (1.40 g, 7.07 mmol) and p-toluenesulfonylmethyl isocyanide (1.53 g, 7.68 mmol; TosMIC) in MeOH (100 mL) was treated with potassium carbonate (1.97 g, 14.14 mmol) and the suspension heated to reflux for 14 h. After being cooled to room temperature, the solvent was removed under reduced pressure and the crude product triturated with water at 0° C. (2×25 mL). The slightly orange precipitate was collected by filtration and dried under vacuum (4.46 g, 92%). MS: 232.0 (M+H)⁺.

[B] 4-(3-Fluoro-4-trifluoromethyl-phenyl)-6,7-dihydro-5H-[2]pyrindine

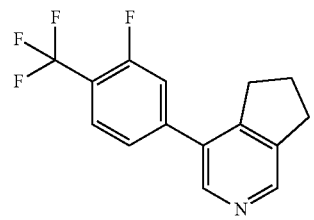 [SMILES: Fc1cc(-c2cncc3c2CCC3)ccc1C(F)(F)F]

A solution of 5-(3-fluoro-4-(trifluoromethyl)phenyl)-oxazole (0.50 g, 2.16 mmol), cyclopentene (2.95 g, 43.3 mmol) and trifluoroacetic acid (0.49 g, 4.33 mmol) in o-dichlorobenzene (12 mL) was heated under microwave irradiation to 220° C. for 6 h. To the reaction mixture was added triethylamine (5 mL) and the solvent mixture removed under reduced pressure. Purification by flash chromatography (70 g SiO₂, Telos-cartridge) eluting with a 0 to 50% EtOAc/n-heptane gradient provided the title compound (266 mg, 44%) as a slightly brown solid. MS: 282.5 (M+H)⁺.

Alternatively, this reaction step has also been conducted under flow conditions:

The reaction was performed on a custom-made flow system consisting of a Dionex P580 pump and a HP 6890 Series Gas Chromatography oven used as a heating source. The GC oven was equipped with a stainless steel coil reactor (53 mL volume) made from Supelco stainless steel tube (ID=2.1 mm). After heating to 230° C. using toluene as a system solvent, a mixture of cyclopentene (1.77 g, 26.0 mmol) and trifluoroacetic acid (0.30 g, 2.60 mmol) in toluene (1.0 mL), a mixture of 5-(3-fluoro-4-(trifluoromethyl)phenyl)oxazole (0.30 g, 1.30 mmol), cyclopentene (1.77 g, 26.0 mmol) and trifluoroacetic acid (0.30 g, 2.60 mmol) in toluene (1.0 mL) and finally a mixture of cyclopentene (1.77 g, 26.0 mmol) and trifluoroacetic acid (0.30 g, 2.60 mmol) in toluene (1.0 mL) were injected onto the stainless steel coil reactor in sequential order. The system was run at a flow rate of 0.35 mL/min equaling to a nominal residence time of $t_R$=150 min and an effective residence time of $t_{R,eff}$=120 min taking the 25% volume expansion of toluene at 230° C. into account (R. E. Martin et al., *Eur. J. Org. Chem.* 2012, 47-52). A 750 psi back-pressure regulator with a protection guard (filled with sand/glass wool) was used at the exit of the reactor to maintain system pressure. The reaction mixture was collected in a round bottom flask, triethylamine (5 mL) was added and the solvent mixture removed under reduced pressure. Purification by flash chromatography (50 g SiO$_2$, Telos-cartridge) eluting with a 0 to 50% EtOAc/n-heptane gradient provided the title compound (183 mg, 50%) as a slightly brown solid. MS: 282.5 (M+H)$^+$.

[C1] 4-(3-Fluoro-4-trifluoromethyl-phenyl)-5,6-dihydro-[2]pyrindin-7-one and [C2] 4-(3-fluoro-4-trifluoromethyl-phenyl)-6,7-dihydro-[2]pyrindin-5-one Intermediate A-14 [C1]

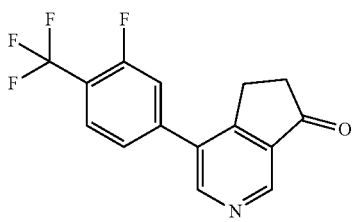 [SMILES: O=C1CCc2c1cncc2-c1ccc(C(F)(F)F)cc1]

Intermediate A-14 [C2]

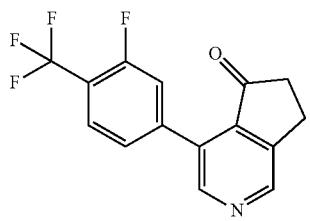

To a solution of 4-(3-fluoro-4-trifluoromethyl-phenyl)-6,7-dihydro-5H-[2]pyrindine (76.0 mg, 0.27 mmol) and dirhodium(II, III) tetrakis caprolactamate (1.8 mg, 0.0027 mmol; synthesis described in M. P. Doyle et al., *J. Am. Chem. Soc.* 1993, 115, 958-964) in dichloromethane (0.5 mL) was added sodium bicarbonate (22.7 mg, 0.27 mmol) and tert-butyl hydroperoxide (0.25 mL, 1.35 mmol). The reaction mixture was stirred at room temperature for 48 h. During this time period additional equivalents of tert-butyl hydroperoxide (1.25 mL, 6.75 mmol) were added in small portions. The solvent was removed under reduced pressure and the crude reaction mixture purified by flash chromatography (20 g SiO$_2$, Telos-cartridge) eluting with a 0 to 50% EtOAc-heptane gradient to provide 15.5 mg (19%) of 4-(3-fluoro-4-trifluoromethyl-phenyl)-5,6-dihydro-[2]pyrindin-7-one (intermediate A-14 [C1]) as slightly yellow solid; MS: 296.1 (M+H)$^+$; and 17.4 mg (22%) of 4-(3-fluoro-4-trifluoromethyl-phenyl)-6,7-dihydro-[2]pyrindin-5-one (intermediate A-14 [C2]) as slightly yellow solid. MS: 296.4 (M+H)$^+$.

Intermediate A-15

4-(4-Trifluoromethyl-phenyl)-5,6-dihydro-[2]pyrindin-7-one

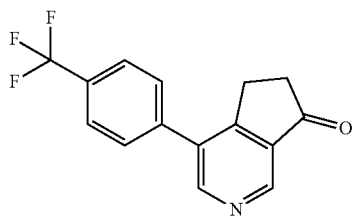 [SMILES: O=C1CCc2c1cncc2-c1ccc(C(F)(F)F)cc1]

[A] 4-(4-Trifluoromethyl-phenyl)-6,7-dihydro-5H-[2]pyrindine

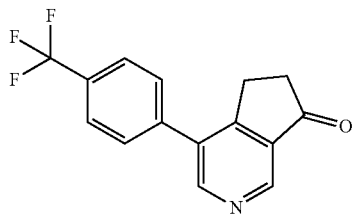

In analogy to the procedure described for the preparation of 4-(3-fluoro-4-trifluoromethyl-phenyl)-6,7-dihydro-5H-[2]pyrindine (intermediate A-14 [B], batch approach), replacing 5-(3-fluoro-4-(trifluoromethyl)phenyl)-oxazole with 5-(4-trifluoromethyl-phenyl)-oxazole (CAS[87150-14-9]). The title compound was obtained as a light brown oil in 32% yield. MS: 264.1 (M+H)$^+$.

[B] 4-(4-Trifluoromethyl-phenyl)-5,6-dihydro-[2]pyrindin-7-one

In analogy to the procedure described for the preparation of 4-(3-fluoro-4-trifluoromethyl-phenyl)-5,6-dihydro-[2]pyrindin-7-one (intermediate A-14 [C1]), replacing 4-(3-fluoro-4-trifluoromethyl-phenyl)-6,7-dihydro-5H-[2]pyrindine with 4-(4-trifluoromethyl-phenyl)-6,7-dihydro-5H-[2]pyrindine. The title compound was obtained as a light brown oil in 24% yield. MS: 278.1 (M+H⁺).

Intermediate A-16

(R)—N-(4-Bromo-5,6,7,8-tetrahydroisoquinolin-8-yl)propionamide

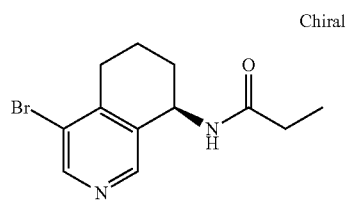 [SMILES: CCC(=O)N[C@@H]1CCCc2c(Br)cncc21]

In analogy to the procedure described for the preparation of intermediate A-4 [D], (+)-(R)-4-bromo-5,6,7,8-tetrahydroisoquinolin-8-amine (intermediate A-11) and propionic acid gave the title compound as white solid in 97% yield. MS: 283.5 (M+H⁺, 1 Br).

Intermediate A-17

(rac)-4-bromo-6,6-dimethyl-6,7-dihydro-5H-cyclopenta[c]pyridin-7-ol

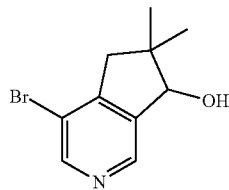

[A] Ethyl 3-(3,5-dibromopyridin-4-yl)propanoate

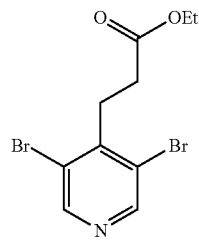 [SMILES: CCOC(=O)CCc1c(Br)cncc1Br]

To a solution of LDA (0.308 mol) [generated from N,N-diisopropylamine (31.2 g, 0.308 mol) and n-BuLi (123 mL, 0.308 mol, 2.5M in hexane) in 800 mL THF] was added slowly a solution of 3,5-dibromo-4-methylpyridine (70 g, 0.28 mol) in THF (300 mL) while the inner temperature was maintained below −70° C. After the addition, the resulting mixture was stirred for another 30 min at −78° C. before ethyl bromoacetate (116.9 g, 0.7 mol) was slowly added and the reaction mixture was stirred at −78° C. for another 1.5 h. 10% aq. AcOH was added (resulting pH=4-5), and the reaction was allowed to warm up to room temperature. After evaporation of solvent, the residue was poured into sat. aq. NaHCO₃ solution, and was extracted with EtOAc (1 L×3). The combined organic layers were washed with brine and dried over Na₂SO₄, filtered and concentrated in vacuo to give a crude product which was purified by column chromatography (n-pentane:EtOAc=15:1~5:1) to afford the title compound (30 g, 32%) as a gray solid. MS: 337.7 (M+H⁺, 2 Br).

[B] 4-bromo-5H-cyclopenta[c]pyridin-7(6H)-one

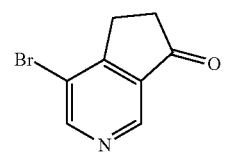

To a solution of ethyl 3-(3,5-dibromopyridin-4-yl)propanoate (30 g, 89 mmol) in THF (50 mL) was added slowly n-BuLi (71.2 mL, 178 mmol, 2.5 M in hexane) at −78° C. The resulting mixture was stirred for another 30 min at −78° C. before it was quenched with water, and extracted with EtOAc (500 mL×3). The combined organic layers were dried over Na₂SO₄, filtered, and concentrated in vacuo to give a crude product which was purified by column chromatography (n-pentane:EtOAc=5:1) to give title compound (7 g, 37%) as a white solid. MS: 211.8 (M+H⁺, 1 Br).

[C] 4-bromo-6,6-dimethyl-5H-cyclopenta[c]pyridin-7(6H)-one

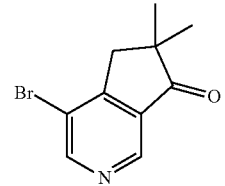

To a mixture of 4-bromo-5H-cyclopenta[c]pyridin-7(6H)-one (3 g, 14.15 mmol) and MeI (22 g, 155 mmol) in dry THF (60 mL) was added slowly LiHMDS (37 mL, 37 mmol, 1M in THF) at −20° C. After being stirred for 1 h, the reaction was warmed up to 18° C. and stirred for another 2 h. The mixture was quenched with aq. NH₄Cl solution and then extracted with EtOAc (50 mL×3). The organic layer was washed with water, brine, dried over Na₂SO₄, filtered and concentrated in vacuo to give a crude product which was purified by column chromatography (n-pentane:EtOAc=5:1) to afford the title compound (1.1 g, 32%) as a white solid. MS: 239.7 (M+H⁺, 1 Br).

[D] (rac)-4-bromo-6,6-dimethyl-6,7-dihydro-5H-cyclopenta[c]pyridin-7-ol

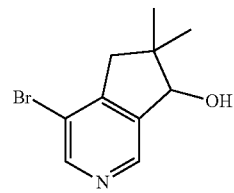

To a solution of 4-bromo-6,6-dimethyl-5H-cyclopenta[c]pyridin-7(6H)-one (1.1 g, 4.58 mmol) in MeOH (25 mL) was added NaBH₄ (261.3 mg, 6.88 mmol) portion wise. The resulting mixture was stirred for 1 h before it was quenched with water. The solution was concentrated in vacuo and the residue was extracted between EtOAc and H₂O (20 mL×3). The combined organic layers were dried over Na₂SO₄, filtered, and concentrated in vacuo to give a crude title product. MS: 243.7 (M+H⁺, 1 Br).

Example 1

(rac)-4-(8-Amino-5,6,7,8-tetrahydroisoquinolin-4-yl)benzonitrile

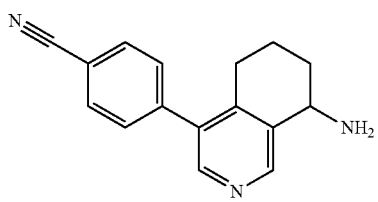 [SMILES: N#Cc1ccc(-c2cncc3c2CCCC3N)cc1]

In a 100 mL round-bottomed flask, (rac)-4-bromo-5,6,7,8-tetrahydroisoquinolin-8-amine (intermediate A-1[D]) (681 mg, 3 mmol) and 4-cyanophenylboronic acid (540 mg, 3.6 mmol) were dissolved in ethanol (54 mL) to give a light brown solution. Na₂CO₃ (350 mg, 3.3 mmol), dissolved in water (8.9 mL) was added followed by tetrakis(triphenylphosphine)palladium (0) (104 mg, 90 μmol) after evacuation and replacing 5 times with Argon. The solution was then heated at 85° C. overnight. The reaction was treated with an aq. 10% NaCl solution and extracted with AcOEt (3×). The organic phases were washed again with an aq. 10% NaCl solution, dried over Na₂SO₄, filtered and evaporated under reduced pressure to give 1.39 g brown foam which was purified by flash chromatography (50 g SiO₂, Telos-cartridge, CH₂Cl₂/MeOH (5 to 7.5%)) and precipitated from CH₂Cl₂ with n-pentane to give the title compound (605 mg, 81%) as a light brown foam. MS: 250.1 (M+H⁺).

Example 2

(rac)-N-(4-(4-Cyanophenyl)-5,6,7,8-tetrahydroisoquinolin-8-yl)ethanesulfonamide

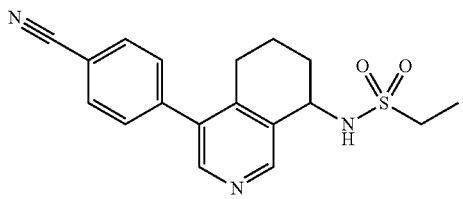 [SMILES: CCS(=O)(=O)NC1CCCc2c(-c3ccc(C#N)cc3)cncc21]

A cooled (0° C.) solution of (rac)-4-(8-amino-5,6,7,8-tetrahydroisoquinolin-4-yl)benzonitrile (example 1) (62.3 mg, 250 μmol) in CH₂Cl₂ (3.6 ml) was treated with ethanesulfonyl chloride (26.6 μL, 275 μmol) and Et₃N (41.8 μL, 300 μmol). After ½ h the mixture was stirred at room temperature for 3 h, cooled down (0° C.) and treated again with ethanesulfonyl chloride (7.3 μL, 75 μmol) and Et₃N (11.5 μL, 82.5 μmol). After 2 h at room temperature, the mixture was concentrated in vacuo and purified by flash chromatography (20 g SiO₂, Telos-cartridge, CH₂Cl₂/MeOH (0.5 to 1.5%)) to give after precipitation from CH₂Cl₂ with n-pentane the pure title compound (43 mg, 50%) as a off-white powder. MS: 342.1 (M+H⁺).

Example 3

(rac)-N-[4-(4-Cyanophenyl)-5,6,7,8-tetrahydroisoquinolin-8-yl]-N'-propylsulfuric diamide

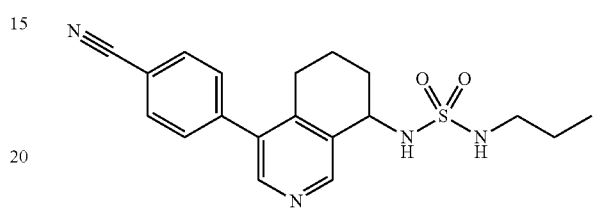

A cooled (0° C.) solution of (rac)-4-(8-amino-5,6,7,8-tetrahydroisoquinolin-4-yl)benzonitrile (example 1) (62.3 mg, 250 μmol) in CH₂Cl₂ (3 ml) was treated with propylsulfamoyl chloride (98.5 mg, 625 μmol) in CH₂Cl₂ (0.6 ml) and Et₃N (69.7 μL, 500 μmol). After 1 h the mixture was stirred at room temperature for 1 h, cooled down (0° C.) and treated again with Et₃N (69.7 μL, 500 μmol). After ½ h at room temperature, the mixture was treated with MeOH (0.2 mL) and extracted with water/AcOEt (3×). The organic phases were dried over Na₂SO₄, filtered and evaporated under reduced pressure. Purification by flash chromatography (50 g SiO₂, Telos-cartridge, CH₂Cl₂/MeOH (1 to 3%)) and precipitation from CH₂Cl₂ with n-pentane gave the title compound (63 mg, 68%) as off-white powder. MS: 371.2 (M+H⁺).

Example 4

(rac)-1-(4-(4-Cyanophenyl)-5,6,7,8-tetrahydroisoquinolin-8-yl)-3-ethylurea

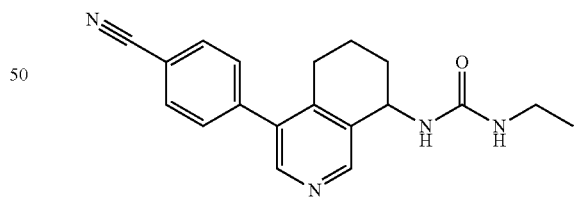

A cooled (0° C.) solution of (rac)-4-(8-amino-5,6,7,8-tetrahydroisoquinolin-4-yl)benzonitrile (example 1) (62.3 mg, 250 μmol) in CH₂Cl₂ (5 mL) was treated with ethyl isocyanate (51.6 μL, 625 μmol) in CH₂Cl₂ (0.6 mL) and Et₃N (69.7 μL, 500 μmol). After ½ h the solution was stirred at room temperature for 1 h and treated with MeOH (0.2 mL). The reaction mixture was poured on aq. 10% KH₂PO₄ solution followed by extraction with AcOEt (3×). The organic phases were washed once with aq. sat. NaCl solution. The combined organic phases were dried (Na₂SO₄), filtered and purified by flash chromatography (50 g SiO₂, Telos-cartridge, CH₂Cl₂/

MeOH (1 to 3%)). Precipitation from CH$_2$Cl$_2$ with n-pentane gave the title compound (64 mg, 80%) as off-white powder. MS: 321.2 (M+H$^+$).

Example 5

(rac)-N-(4-(4-Cyanophenyl)-5,6,7,8-tetrahydroisoquinolin-8-yl)propionamide

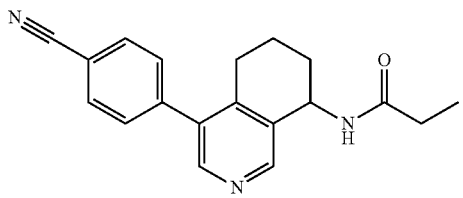 [SMILES: CCC(=O)NC1CCCc2c(-c3ccc(C#N)cc3)cncc21]

To a stirred solution of (rac)-4-(8-amino-5,6,7,8-tetrahydroisoquinolin-4-yl)benzonitrile (example 1) (480 mg, 1.93 mmol) and propionic acid (158 µL, 2.12 mmol) in CH$_2$Cl$_2$ (10 mL) at 0° C. under Argon was added EDCI (406 mg, 2.12 mmol). Stirring was continued over night and the reaction mixture was allowed to warm up to room temperature. The reaction mixture was poured into aq. 10% KH$_2$PO$_4$ solution followed by extraction with AcOEt (3×). The organic phases were washed once with aq. 10% KH$_2$PO$_4$, aq. sat. NaHCO$_3$ and with aq. sat. NaCl solution. The combined organic phases were dried over Na$_2$SO$_4$, filtered and evaporated to afford the title compound (558 mg, 95%) as light brown solid. MS: 306.2 (M+H$^+$).

Example 6 and Example 7

(−)-(S or R)—N-(4-(4-Cyanophenyl)-5,6,7,8-tetrahydroisoquinolin-8-yl)propionamide and (+)-(R or S)—N-(4-(4-Cyanophenyl)-5,6,7,8-tetrahydroisoquinolin-8-yl)propionamide Example 6

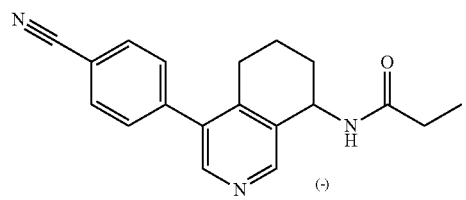

Example 7

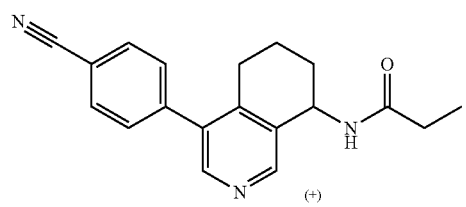

The title compounds were prepared by chiral separation of (rac)-N-(4-(4-cyanophenyl)-5,6,7,8-tetrahydroisoquinolin-8-yl)propionamide (example 5) on a Chiralpak AD column (30% 2-propanol in n-heptane) to give after precipitation from CH$_2$Cl$_2$ with n-pentane 36% of (−)-(S or R)—N-(4-(4-cyanophenyl)-5,6,7,8-tetrahydroisoquinolin-8-yl)propionamide (example 6) as off-white solid, 306.2 (M+H$^+$) and 37% of (+)-(R or S)—N-(4-(4-cyanophenyl)-5,6,7,8-tetrahydroisoquinolin-8-yl)propionamide (example 7) as off-white solid. MS: 306.2 (M+H$^+$).

Example 8

(rac)-N-(4-(4-Cyanophenyl)-5,6,7,8-tetrahydroisoquinolin-8-yl)acetamide

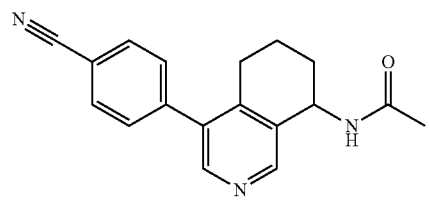 [SMILES: CC(=O)NC1CCCc2c(-c3ccc(C#N)cc3)cncc21]

A cooled (−20° C.) solution of (rac)-4-(8-amino-5,6,7,8-tetrahydroisoquinolin-4-yl)benzonitrile (example 1) (62.3 mg, 250 µmol) in CH$_2$Cl$_2$ (3.6 ml) was treated with acetyl chloride (21.3 µL, 275 µmol) and Et$_3$N (41.8 µL, 300 µmol). After ½ h, an additional drop of acetyl chloride was added and after 5 min. the mixture was treated with MeOH (0.2 mL) and extracted with water/AcOEt (3×). The organic phases were dried over Na$_2$SO$_4$, filtered and evaporated under reduced pressure. Purification by flash chromatography (50 g SiO$_2$, Telos-cartridge, CH$_2$Cl$_2$/MeOH (2 to 3%)) and precipitation from CH$_2$Cl$_2$ with n-pentane gave the title compound (32 mg, 44%) as off-white powder. MS: 292.1 (M+H$^+$).

Example 9

(rac)-N-(4-(4-Cyanophenyl)-5,6,7,8-tetrahydroisoquinolin-8-yl)isobutyramide

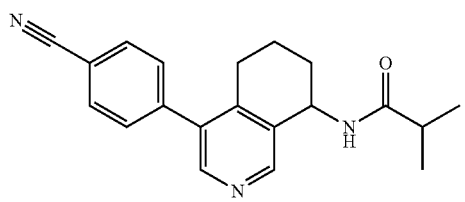 [SMILES: CC(C)C(=O)NC1CCCc2c(-c3ccc(C#N)cc3)cncc21]

In analogy to the procedure described for the preparation of example 8, (rac)-4-(8-amino-5,6,7,8-tetrahydroisoquinolin-4-yl)benzonitrile (example 1) was reacted with isobutyryl chloride to give the title compound as a off-white powder in 63% yield. MS: 320.2 (M+H$^+$).

Example 10

(rac)-Ethyl 4-(4-cyanophenyl)-5,6,7,8-tetrahydroisoquinolin-8-ylcarbamate

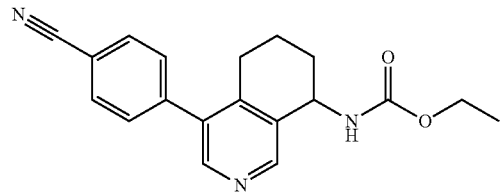 [SMILES: CCOC(=O)NC1CCCc2c(-c3ccc(C#N)cc3)cncc21]

In analogy to the procedure described for the preparation of example 3, (rac)-4-(8-amino-5,6,7,8-tetrahydroisoquinolin-4-yl)benzonitrile (example 1) was reacted with ethyl chloroformate to give the title compound as a off-white powder in 39% yield. MS: 322.2 (M+H$^+$).

Example 11

(rac)-4-(8-Hydroxy-5,6,7,8-tetrahydroisoquinolin-4-yl)benzonitrile

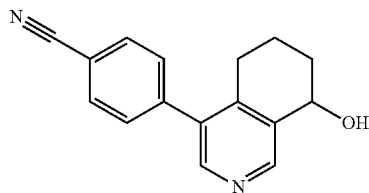 [SMILES: N#Cc1ccc(-c2cncc3c2CCCC3O)cc1]

In analogy to the procedure described for the preparation of example 1, (rac)-4-bromo-5,6,7,8-tetrahydroisoquinolin-8-ol (intermediate A-2) was reacted with 4-cyanophenylboronic acid to give the title compound as light brown powder in 83% yield. MS: 251.1 (M+H$^+$).

Example 12

(rac)-4-(4-Cyanophenyl)-5,6,7,8-tetrahydroisoquinolin-8-yl ethylcarbamate

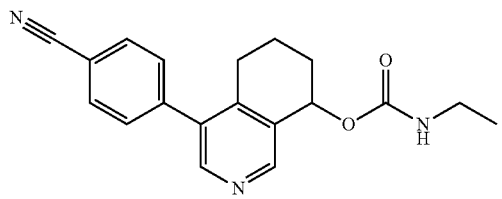 [SMILES: CCNC(=O)OC1CCCc2c(-c3ccc(C#N)cc3)cncc21]

A cooled (0° C.) solution of (rac)-4-(8-hydroxy-5,6,7,8-tetrahydroisoquinolin-4-yl)benzonitrile (example 11) (50 mg, 200 µmol) in CH$_2$Cl$_2$ (1.4 mL) was treated with ethyl isocyanate (24.8 µL, 300 µmol) and Et$_3$N (24.8 µL, 300 µmol). After stirring 1 night at room temperature and 1 h at reflux again ethyl isocyanate (24.8 µL, 300 µmol) and Et$_3$N (24.8 µL, 300 µmol) were added. The solution was refluxed for 9 h, treated again with ethyl isocyanate (24.8 µL, 300 µmol), Et$_3$N (24.8 µL, 300 µmol) and DMAP (2.4 mg, 20 µmol). After 1 night at room temperature MeOH (2 mL) was added. The reaction mixture was poured on aq. sat. NaHCO$_3$ solution followed by extraction with AcOEt (3×). The organic phases were washed once with aq. sat. NaCl solution. The combined organic phases were dried (Na$_2$SO$_4$), filtered and purified by flash chromatography (50 g SiO$_2$, Telos-cartridge, CH$_2$Cl$_2$/MeOH 1%). Precipitation from CH$_2$Cl$_2$ with n-pentane gave the title compound (33 mg, 51%) as off-white foam. MS: 322.2 (M+H$^+$).

Example 13

(rac)-4-(8-Methoxy-5,6,7,8-tetrahydroisoquinolin-4-yl)benzonitrile

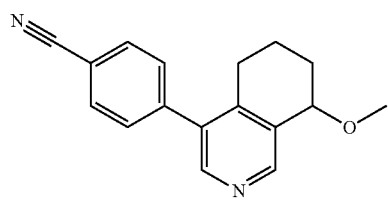 [SMILES: COC1CCCc2c(-c3ccc(C#N)cc3)cncc21]

A cooled (0° C.) solution of (rac)-4-(8-hydroxy-5,6,7,8-tetrahydroisoquinolin-4-yl)benzonitrile (example 11) (50 mg, 200 µmol) in DMF (1.4 mL) was treated with NaH (55% in oil, 9.6 mg, 220 µmol) and after ½ h with methyl iodide (13.7 µL, 220 µmol) in DMF (0.2 mL). After stirring 1 h at 0° C. and 1.5 h at room temperature, the reaction mixture was poured on aq. sat. NaHCO$_3$ solution followed by extraction with AcOEt (3×). The organic phases were washed once with aq. sat. NaCl solution. The combined organic phases were dried (Na$_2$SO$_4$), filtered and purified by flash chromatography (50 g SiO$_2$, Telos-cartridge, CH$_2$Cl$_2$/MeOH 1%). Precipitation from CH$_2$Cl$_2$ with n-pentane gave the title compound (17 mg, 32%) as off-white powder. MS: 265.1 (M+H$^+$).

Example 14

(rac)-4-(8-(3,4-Dimethylphenyl)-8-hydroxy-5,6,7,8-tetrahydroisoquinolin-4-yl)benzonitrile

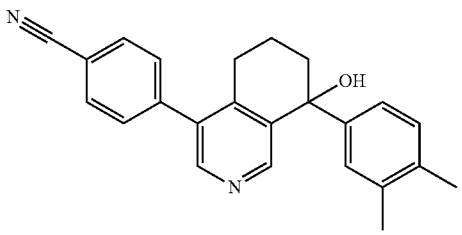 [SMILES: Cc1ccc(C2(O)CCCc3c(-c4ccc(C#N)cc4)cncc32)cc1C]

In analogy to the procedure described for the preparation of example 1, (rac)-4-bromo-8-(3,4-dimethylphenyl)-5,6,7,8-tetrahydroisoquinolin-8-ol (intermediate A-3) was reacted with 4-cyanophenylboronic acid to give the title compound as white powder in 79% yield. MS: 355.2 (M+H⁺).

Example 15 and Example 16

(+)-(S or R)-4-(8-(3,4-Dimethylphenyl)-8-hydroxy-5,6,7,8-tetrahydroisoquinolin-4-yl)benzonitrile and (−)-(R or S)-4-(8-(3,4-Dimethylphenyl)-8-hydroxy-5,6,7,8-tetrahydroisoquinolin-4-yl)benzonitrile Example 15

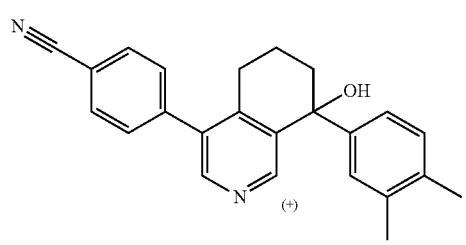

Example 16

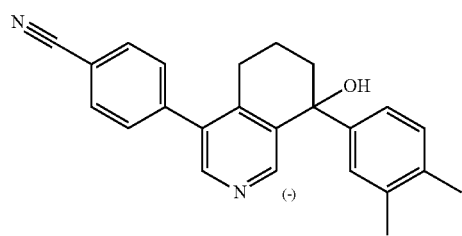

The title compounds were prepared by chiral separation of (rac)-4-(8-(3,4-dimethylphenyl)-8-hydroxy-5,6,7,8-tetrahydroisoquinolin-4-yl)benzonitrile (example 14) on a Chiralpak AD column (40% 2-propanol in n-heptane) to give after precipitation from CH₂Cl₂ with n-pentane 39% of (+)-(S or R)-4-(8-(3,4-dimethylphenyl)-8-hydroxy-5,6,7,8-tetrahydroisoquinolin-4-yl)benzonitrile (example 15) as off-white powder, MS: 355.2 (M+H⁺) and 34% of (−)-(R or S)-4-(8-(3,4-dimethylphenyl)-8-hydroxy-5,6,7,8-tetrahydroisoquinolin-4-yl)benzonitrile (example 16) as off-white powder. MS: 355.2 (M+H⁺).

Example 17

(rac)-N-(4-(4-Cyanophenyl)-6,7-dihydro-5H-cyclopenta[c]pyridin-7-yl)propionamide

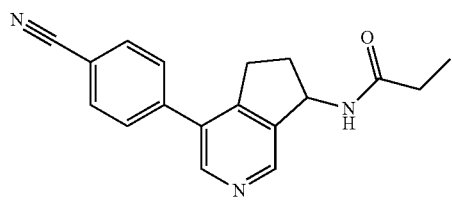 [SMILES: CCC(=O)NC1CCc2c(-c3ccc(C#N)cc3)cncc21]

In analogy to the procedure described for the preparation of example 1, (rac)-N-(4-bromo-6,7-dihydro-5H-cyclopenta[c]pyridin-7-yl)propionamide (intermediate A-4) was reacted with 4-cyanophenylboronic acid to give the title compound as light green powder in 79% yield. MS: 292.1 (M+H⁺).

Example 18 and Example 19

(−)-(S or R)—N-(4-(4-Cyanophenyl)-6,7-dihydro-5H-cyclopenta[c]pyridin-7-yl)propionamide and (+)-(R or S)—N-(4-(4-Cyanophenyl)-6,7-dihydro-5H-cyclopenta[c]pyridin-7-yl)propionamide Example 18

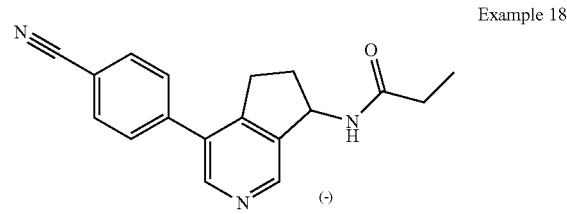

Example 19

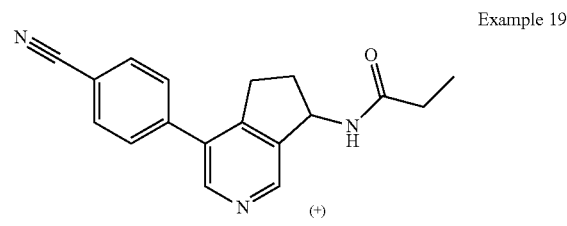

The title compounds were prepared by chiral separation of (rac)-N-(4-(4-cyanophenyl)-6,7-dihydro-5H-cyclopenta[c]pyridin-7-yl)propionamide (example 17) on a Chiralpak AD column (20% 2-propanol in n-heptane) to give after precipitation from CH₂Cl₂ with n-pentane 31% of (−)-(S or R)—N-(4-(4-cyanophenyl)-6,7-dihydro-5H-cyclopenta[c]pyridin-7-yl)propionamide (example 18) as off-white powder, MS: 292.1 (M+H⁺) and 33% of (+)-(R or S)—N-(4-(4-cyanophenyl)-6,7-dihydro-5H-cyclopenta[c]pyridin-7-yl)propionamide (example 19) as off-white powder. MS: 292.1 (M+H⁺).

Example 20

(rac)-N-(4-(3-Chloro-4-fluorophenyl)-5,6,7,8-tetrahydroisoquinolin-8-yl)propionamide

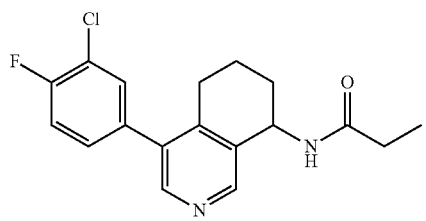 [SMILES: CCC(=O)NC1CCCc2c(-c3ccc(F)c(Cl)c3)cncc21]

In analogy to the procedure described for the preparation of example 1, (rac)-N-(4-bromo-5,6,7,8-tetrahydroisoquinolin-8-yl)propionamide (intermediate A-1) was reacted with 3-chloro-4-fluorophenylboronic acid to give the title compound as light grey foam in 74% yield. MS: 333.1 (M+H⁺, 1Cl).

Example 21

(rac)-N-(4-(4-(Trifluoromethyl)phenyl)-5,6,7,8-tetrahydroisoquinolin-8-yl)propionamide

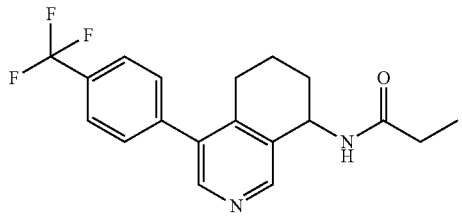 [SMILES: CCC(=O)NC1CCCc2c(-c3ccc(C(F)(F)F)cc3)cncc21]

In analogy to the procedure described for the preparation of example 1, (rac)-N-(4-bromo-5,6,7,8-tetrahydroisoquinolin-8-yl)propionamide (intermediate A-1) was reacted with 4-(trifluoromethyl)phenylboronic acid to give the title compound as light grey foam in 86% yield. MS: 349.2 (M+H⁺).

Example 22 and Example 23

(−)-(S or R)—N-(4-(4-(Trifluoromethyl)phenyl)-5,6,7,8-tetrahydroisoquinolin-8-yl)propionamide and (+)-(R or S)—N-(4-(4-(Trifluoromethyl)phenyl)-5,6,7,8-tetrahydroisoquinolin-8-yl)propionamide Example 22

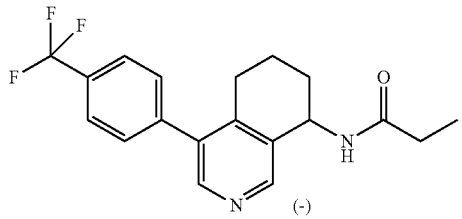

Example 23

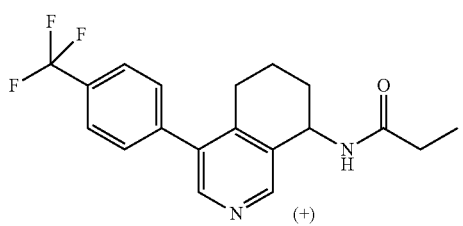

The title compounds were prepared by chiral separation of (rac)-N-(4-(4-(trifluoromethyl)phenyl)-5,6,7,8-tetrahydroisoquinolin-8-yl)propionamide (example 21) on a Chiralpak AD column (25% 2-propanol in n-heptane) to give after precipitation from CH₂Cl₂ with n-pentane 39% of (−)-(S or R)—N-(4-(4-(trifluoromethyl)phenyl)-5,6,7,8-tetrahydroisoquinolin-8-yl)propionamide (example 22) as off-white solid, MS: 349.2 (M+H⁺) and 41% of (+)-(R or S)—N-(4-(4-(trifluoromethyl)phenyl)-5,6,7,8-tetrahydroisoquinolin-8-yl)propionamide (example 23) as off-white solid. MS: 349.2 (M+H⁺).

Example 24

(rac)-N-(4-(4-Chlorophenyl)-5,6,7,8-tetrahydroisoquinolin-8-yl)propionamide

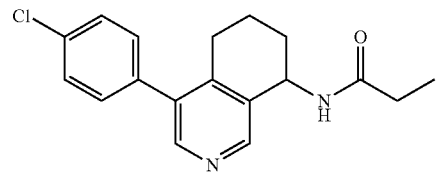 [SMILES: CCC(=O)NC1CCCc2c(-c3ccc(Cl)cc3)cncc21]

In analogy to the procedure described for the preparation of example 1, (rac)-N-(4-bromo-5,6,7,8-tetrahydroisoquinolin-8-yl)propionamide (intermediate A-1) was reacted with 4-chlorophenylboronic acid to give the title compound as light yellow foam in 86% yield. MS: 315.5 (M+H⁺, 1Cl).

Example 25 and Example 26

(−)-(S or R)—N-(4-(4-Chlorophenyl)-5,6,7,8-tetrahydroisoquinolin-8-yl)propionamide and (+)-(R or S)—N-(4-(4-Chlorophenyl)-5,6,7,8-tetrahydroisoquinolin-8-yl)propionamide Example 25

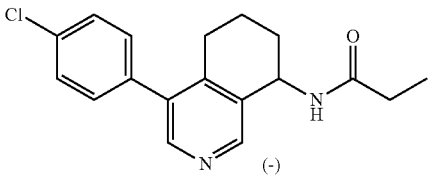

Example 26

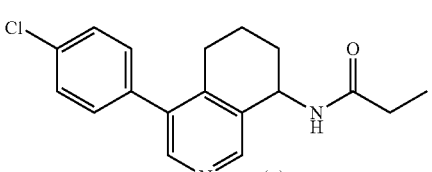

The title compounds were prepared by chiral separation of (rac)-N-(4-(4-chlorophenyl)-5,6,7,8-tetrahydroisoquinolin-8-yl)propionamide (example 24) on a Chiralpak AD column (25% 2-propanol in n-heptane) to give after precipitation from CH₂Cl₂ with n-pentane 42% of (−)-(S or R)—N-(4-(4-chlorophenyl)-5,6,7,8-tetrahydroisoquinolin-8-yl)propionamide (example 25) as off-white powder, MS: 315.4 (M+H⁺, 1Cl) and 40% of (+)-(R or S)—N-(4-(4-chlorophenyl)-5,6,7, 8-tetrahydroisoquinolin-8-yl)propionamide (example 26) as off-white powder. MS: 315.4 (M+H+, 1Cl).

Example 27

(rac)-N-(4-(4-Fluoro-3-methylphenyl)-5,6,7,8-tetrahydroisoquinolin-8-yl)propionamide

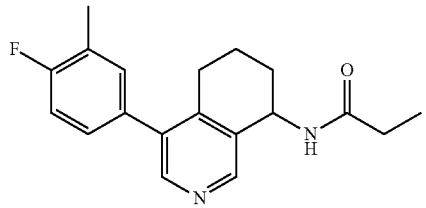 [SMILES: CCC(=O)NC1CCCc2c(-c3ccc(F)c(C)c3)cncc21]

In analogy to the procedure described for the preparation of example 1, (rac)-N-(4-bromo-5,6,7,8-tetrahydroisoquinolin-8-yl)propionamide (intermediate A-1) was reacted with 4-fluoro-3-methylphenylboronic acid to give the title compound as light yellow foam in 82% yield. MS: 313.5 (M+H+).

Example 28 and Example 29

(−)-(S or R)—N-(4-(4-Fluoro-3-methylphenyl)-5,6,7,8-tetrahydroisoquinolin-8-yl)propionamide and (+)-(R or S)—N-(4-(4-Chlorophenyl)-5,6,7,8-tetrahydroisoquinolin-8-yl)propionamide Example 28

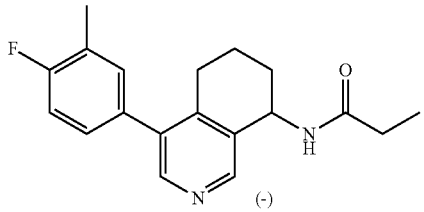

Example 29

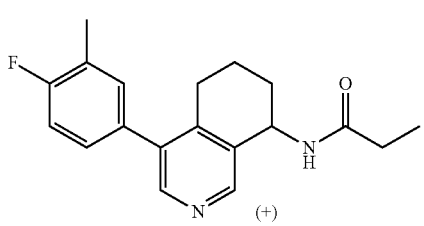

The title compounds were prepared by chiral separation of (rac)-N-(4-(4-fluoro-3-methylphenyl)-5,6,7,8-tetrahydroisoquinolin-8-yl)propionamide (example 27) on a Chiralpak AD column (30% ethanol in n-heptane) to give after precipitation from CH$_2$Cl$_2$ with n-pentane 40% of (−)-(S or R)—N-(4-(4-fluoro-3-methylphenyl)-5,6,7,8-tetrahydroisoquinolin-8-yl)propionamide (example 28) as off-white foam, MS: 313.5 (M+H+) and 40% of (+)-(R or S)—N-(4-(4-fluoro- 3-methylphenyl)-5,6,7,8-tetrahydroisoquinolin-8-yl)propionamide (example 29) as off-white foam. MS: 313.5 (M+H+).

Example 30

(rac)-N-(4-(4-Chloro-2-fluorophenyl)-5,6,7,8-tetrahydroisoquinolin-8-yl)propionamide

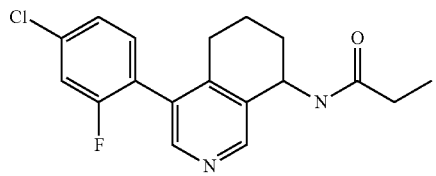 [SMILES: CCC(=O)NC1CCCc2c(-c3ccc(Cl)cc3F)cncc21]

In analogy to the procedure described for the preparation of example 1, (rac)-N-(4-bromo-5,6,7,8-tetrahydroisoquinolin-8-yl)propionamide (intermediate A-1) was reacted with 4-chloro-2-fluorophenylboronic acid. The crude mixture obtained after the work-up was reacted a second time under the conditions of example 1 with 4-chloro-2-fluorophenylboronic acid to yield after purification to the title compound as off-white foam in 70% yield. MS: 333.4 (M+H+, 1Cl).

Example 31 and Example 32

(−)-(S or R)—N-(4-(4-Chloro-2-fluorophenyl)-5,6,7,8-tetrahydroisoquinolin-8-yl)propionamide and (+)-(R or S)—N-(4-(4-Chloro-2-fluorophenyl)-5,6,7,8-tetrahydroisoquinolin-8-yl)propionamide Example 31

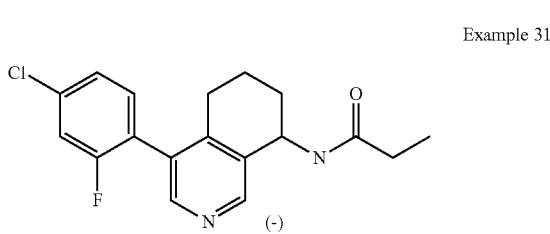

Example 32

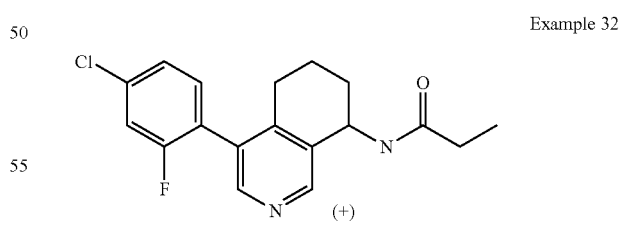

The title compounds were prepared by chiral separation of (rac)-N-(4-(4-chloro-2-fluorophenyl)-5,6,7,8-tetrahydroisoquinolin-8-yl)propionamide (example 30) on a Chiralpak AD column (20% 2-propanol in n-heptane) to give after precipitation from CH$_2$Cl$_2$ with n-pentane 38% of (−)-(S or R)—N-(4-(4-chloro-2-fluorophenyl)-5,6,7,8-tetrahydroisoquinolin-8-yl)propionamide (example 31) as white powder, MS: 333.4 (M+H+, 1Cl) and 39% of (+)-(R or S)—N-(4-(4-chloro-2- fluorophenyl)-5,6,7,8-tetrahydroisoquinolin-8-yl)propionamide (example 32) as off-white powder. MS: 333.0 (M+H+, 1Cl).

Example 33

(rac)-N-(4-(2-Fluoro-4-(trifluoromethyl)phenyl)-5,6,7,8-tetrahydroisoquinolin-8-yl)propionamide

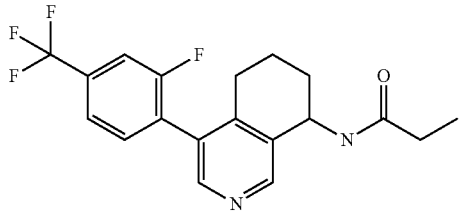

In analogy to the procedure described for the preparation of example 1, (rac)-N-(4-bromo-5,6,7,8-tetrahydroisoquinolin-8-yl)propionamide (intermediate A-1) was reacted with 2-fluoro-4-(trifluoromethyl)phenylboronic acid. The crude mixture obtained after the work-up was reacted a second time under the conditions of example 1 with 2-fluoro-4-(trifluoromethyl)phenylboronic acid to yield after purification to the title compound as light white foam in 63% yield. MS: 367.4 (M+H+).

Example 34 and Example 35

(−)-(S or R)—N-(4-(2-Fluoro-4-(trifluoromethyl)phenyl)-5,6,7,8-tetrahydroisoquinolin-8-yl)propionamide and (+)-(R or S)—N-(4-(2-Fluoro-4-(trifluoromethyl)phenyl)-5,6,7,8-tetrahydroisoquinolin-8-yl)propionamide Example 34

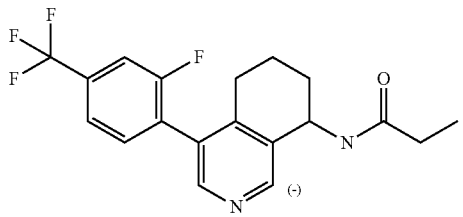

Example 35

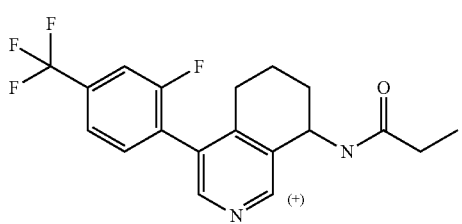 [SMILES: CCC(=O)NC1CCCc2c(-c3ccc(C(F)(F)F)cc3F)cncc21]

The title compounds were prepared by chiral separation of (rac)-N-(4-(2-fluoro-4-(trifluoromethyl)phenyl)-5,6,7,8-tetrahydroisoquinolin-8-yl)propionamide (example 33) on a Chiralpak AD column (20% 2-propanol in n-heptane) to give after precipitation from CH2Cl2 with n-pentane 41% of (−)-(S or R)—N-(4-(2-fluoro-4-(trifluoromethyl)phenyl)-5,6,7,8-tetrahydroisoquinolin-8-yl)propionamide (example 34) as white powder, MS: 367.2. (M+H+) and 41% of (+)-(R or S)—N-(4-(2-fluoro-4-(trifluoromethyl)phenyl)-5,6,7,8-tetrahydroisoquinolin-8-yl)propionamide (example 35) as off-white powder. MS: 367.2 (M+H+).

Example 36

(rac)-N-(4-(4-Chloro-3-fluorophenyl)-5,6,7,8-tetrahydroisoquinolin-8-yl)propionamide

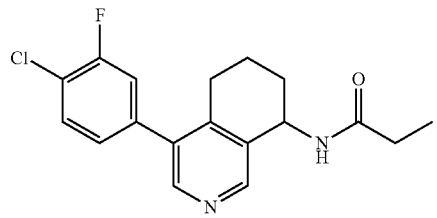

In analogy to the procedure described for the preparation of example 1, (rac)-N-(4-bromo-5,6,7,8-tetrahydroisoquinolin-8-yl)propionamide (intermediate A-1) was reacted with 4-chloro-3-fluorophenylboronic acid to give the title compound as light brown foam in 83% yield. MS: 333.4 (M+H+, 1Cl).

Example 37 and Example 38

(−)-(S or R)—N-(4-(4-Chloro-3-fluorophenyl)-5,6,7,8-tetrahydroisoquinolin-8-yl)propionamide and (+)-(R or S)—N-(4-(4-Chloro-3-fluorophenyl)-5,6,7,8-tetrahydroisoquinolin-8-yl)propionamide Example 37

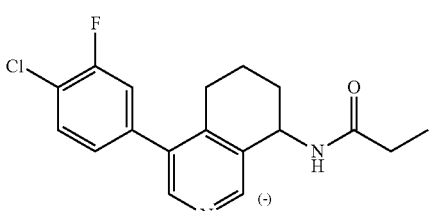

Example 38

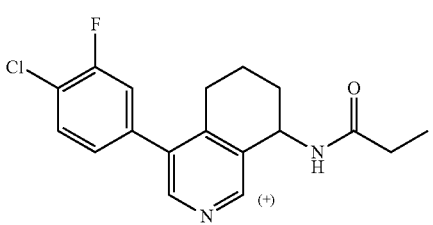 [SMILES: CCC(=O)NC1CCCc2c(-c3ccc(Cl)c(F)c3)cncc21]

The title compounds were prepared by chiral separation of (rac)-N-(4-(4-chloro-3-fluorophenyl)-5,6,7,8-tetrahydroisoquinolin-8-yl)propionamide (example 36) on a Chiralpak AD column (40% ethanol in n-heptane) to give after precipitation from CH2Cl2 with n-pentane 37% of (−)-(S or R)—N-(4-(4-chloro-3-fluorophenyl)-5,6,7,8-tetrahydroisoquinolin-8-yl)propionamide (example 37) as off-white powder, MS: 333.1 (M+H+, 1Cl) and 41% of (+)-(R or S)—N-(4-(4-chloro-3-fluorophenyl)-5,6,7,8-tetrahydroisoquinolin-8-yl)propionamide (example 38) as off-white powder. MS: 333.1 (M+H+, 1Cl).

Example 39

(rac)-N-(4-(3-Fluoro-4-(trifluoromethyl)phenyl)-5,6,7,8-tetrahydroisoquinolin-8-yl)propionamide

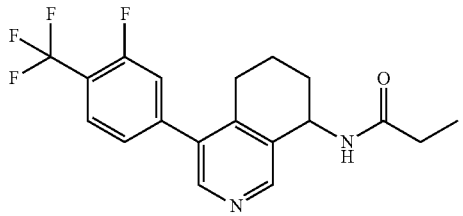

In analogy to the procedure described for the preparation of example 1, (rac)-N-(4-bromo-5,6,7,8-tetrahydroisoquinolin-8-yl)propionamide (intermediate A-1) was reacted with 3-fluoro-4-(trifluoromethyl)phenylboronic acid to give the title compound as light brown foam in 80% yield. MS: 367.1 (M+H$^+$).

Example 40 and Example 41

(−)-(S or R)—N-(4-(3-Fluoro-4-(trifluoromethyl)phenyl)-5,6,7,8-tetrahydroisoquinolin-8-yl)propionamide and (+)-(R or S)—N-(4-(3-Fluoro-4-(trifluoromethyl)phenyl)-5,6,7,8-tetrahydroisoquinolin-8-yl)propionamide Example 40

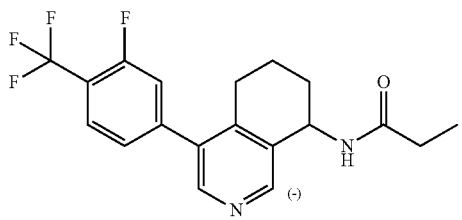 [SMILES: CCC(=O)NC1CCCc2c(-c3ccc(C(F)(F)F)c(F)c3)cncc21]

Example 41

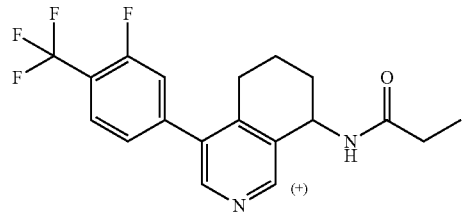

The title compounds were prepared by chiral separation of (rac)-N-(4-(3-fluoro-4-(trifluoromethyl)phenyl)-5,6,7,8-tetrahydroisoquinolin-8-yl)propionamide (example 39) on a Chiralpak AD column (20% 2-propanol in n-heptane) to give after precipitation from CH$_2$Cl$_2$ with n-pentane 40% of (−)-(S or R)—N-(4-(3-fluoro-4-(trifluoromethyl)phenyl)-5,6,7,8-tetrahydroisoquinolin-8-yl)propionamide (example 40) as white solid, MS: 367.1 (M+H$^+$) and 38% of (+)-(R or S)—N-(4-(3-fluoro-4-(trifluoromethyl)phenyl)-5,6,7,8-tetrahydroisoquinolin-8-yl)propionamide (example 41) as white solid. MS: 367.1 (M+H$^+$).

Example 42 to 45

In analogy to the procedure described for the preparation of example 1, (rac)-N-(4-bromo-5,6,7,8-tetrahydroisoquinolin-8-yl)propionamide (intermediate A-1) was reacted with the appropriate boronic acid to give the title compound.

| Ex. | Boronic acid | Name and Structure (yield and physical form) | MS (ISP) m/z [(M + H)$^+$] |
|---|---|---|---|
| 42 | 2,4-difluorophenylboronic acid | (rac)-N-(4-(2,4-Difluorophenyl)-5,6,7,8-tetrahydroisoquinolin-8-yl)propionamide (62%, light brown foam) 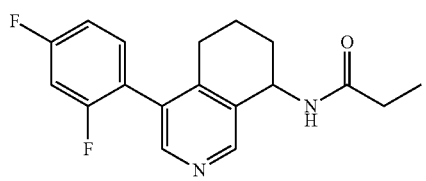 [SMILES: CCC(=O)NC1CCCc2c(-c3ccc(F)cc3F)cncc21] | 317.1 |

| Ex. | Boronic acid | Name and Structure (yield and physical form) | MS (ISP) m/z [(M + H)+] |
|---|---|---|---|
| 43 | 2,4,5-trifluorophenylboronic acid | (rac)-N-(4-(2,4,5-Trifluorophenyl)-5,6,7,8-tetrahydroisoquinolin-8-yl)propionamide (40%, white foam) 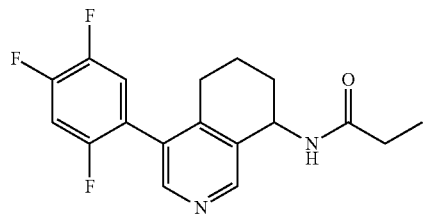 [SMILES: CCC(=O)NC1CCCc2c(-c3cc(F)c(F)cc3F)cncc21] | 335.1 |
| 44 | 3,4-difluorophenylboronic acid | (rac)-N-(4-(3,4-Difluorophenyl)-5,6,7,8-tetrahydroisoquinolin-8-yl)propionamide (85%, light brown foam) 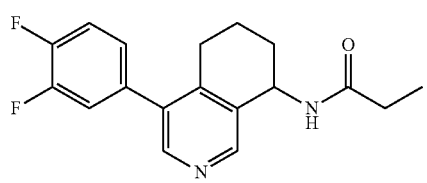 [SMILES: CCC(=O)NC1CCCc2c(-c3ccc(F)c(F)c3)cncc21] | 317.1 |
| 45 | 3,4-dichlorophenylboronic acid | (rac)-N-(4-(3,4-Dichlorophenyl)-5,6,7,8-tetrahydroisoquinolin-8-yl)propionamide (87%, off-white powder) 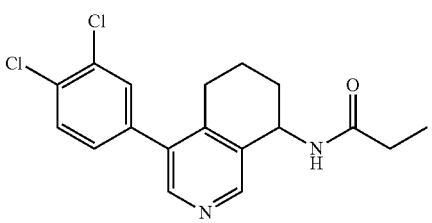 | 349.1, 2Cl |

In the case of example 43, the crude mixture obtained after the work-up was reacted a second time under the conditions of example 1 with the appropriate boronic acid (2,4,5-trifluorophenylboronic acid) to yield after purification to the title compound example 43.

Example 46

(R)-2-Hydroxy-N—[(S,R)-4-(4-trifluoromethyl-phenyl)-5,6,7,8-tetrahydro-isoquinolin-8-yl]-propionamide

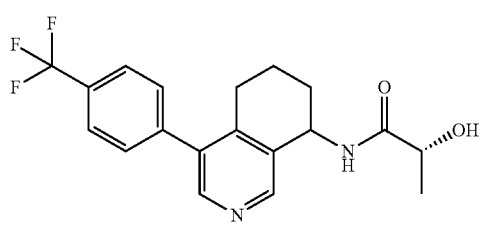

In analogy to the procedure described for the preparation of example 1, (R)—N—((R,S)-4-bromo-5,6,7,8-tetrahydro-isoquinolin-8-yl)-2-hydroxy-propionamide (intermediate A-5) was reacted with 4-(trifluoromethyl)phenylboronic acid to give the title compound as light grey powder in 84% yield. MS: 365.2 (M+H+).

Example 47 and Example 48

(+)-(R)-2-Hydroxy-N—[(R or S)-4-(4-trifluoromethyl-phenyl)-5,6,7,8-tetrahydro-isoquinolin-8-yl]-propionamide and (−)-(R)-2-Hydroxy-N—[(S or R)-4-(4-trifluoromethyl-phenyl)-5,6,7,8-tetrahydro-isoquinolin-8-yl]-propionamide Example 47

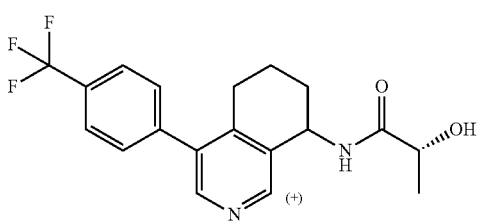 [SMILES: C[C@@H](O)C(=O)NC1CCCc2c(-c3ccc(C(F)(F)F)cc3)cncc21]

Example 48

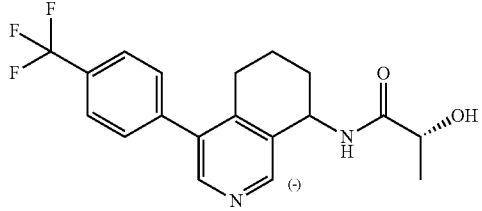

The title compounds were prepared by chiral separation of (R)-2-hydroxy-N—[(S,R)-4-(4-trifluoromethyl-phenyl)-5,6,7,8-tetrahydro-isoquinolin-8-yl]-propionamide (example 46) on a Lux 5u Amylose-2 column (15% ethanol in n-heptane) to give after precipitation from CH$_2$Cl$_2$ with n-pentane 32% of (+)-(R)-2-hydroxy-N—[(R or S)-4-(4-trifluoromethyl-phenyl)-5,6,7,8-tetrahydro-isoquinolin-8-yl]-propionamide (example 47) as white solid, MS: 365.4 (M+H$^+$) and 31% of (−)-(R)-2-hydroxy-N—[(S or R)-4-(4-trifluoromethyl-phenyl)-5,6,7,8-tetrahydro-isoquinolin-8-yl]-propionamide (example 48) as white solid. MS: 365.7 (M+H$^+$).

Example 49

(rac)-N-(4-(4-(Trifluoromethyl)phenyl)-6,7-dihydro-5H-cyclopenta[c]pyridin-7-yl)propionamide

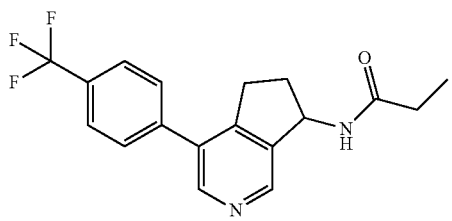

In analogy to the procedure described for the preparation of example 1, (rac)-N-(4-bromo-6,7-dihydro-5H-cyclopenta[c]pyridin-7-yl)propionamide (intermediate A-4) was reacted with 4-(trifluoromethyl)phenylboronic acid to give the title compound as grey solid in 87% yield. MS: 335.1 (M+H$^+$).

Example 50 and Example 51

(−)-(S or R)—N-(4-(4-(Trifluoromethyl)phenyl)-6,7-dihydro-5H-cyclopenta[c]pyridin-7-yl)propionamide and (+)-(R or S)—N-(4-(4-(Trifluoromethyl)phenyl)-6,7-dihydro-5H-cyclopenta[c]pyridin-7-yl)propionamide Example 50

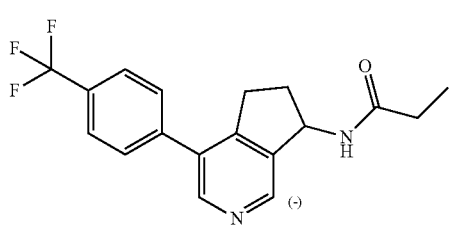 [SMILES: CCC(=O)NC1CCc2c(-c3ccc(C(F)(F)F)cc3)cncc21]

Example 51

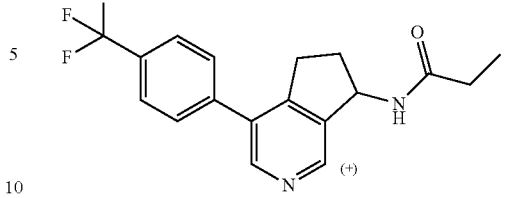

The title compounds were prepared by chiral separation of (rac)-N-(4-(4-(trifluoromethyl)phenyl)-6,7-dihydro-5H-cyclopenta[c]pyridin-7-yl)propionamide (example 49) on a Reprosil Chiral-NR column (15% ethanol in n-heptane) to give after precipitation from CH$_2$Cl$_2$ with n-pentane 36% of (−)-(S or R)—N-(4-(4-(trifluoromethyl)phenyl)-6,7-dihydro-5H-cyclopenta[c]pyridin-7-yl)propionamide (example 50) as white solid, MS: 335.1 (M+H$^+$) and 43% of (+)-(R or S)—N-(4-(4-(trifluoromethyl)phenyl)-6,7-dihydro-5H-cyclopenta[c]pyridin-7-yl)propionamide (example 51) as white solid. MS: 335.1 (M+H$^+$).

Example 52

(R)-2-Hydroxy-N—((R,S)-4-(4-(trifluoromethyl)phenyl)-6,7-dihydro-5H-cyclopenta[c]pyridin-7-yl)propanamide

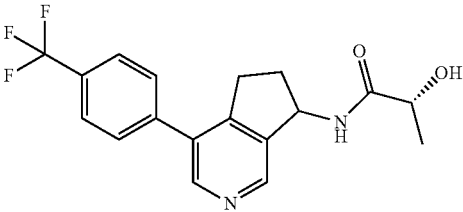 [SMILES: C[C@@H](O)C(=O)NC1CCc2c(-c3ccc(C(F)(F)F)cc3)cncc21]

In analogy to the procedure described for the preparation of example 1, (R)—N—((R,S)-4-bromo-6,7-dihydro-5H-[2]pyridin-7-yl)-2-hydroxy-propionamide (intermediate A-6) was reacted with 4-(trifluoromethyl)phenylboronic acid to give the title compound as dark green solid in 79% yield. MS: 351.1 (M+H$^+$).

Example 53 and Example 54

(−)-(R)-2-Hydroxy-N—((S or R)-4-(4-(trifluoromethyl)phenyl)-6,7-dihydro-5H-cyclopenta[c]pyridin-7-yl)propanamide and (+)-(R)-2-Hydroxy-N—((R or S)-4-(4-(trifluoromethyl)phenyl)-6,7-dihydro-5H-cyclopenta[c]pyridin-7-yl)propanamide Example 53

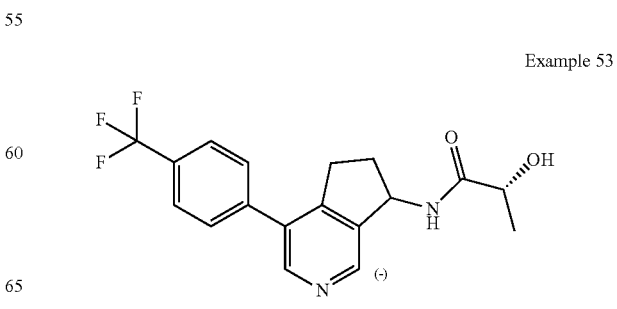

-continued

Example 54

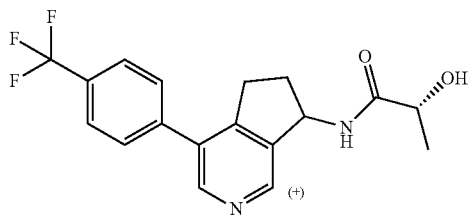

The title compounds were prepared by chiral separation of (R)-2-hydroxy-N—((R,S)-4-(4-(trifluoromethyl)phenyl)-6,7-dihydro-5H-cyclopenta[c]pyridin-7-yl)propanamide (example 52) on a Chiralpak AD column (40% ethanol in n-heptane) to give after precipitation from $CH_2Cl_2$ with n-pentane 36% of (−)-(R)-2-hydroxy-N—((S or R)-4-(4-(trifluoromethyl)phenyl)-6,7-dihydro-5H-cyclopenta[c]pyridin-7-yl)propanamide (example 53) as off-white solid, MS: 351.1 (M+H$^+$) and 36% of (+)-(R)-2-hydroxy-N—((R or S)-4-(4-(trifluoromethyl)phenyl)-6,7-dihydro-5H-cyclopenta[c]pyridin-7-yl)propanamide (example 54) as light grey solid. MS: 351.1 (M+H$^+$).

Example 55

(rac)-N-(4-(4-Chloro-3-fluorophenyl)-6,7-dihydro-5H-cyclopenta[c]pyridin-7-yl)propionamide

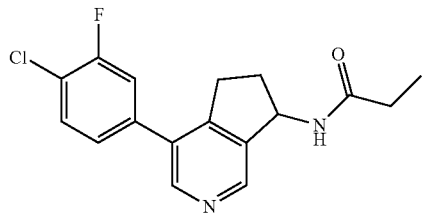

In analogy to the procedure described for the preparation of example 1, (rac)-N-(4-bromo-6,7-dihydro-5H-cyclopenta[c]pyridin-7-yl)propionamide (intermediate A-4) was reacted with 4-chloro-3-fluorophenylboronic acid to give the title compound as grey solid in 87% yield. MS: 319.1 (M+H$^+$, 1Cl).

Example 56 and Example 57

(−)-(S or R)—N-(4-(4-Chloro-3-fluorophenyl)-6,7-dihydro-5H-cyclopenta[c]pyridin-7-yl)propionamide and (+)-(R or S)—N-(4-(4-Chloro-3-fluorophenyl)-6,7-dihydro-5H-cyclopenta[c]pyridin-7-yl)propionamide Example 56

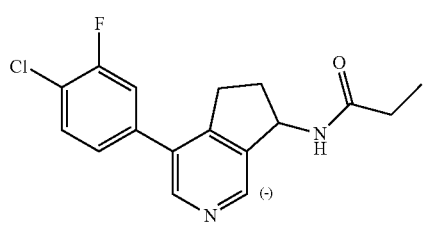 [SMILES: CCC(=O)NC1CCc2c(-c3ccc(Cl)c(F)c3)cncc21]

-continued

Example 57

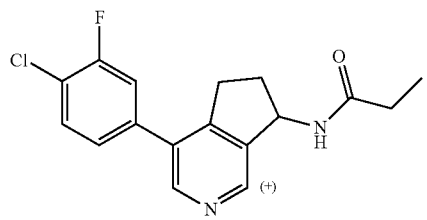

The title compounds were prepared by chiral separation of (rac)-N-(4-(4-chloro-3-fluorophenyl)-6,7-dihydro-5H-cyclopenta[c]pyridin-7-yl)propionamide (example 55) on a Reprosil Chiral NR column (15% 2-propanol in n-heptane) to give after precipitation from $CH_2Cl_2$ with n-pentane 41% of (−)-(S or R)—N-(4-(4-chloro-3-fluorophenyl)-6,7-dihydro-5H-cyclopenta[c]pyridin-7-yl)propionamide (example 56) as white solid, MS: 319.1 (M+H$^+$, 1Cl) and 43% of (+)-(R or S)—N-(4-(4-chloro-3-fluorophenyl)-6,7-dihydro-5H-cyclopenta[c]pyridin-7-yl)propionamide (example 57) as white solid. MS: 319.1 (M+H$^+$, 1Cl).

Example 58

(rac)-N-(4-(4-Fluoro-3-methylphenyl)-6,7-dihydro-5H-cyclopenta[c]pyridin-7-yl)propionamide

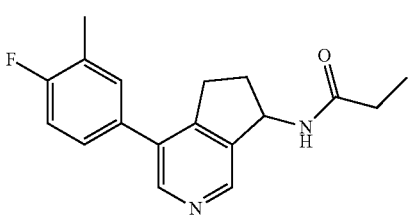 [SMILES: CCC(=O)NC1CCc2c(-c3ccc(F)c(C)c3)cncc21]

In analogy to the procedure described for the preparation of example 1, (rac)-N-(4-bromo-6,7-dihydro-5H-cyclopenta[c]pyridin-7-yl)propionamide (intermediate A-4) was reacted with 4-fluoro-3-methylphenylboronic acid to give the title compound as grey solid in 86% yield. MS: 299.2 (M+H$^+$).

Example 59 and Example 60

(−)-(S or R)—N-(4-(4-Fluoro-3-methylphenyl)-6,7-dihydro-5H-cyclopenta[c]pyridin-7-yl)propionamide and (+)-(R or S)—N-(4-(4-Fluoro-3-methylphenyl)-6,7-dihydro-5H-cyclopenta[c]pyridin-7-yl)propionamide Example 59

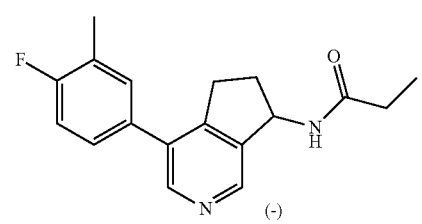

Example 60

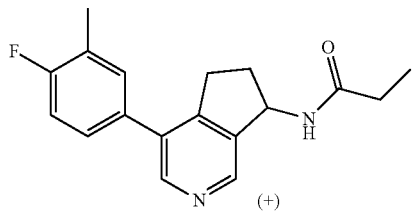

The title compounds were prepared by chiral separation of (rac)-N-(4-(4-fluoro-3-methylphenyl)-6,7-dihydro-5H-cyclopenta[c]pyridin-7-yl)propionamide (example 58) on a Reprosil Chiral NR column (15% ethanol in n-heptane) to give after precipitation from CH$_2$Cl$_2$ with n-pentane 40% of (−)-(S or R)—N-(4-(4-fluoro-3-methylphenyl)-6,7-dihydro-5H-cyclopenta[c]pyridin-7-yl)propionamide (example 59) as white solid, MS: 299.2 (M+H$^+$) and 40% of (+)-(R or S)—N-(4-(4-fluoro-3-methylphenyl)-6,7-dihydro-5H-cyclopenta[c]pyridin-7-yl)propionamide (example 60) as white solid. MS: 299.2 (M+H$^+$).

Example 61

(rac)-N-(4-(2-Fluoro-4-(trifluoromethyl)phenyl)-6,7-dihydro-5H-cyclopenta[c]pyridin-7-yl)propionamide

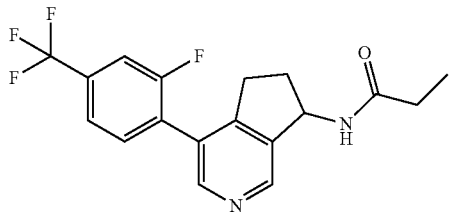

In analogy to the procedure described for the preparation of example 1, (rac)-N-(4-bromo-6,7-dihydro-5H-cyclopenta[c]pyridin-7-yl)propionamide (intermediate A-4) was reacted with 2-fluoro-4-(trifluoromethyl)phenylboronic acid to give the title compound as grey solid in 76% yield. MS: 353.1 (M+H$^+$).

Example 62 and Example 63

(−)-(S or R)—N-(4-(2-Fluoro-4-(trifluoromethyl)phenyl)-6,7-dihydro-5H-cyclopenta[c]pyridin-7-yl)propionamide and (+)-(R or S)—N-(4-(2-Fluoro-4-(trifluoromethyl)phenyl)-6,7-dihydro-5H-cyclopenta[c]pyridin-7-yl)propionamide Example 62

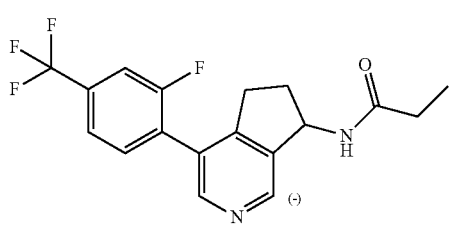

Example 63

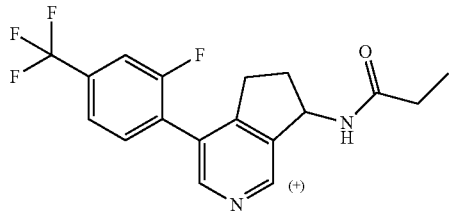 [SMILES: CCC(=O)NC1CCc2c(-c3ccc(C(F)(F)F)cc3F)cncc21]

The title compounds were prepared by chiral separation of (rac)-N-(4-(2-fluoro-4-(trifluoromethyl)phenyl)-6,7-dihydro-5H-cyclopenta[c]pyridin-7-yl)propionamide (example 61) on a Chiralpak AD column (15% ethanol in n-heptane) to give after precipitation from CH$_2$Cl$_2$ with n-pentane 40% of (−)-(S or R)—N-(4-(2-fluoro-4-(trifluoromethyl)phenyl)-6,7-dihydro-5H-cyclopenta[c]pyridin-7-yl)propionamide (example 62) as off-white solid, MS: 353.1 (M+H$^+$) and 40% of (+)-(R or S)—N-(4-(2-fluoro-4-(trifluoromethyl)phenyl)-6,7-dihydro-5H-cyclopenta[c]pyridin-7-yl)propionamide (example 63) as off-white solid. MS: 353.1 (M+H$^+$).

Example 64

(rac)-N-(4-(4-(Trifluoromethyl)phenyl)-6,7-dihydro-5H-cyclopenta[c]pyridin-7-yl)ethanesulfonamide

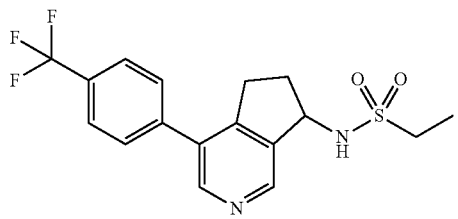 [SMILES: CCS(=O)(=O)NC1CCc2c(-c3ccc(C(F)(F)F)cc3)cncc21]

In analogy to the procedure described for the preparation of example 1, (rac)-N-(4-bromo-6,7-dihydro-5H-cyclopenta[c]pyridin-7-yl)ethanesulfonamide (intermediate A-7) was reacted with 4-(trifluoromethyl)phenylboronic acid to give the title compound as grey solid in 79% yield. MS: 371.1 (M+H$^+$).

Example 65 and Example 66

(−)-(S or R)—N-(4-(4-(Trifluoromethyl)phenyl)-6,7-dihydro-5H-cyclopenta[c]pyridin-7-yl)ethanesulfonamide and (+)-(R or S)—N-(4-(4-(Trifluoromethyl)phenyl)-6,7-dihydro-5H-cyclopenta[c]pyridin-7-yl)ethanesulfonamide Example 65

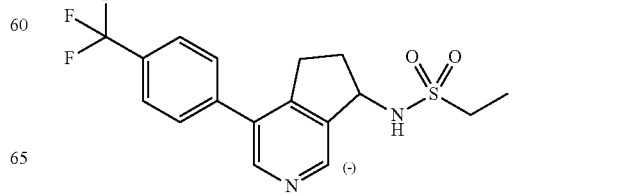

-continued

Example 66

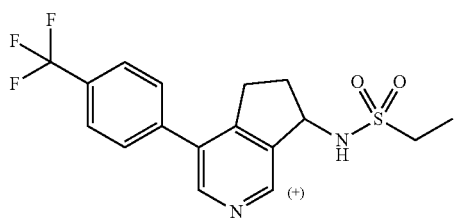

The title compounds were prepared by chiral separation of (rac)-N-(4-(4-(trifluoromethyl)phenyl)-6,7-dihydro-5H-cyclopenta[c]pyridin-7-yl)ethanesulfonamide (example 64) first on a Chiralpak AD column (40% ethanol in n-heptane) to give after precipitation from CH$_2$Cl$_2$ with n-pentane 22% of (−)-(S or R)—N-(4-(4-(trifluoromethyl)phenyl)-6,7-dihydro-5H-cyclopenta[c]pyridin-7-yl)ethanesulfonamide (example 65) as off-white solid, MS: 371.1 (M+H$^+$). The second isomer had to be repurified with a Lux 5u Cellulose-2 comun (20% ethanol in n-heptane) to give 5% of (+)-(R or S)—N-(4-(4-(trifluoromethyl)phenyl)-6,7-dihydro-5H-cyclopenta[c]pyridin-7-yl)ethanesulfonamide (example 66) as off-white solid. MS: 371.1 (M+H$^+$).

Example 67

N-[(7R,8S or 7S,8R)-7-Methyl-4-(4-trifluoromethyl-phenyl)-5,6,7,8-tetrahydro-isoquinolin-8-yl]-propionamide

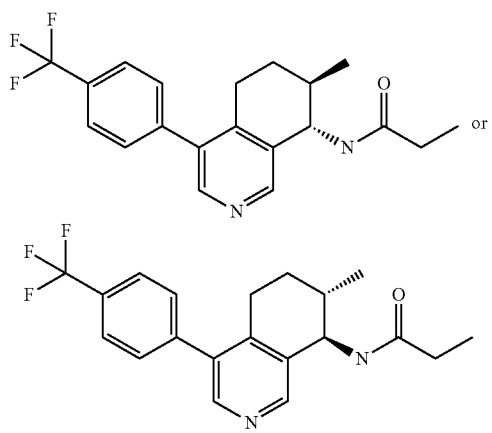

A mixture of N-((7R,8S or 7S,8R)-4-bromo-7-methyl-5,6,7,8-tetrahydro-isoquinolin-8-yl)-propion-amide (50 mg, 0.168 mmol) (intermediate A-9a), 4-trifluoromethylphenylboronic acid (40 mg, 0.202 mmol) in DMF (1.5 mL) was purged with argon for 1 min before bis(triphenylphosphine)palladium (II)chloride (12 mg, 0.017 mmol) and 2N aq. Na$_2$CO$_3$ solution (0.168 mL, 0.336 mmol) were added. The resulting reaction mixture was purged with argon for 2 min and then heated at 100° C. for 30 min in a microwave. After cooling to room temperature, the reaction mixture was diluted with EtOAc (5 mL), filtered through Dicalite and washed with water/EtOAc (2×). The resulting filtrate was washed with brine, dried over Na$_2$SO$_4$, filtered and evaporated to dryness. The crude product was then purified by Prep-HPLC to give the title compound (20 mg, 32.9%) as a white foam. MS: 363.1 (M+H)$^+$.

Example 68

N-[(7S,8S or 7R,8R)-7-Methyl-4-(4-trifluoromethyl-phenyl)-5,6,7,8-tetrahydro-isoquinolin-8-yl]-propionamide

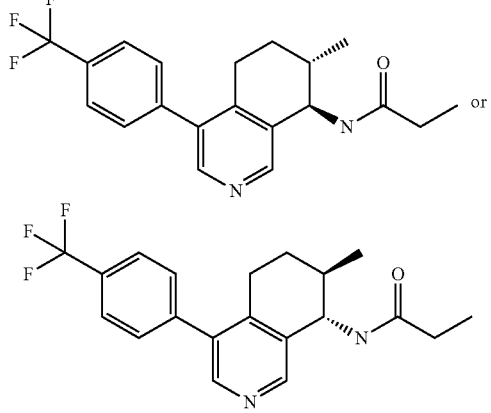

In analogy to the procedure described for the preparation of example 67, N-((7S,8S or 7R,8R)-4-bromo-7-methyl-5,6,7,8-tetrahydro-isoquinolin-8-yl)-propionamide (intermediate A-9b) and 4-trifluoromethylphenylboronic acid afforded the title compound as a white foam in 28% yield. MS: 363.1 (M+H)$^+$.

Example 69

N-[(7S,8R or 7R,8S)-7-Methyl-4-(4-trifluoromethyl-phenyl)-5,6,7,8-tetrahydro-isoquinolin-8-yl]-propionamide In analogy to the procedure described for the preparation of example 67, N-((7S,8R or 7R,8S)-4-bromo-7-methyl-5,6,7,8-tetrahydro-isoquinolin-8-yl)-propionamide (intermediate A-9c) and 4-trifluoromethylphenylboronic acid afforded the title compound as a white foam in 22% yield. MS: 363.1 (M+H)+.

Example 70

N-[(7R,8R or 7S,8S)-7-Methyl-4-(4-trifluoromethyl-phenyl)-5,6,7,8-tetrahydro-isoquinolin-8-yl]-propionamide

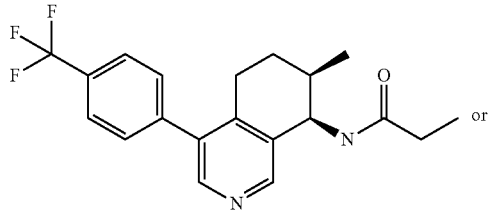

or

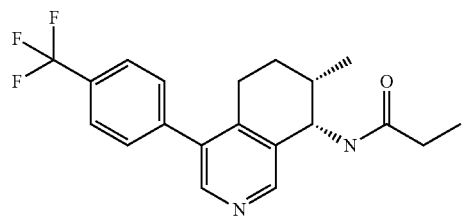

In analogy to the procedure described for the preparation of example 67, N-((7R,8R or 7S,8S)-4-bromo-7-methyl-5,6,7,8-tetrahydro-isoquinolin-8-yl)-propionamide (intermediate A-9d) and 4-trifluoromethylphenylboronic acid afforded the title compound as a white foam in 29% yield. MS: 363.1 (M+H)+.

Example 71

(rac)-N-(4-(3-Fluoro-4-(trifluoromethyl)phenyl)-6,7-dihydro-5H-cyclopenta[c]pyridin-7-yl)ethane-sulfonamide

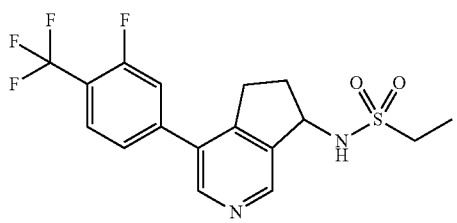

In analogy to the procedure described for the preparation of example 1, (rac)-N-(4-bromo-6,7-dihydro-5H-cyclopenta[c]pyridin-7-yl)ethanesulfonamide (intermediate A-7) was reacted with 3-fluoro-4-(trifluoromethyl)phenylboronic acid to give the title compound as off-white solid in 72% yield. MS: 389.1 (M+H+).

Example 72 and Example 73

(−)-(S or R)—N-(4-(3-Fluoro-4-(trifluoromethyl)phenyl)-6,7-dihydro-5H-cyclopenta[c]pyridin-7-yl)ethanesulfonamide and (+)-(R or S)—N-(4-(3-Fluoro-4-(trifluoromethyl)phenyl)-6,7-dihydro-5H-cyclopenta[c]pyridin-7-yl)ethanesulfonamide Example 72

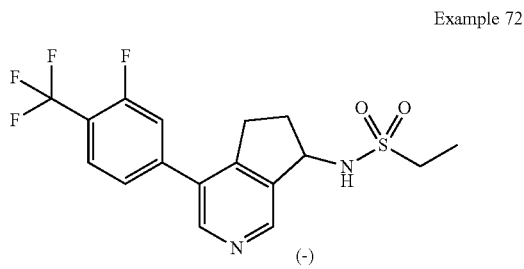

Example 73

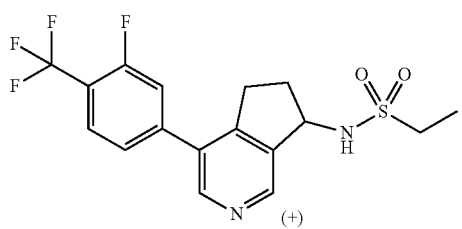

The title compounds were prepared by chiral separation of (rac)-N-(4-(3-fluoro-4-(trifluoromethyl)phenyl)-6,7-dihydro-5H-cyclopenta[c]pyridin-7-yl)ethanesulfonamide (example 71) on a Chiralpak IC [n-heptane/(EtOH+0.1% N,N-diethyl-amine) 70/30] to give 42% of (−)-(S or R)—N-(4-(3-fluoro-4-(trifluoromethyl)phenyl)-6,7-dihydro-5H-cyclopenta[c]pyridin-7-yl)ethanesulfonamide (example 72) as white solid, MS: 389.1 (M+H+) and 42% of (+)-(R or S)—N-(4-(3-fluoro-4-(trifluoromethyl)phenyl)-6,7-dihydro-5H-cyclopenta[c]pyridin-7-yl)ethanesulfonamide (example 73) as white solid. MS: 389.1 (M+H+).

Example 74

(+)-(R)-4-(2-Fluoro-4-(trifluoromethyl)phenyl)-5,6,7,8-tetrahydroisoquinolin-8-amine

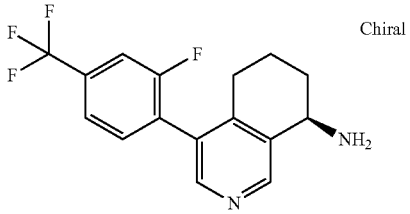 [SMILES: N[C@@H]1CCCc2c(-c3ccc(C(F)(F)F)cc3F)cncc21]

In analogy to the procedure described for the preparation of example 1, (+)-(R)-4-bromo-5,6,7,8-tetrahydroisoquinolin-8-amine (intermediate A-11) was reacted with 2-fluoro-4-

(trifluoromethyl)phenylboronic acid to give the title compound as brown viscous oil in 55% yield. MS: 311.1 (M+H⁺).

Example 75

(+)-(R)—N-(4-(2-Fluoro-4-(trifluoromethyl)phenyl)-5,6,7,8-tetrahydroisoquinolin-8-yl)acetamide

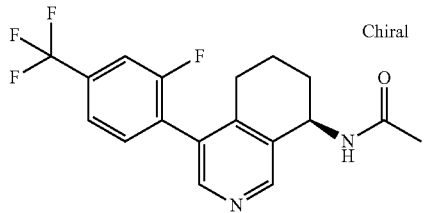 [SMILES: CC(=O)N[C@@H]1CCCc2c(-c3ccc(C(F)(F)F)cc3F)cncc21]

In analogy to the procedure described for the preparation of intermediate A-4 [D], (+)-(R)-4-(2-fluoro-4-(trifluoromethyl)phenyl)-5,6,7,8-tetrahydroisoquinolin-8-amine (example 74) and acetic acid gave the title compound as off-white amorphous solid in 90% yield. MS: 353.1 (M+H⁺).

Example 76

(+)-(R)—N-(4-(2-Fluoro-4-(trifluoromethyl)phenyl)-5,6,7,8-tetrahydroisoquinolin-8-yl)methanesulfonamide

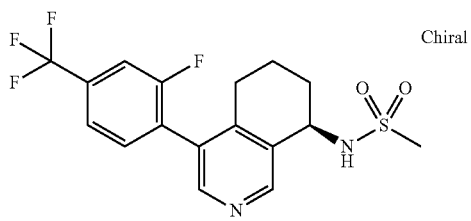 [SMILES: CS(=O)(=O)N[C@@H]1CCCc2c(-c3ccc(C(F)(F)F)cc3F)cncc21]

In analogy to the procedure described for the preparation of example 2, (+)-(R)-4-(2-fluoro-4-(trifluoromethyl)phenyl)-5,6,7,8-tetrahydroisoquinolin-8-amine (example 74) and methanesulfonyl chloride gave the title compound as white solid in 60% yield. MS: 389.1 (M+H⁺).

Example 77

(+)-(R)—N-(4-(4-(Trifluoromethyl)phenyl)-5,6,7,8-tetrahydroisoquinolin-8-yl)acetamide

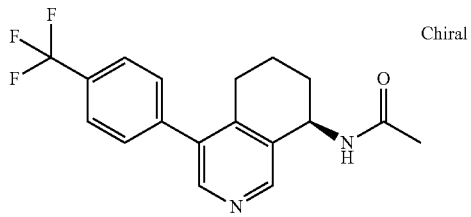 [SMILES: CC(=O)N[C@@H]1CCCc2c(-c3ccc(C(F)(F)F)cc3)cncc21]

In analogy to the procedure described for the preparation of example 1, (+)-(R)—N-(4-bromo-5,6,7,8-tetrahydroisoquinolin-8-yl)acetamide (intermediate A-12) was reacted with 4-(trifluoromethyl)phenylboronic acid to give the title compound as white solid in 87% yield. MS: 335.1 (M+H⁺).

Example 78

(+)-(R)—N-(4-(4-Cyanophenyl)-5,6,7,8-tetrahydroisoquinolin-8-yl)acetamide

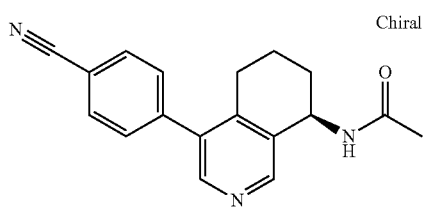 [SMILES: CC(=O)N[C@@H]1CCCc2c(-c3ccc(C#N)cc3)cncc21]

In analogy to the procedure described for the preparation of example 1, (+)-(R)—N-(4-bromo-5,6,7,8-tetrahydroisoquinolin-8-yl)acetamide (intermediate A-12) was reacted with 4-cyanophenylboronic acid to give the title compound as off-white solid in 87% yield. MS: 292.1 (M+H⁺).

Example 79

(+)-(R)—N-(4-(3-Fluoro-4-(trifluoromethyl)phenyl)-5,6,7,8-tetrahydroisoquinolin-8-yl)acetamide

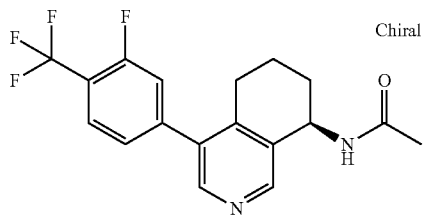 [SMILES: CC(=O)N[C@@H]1CCCc2c(-c3ccc(C(F)(F)F)c(F)c3)cncc21]

In analogy to the procedure described for the preparation of example 1, (+)-(R)—N-(4-bromo-5,6,7,8-tetrahydroisoquinolin-8-yl)acetamide (intermediate A-12) was reacted with 3-fluoro-4-(trifluoromethyl)phenylboronic acid to give the title compound as light grey solid in 83% yield. MS: 353.1 (M+H⁺).

Example 80

(rac)-4-(2-Fluoro-4-(trifluoromethyl)phenyl)-6,7-dihydro-5H-cyclopenta[c]pyridin-7-ol

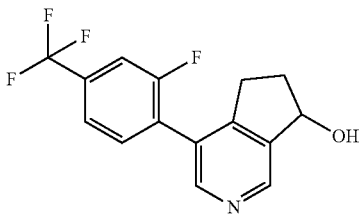 [SMILES: OC1CCc2c(-c3ccc(C(F)(F)F)cc3F)cncc21]

In analogy to the procedure described for the preparation of example 1 (rac)-4-bromo-6,7-dihydro-5H-cyclopenta[c]pyridin-7-ol (intermediate A-4 [C2]) was reacted with 2-fluoro-4-(trifluoromethyl)phenylboronic acid to give the title compound as brown viscous oil in 42% yield. MS: 298.1 (M+H+).

Example 81

(rac)-4-(7-Hydroxy-6,7-dihydro-5H-cyclopenta[c]pyridin-4-yl)benzonitrile

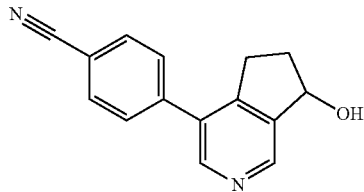 [SMILES: N#Cc1ccc(-c2cncc3c2CCC3O)cc1]

In analogy to the procedure described for the preparation of example 1 (rac)-4-bromo-6,7-dihydro-5H-cyclopenta[c]pyridin-7-ol (intermediate A-4 [C2]) was reacted with 4-cyanophenylboronic acid to give the title compound as brown viscous oil in 69% yield. MS: 237.1 (M+H+).

Example 82

(rac)-4-(3-Fluoro-4-(trifluoromethyl)phenyl)-6,7-dihydro-5H-cyclopenta[c]pyridin-7-ol

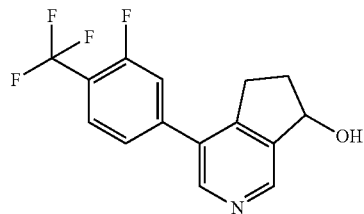 [SMILES: OC1CCc2c(-c3ccc(C(F)(F)F)c(F)c3)cncc21]

In analogy to the procedure described for the preparation of example 1 (rac)-4-bromo-6,7-dihydro-5H-cyclopenta[c]pyridin-7-ol (intermediate A-4 [C2]) was reacted with 3-fluoro-4-(trifluoromethyl)phenylboronic acid to give the title compound as grey solid in 55% yield. MS: 298.1 (M+H+).

Example 83

(rac)-4-(4-(Trifluoromethyl)phenyl)-6,7-dihydro-5H-cyclopenta[c]pyridin-7-ol

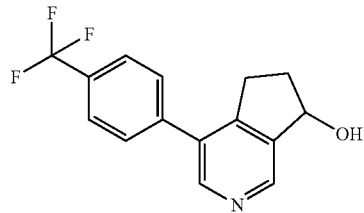 [SMILES: OC1CCc2c(-c3ccc(C(F)(F)F)cc3)cncc21]

In analogy to the procedure described for the preparation of example 1 (rac)-4-bromo-6,7-dihydro-5H-cyclopenta[c]pyridin-7-ol (intermediate A-4 [C2]) was reacted with 4-(trifluoromethyl)phenylboronic acid to give the title compound as grey solid in 97% yield. MS: 280.1 (M+H+).

Example 84

(rac)-7-Methyl-4-(4-(trifluoromethyl)phenyl)-6,7-dihydro-5H-cyclopenta[c]pyridin-7-ol

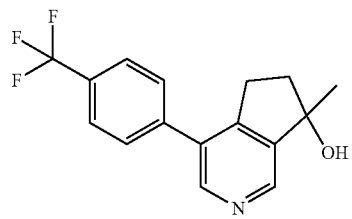 [SMILES: CC1(O)CCc2c(-c3ccc(C(F)(F)F)cc3)cncc21]

In analogy to the procedure described for the preparation of example 1 (rac)-4-bromo-7-methyl-6,7-dihydro-5H-cyclopenta[c]pyridin-7-ol (intermediate A-13) was reacted with 4-(trifluoromethyl)phenylboronic acid to give the title compound as grey solid in 85% yield. MS: 294.1 (M+H+)

Example 85 and Example 86

(+)-(7R or 7S)-6,6-Dimethyl-4-[4-(trifluoromethyl)phenyl]-5,7-dihydrocyclopenta[c]pyridin-7-ol and (−)-(7S or 7R)-6,6-Dimethyl-4-[4-(trifluoromethyl)phenyl]-5,7-dihydrocyclopenta[c]pyridin-7-ol Example 85

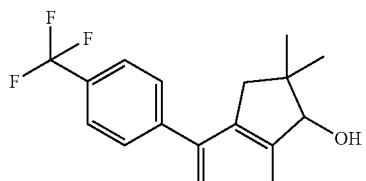

Example 86

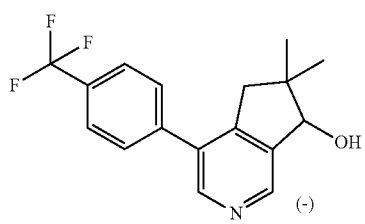

A mixture of 4-bromo-6,6-dimethyl-6,7-dihydro-5H-cyclopenta[c]pyridin-7-ol (intermediate A-17) (0.25 g, 1.03 mmol), 4-trifluoromethylphenylboronic acid (217 mg, 1.14 mmol), Pd(dppf)Cl$_2$ (25 mg, 0.1 mmol) and Cs$_2$CO$_3$ (1.01 g, 3.1 mmol) in dioxane/H$_2$O (12 mL, 5:1(v/v) was heated at 100° C. in a microwave reactor for 30 min. After cooling, the reaction mixture was extracted with EtOAc (15 mL×3), and the combined organic layers were dried over Na$_2$SO$_4$, filtered and concentrated in vacuo. The residue was purified by Prep. HPLC to give the two title compounds as a racemic mixture.

Subsequent separation by SFC (column: AD 250 mm*30 mm, 5 μm; mobile phase A: supercritical CO₂; mobile phase B: MeOH (0.05% Ammonia); A: B=60:40 at 50 mL/min) then gives two title enantiomers as white solids. MS: 307.9 (M+H⁺).

Example 87 and Example 88

(+)-4-[(7R or 7S)-7-Hydroxy-6,6-dimethyl-5,7-dihydrocyclopenta[c]pyridin-4-yl]benzonitrile and (−)-4-[(7S or 7R)-7-Hydroxy-6,6-dimethyl-5,7-dihydrocyclopenta[c]pyridin-4-yl]benzonitrile

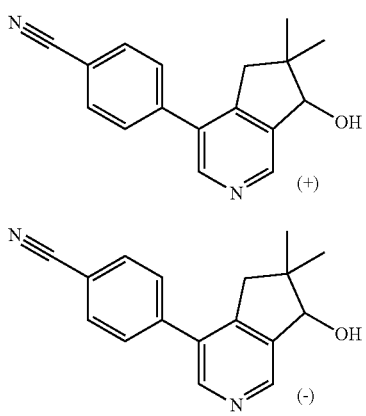

Example 87

Example 88

In analogy to the procedure described for the preparation of examples 85 and 86, 4-bromo-6,6-dimethyl-6,7-dihydro-5H-cyclopenta[c]pyridin-7-ol (intermediate A-17) and 4-cyanophenylboronic acid gave racemic 4-[7-hydroxy-6,6-dimethyl-5,7-dihydrocyclopenta[c]pyridin-4-yl]benzonitrile. SFC separation afforded (+)-4-[(7R or 7S)-7-hydroxy-6,6-dimethyl-5,7-dihydrocyclopenta[c]pyridin-4-yl]benzonitrile (example 87) and (−)-4-[(7S or 7R)-7-hydroxy-6,6-dimethyl-5,7-dihydrocyclopenta[c]pyridin-4-yl]benzonitrile (example 88) as white solids. MS: 264.9 (M+H⁺).

Example 89

(rac)-4-(3-Fluoro-4-trifluoromethyl-phenyl)-6,7-dihydro-5H-[2]pyrindin-7-ylamine

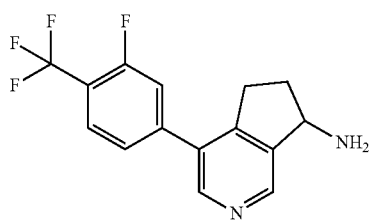 [SMILES: NC1CCc2c(-c3ccc(C(F)(F)F)c(F)c3)cncc21]

A solution of ammonium acetate (117 mg, 1.52 mmol) in MeOH (1 mL) was treated with 4-(3-fluoro-4-trifluoromethyl-phenyl)-5,6-dihydro-[2]pyrindin-7-one (intermediate A-14 [C1]) (15 mg, 0.051 mmol) dissolved in ethanol (0.5 mL) and the reaction mixture stirred at room temperature for 1 h. Sodium cyanoborohydride (11.2 mg, 0.18 mmol) was added and stirring continued at room temperature. After 15 min, the reaction mixture was heated to reflux for 30 min. The solvent was removed under reduced pressure, a sat. aq. solution of ammonium chloride (2 mL) and a 1 M solution of HCl (1 mL) were added and the aq. phase washed with dichloromethane (3×5 mL). To the aq. phase was added a 1 M solution of NaOH (2 mL) and extracted with dichloromethane (3×5 mL). The combined organic phases were dried over MgSO₄ and concentrated under reduced pressure. The title compound was isolated as light brown solid (3.8 mg, 25%). MS: 297.4 (M+H)⁺.

Example 90

(rac)-N-(4-(3-Fluoro-4-(trifluoromethyl)phenyl)-6,7-dihydro-5H-cyclopenta[c]pyridin-7-yl)propionamide

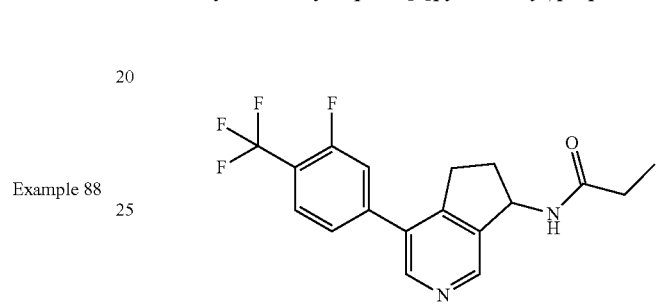

A solution of (rac)-4-(3-fluoro-4-trifluoromethyl-phenyl)-6,7-dihydro-5H-[2]pyrindin-7-ylamine (example 89) (40 mg, 0.14 mmol) and N,N-diisopropylethylamine (0.071 mL, 0.41 mmol) in DMF (0.5 mL) was treated with propionyl chloride (0.018 mL, 0.20 mmol) and the reaction mixture stirred at room temperature overnight. Purification by preparative HPLC on reversed phase eluting with a gradient of acetonitrile/water provided 4.0 mg (7%) of the title compound as a light brown oil. MS: 353.5 (M+H)⁺.

Example 91

(rac)-Cyclopropanesulfonic acid [4-(3-fluoro-4-trifluoromethyl-phenyl)-6,7-dihydro-5H-[2]pyrindin-7-yl]-amide

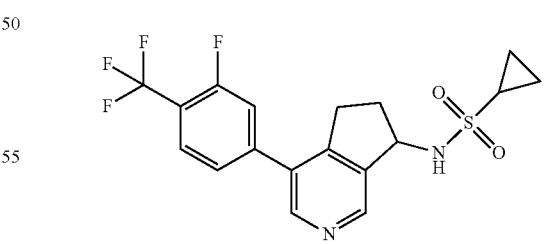

A solution of (rac)-4-(3-fluoro-4-trifluoromethyl-phenyl)-6,7-dihydro-5H-[2]pyrindin-7-ylamine (example 89) (40 mg, 0.14 mmol) and N,N-diisopropylethylamine (0.071 mL, 0.41 mmol) in DMF (0.5 mL) was treated with cyclopropanesulfonyl chloride (0.021 mL, 0.20 mmol) and the reaction mixture stirred at room temperature overnight. Purification by preparative HPLC on reversed phase eluting with a gradi-

Example 92

(rac)-Propionic acid 4-(3-fluoro-4-trifluoromethyl-phenyl)-6,7-dihydro-5H-[2]pyrindin-7-yl ester

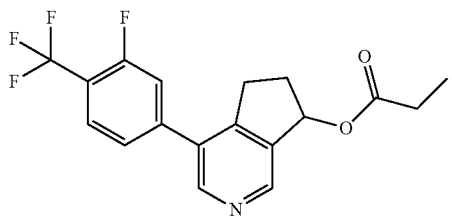 [SMILES: CCC(=O)OC1CCc2c(-c3ccc(C(F)(F)F)c(F)c3)cncc21]

A solution of (rac)-4-(3-fluoro-4-(trifluoromethyl)phenyl)-6,7-dihydro-5H-cyclopenta[c]pyridin-7-ol (example 82) (24 mg, 0.081 mmol) and N,N-diisopropylethylamine (0.028 mL, 0.162 mmol) in DMF (0.2 mL) was treated with propionyl chloride (0.021 mL, 0.243 mmol) and the reaction mixture stirred at room temperature. After 15 h, another aliquot of propionyl chloride (0.021 mL, 0.243 mmol) was added, the temperature increased to 50° C. and stirring continued for 2 h. The crude reaction mixture was poured into a 1 M solution of sodium hydroxide (10 mL) and extracted with ethyl acetate (2×15 mL). The combined organic extracts were washed with a sat. solution of sodium chloride (10 mL), dried (Na$_2$SO$_4$), and concentrated under reduced pressure. Purification by preparative HPLC on reversed phase eluting with a gradient of acetonitrile/water provided 3.2 mg (11%) of the title compound as a light brown solid. MS: 354.5 (M+H)$^+$.

Example 93

(rac)-4-(4-Trifluoromethyl-phenyl)-6,7-dihydro-5H-[2]pyrindin-7-ylamine

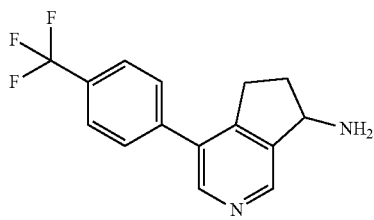 [SMILES: NC1CCc2c(-c3ccc(C(F)(F)F)cc3)cncc21]

In analogy to the procedure described for the preparation of (rac)-4-(3-fluoro-4-trifluoromethyl-phenyl)-6,7-dihydro-5H-[2]pyrindin-7-ylamine (example 89), replacing 4-(3-fluoro-4-trifluoromethyl-phenyl)-5,6-dihydro-[2]pyrindin-7-one with 4-(4-trifluoromethyl-phenyl)-5,6-dihydro-[2]pyrindin-7-one (intermediate A-15). The title compound was obtained as a light brown oil in 49% yield. MS: 279.5 (M+H)$^+$.

Example 94

(rac)-Cyclopropanesulfonic acid [4-(4-trifluoromethyl-phenyl)-6,7-dihydro-5H-[2]pyrindin-7-yl]-amide

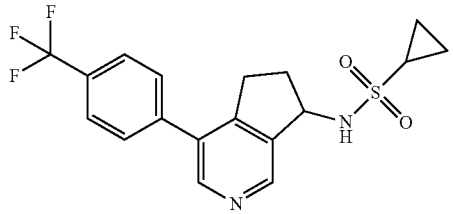 [SMILES: O=S(=O)(NC1CCc2c(-c3ccc(C(F)(F)F)cc3)cncc21)C1CC1]

In analogy to the procedure described for the preparation of (rac)-cyclopropanesulfonic acid [4-(3-fluoro-4-trifluoromethyl-phenyl)-6,7-dihydro-5H-[2]pyrindin-7-yl]-amide (example 91), replacing (rac)-4-(3-fluoro-4-trifluoromethyl-phenyl)-6,7-dihydro-5H-[2]pyrindin-7-ylamine with (rac)-4-(4-trifluoromethyl-phenyl)-6,7-dihydro-5H-[2]pyrindin-7-ylamine (example 93). The title compound was obtained as a light brown oil in 4% yield. MS: 383.4 (M+H)$^+$.

Example 95

(rac)-N-[4-(4-Trifluoromethyl-phenyl)-6,7-dihydro-5H-[2]pyrindin-7-yl]-methanesulfonamide

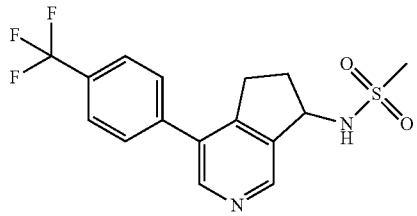 [SMILES: CS(=O)(=O)NC1CCc2c(-c3ccc(C(F)(F)F)cc3)cncc21]

In analogy to the procedure described for the preparation of (rac)-cyclopropanesulfonic acid [4-(4-trifluoromethyl-phenyl)-6,7-dihydro-5H-[2]pyrindin-7-yl]-amide (example 94), replacing cyclopropanesulfonyl chloride with methanesulfonyl chloride. The title compound was obtained as a light brown oil in 15% yield. MS: 357.4 (M+H)$^+$.

Example 96

(rac)-Propane-1-sulfonic acid [4-(4-trifluoromethyl-phenyl)-6,7-dihydro-5H-[2]pyrindin-7-yl]-amide

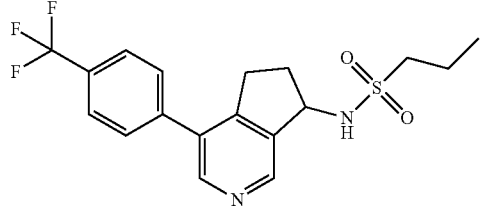 [SMILES: CCCS(=O)(=O)NC1CCc2c(-c3ccc(C(F)(F)F)cc3)cncc21]

In analogy to the procedure described for the preparation of (rac)-cyclopropanesulfonic acid [4-(4-trifluoromethyl-phenyl)-6,7-dihydro-5H-[2]pyrindin-7-yl]-amide (example 94), replacing cyclopropanesulfonyl chloride with propane-1-sulfonyl chloride. The title compound was obtained as a light brown oil in 5% yield. MS: 385.5 (M+H)+.

Example 97

(rac)-tert-Butyl 2-(4-(4-(trifluoromethyl)phenyl)-6,7-dihydro-5H-cyclopenta[c]pyridin-7-yloxy)acetate

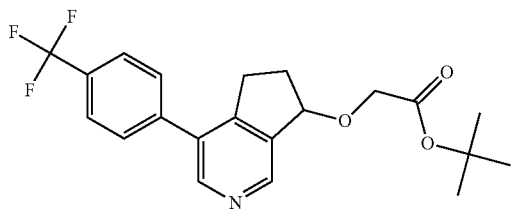 [SMILES: CC(C)(C)OC(=O)COC1CCc2c(-c3ccc(C(F)(F)F)cc3)cncc21]

A cooled (0° C.) solution of (rac)-4-(4-(trifluoromethyl)phenyl)-6,7-dihydro-5H-cyclopenta[c]pyridin-7-ol (example 83) (400 mg, 1.43 mmol) in DMF (4 mL) was treated with NaH (55% in oil, 100 mg, 2.29 mmol) and after ½ h with tert-butyl 2-bromoacetate (201 µL, 1.36 mmol) in DMF (4 mL). After warming up to room temperature overnight, the reaction mixture was poured on aq. 10% $KH_2PO_4$ solution followed by extraction with $Et_2O$ (3×). The organic phases were washed once with aq. 10% NaCl solution. The combined organic phases were dried ($Na_2SO_4$), filtered and purified by flash chromatography (50 g $SiO_2$, Telos-cartridge, 2% 2-propanol in $CH_2Cl_2$) to give the title compound (375 mg, 53%) as dark brown oil. MS: 394.2 (M+H+).

Example 98

(rac)-Methyl 2-(4-(4-(trifluoromethyl)phenyl)-6,7-dihydro-5H-cyclopenta[c]pyridin-7-yloxy)acetate

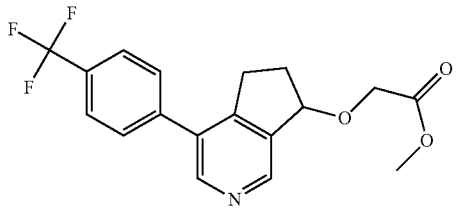 [SMILES: COC(=O)COC1CCc2c(-c3ccc(C(F)(F)F)cc3)cncc21]

To a cooled (0° C.) solution of (rac)-tert-butyl 2-(4-(4-(trifluoromethyl)phenyl)-6,7-dihydro-5H-cyclopenta[c]pyridin-7-yloxy)acetate (example 97) (102 mg, 0.26 mmol) in MeOH (4 mL) was added 4M HCl in dioxane (0.26 mL, 1.04 mmol) and the reaction mixture was stirred at room temperature for 16 h. The solution was cooled (0° C.) again and treated with 4M HCl in dioxane (0.39 mL, 1.56 mmol). After 1 h at room temperature, the solution was evaporated to dryness. The residue was suspended in EtOAc, filtered and dried to give the title compound (46 mg, 51%, 80% purity with 20% of corresponding acid) as a grey solid. MS: 352.5 (M+H+).

Example 99

(rac)-2-(4-(4-(Trifluoromethyl)phenyl)-6,7-dihydro-5H-cyclopenta[c]pyridin-7-yloxy)acetic acid hydrochloride

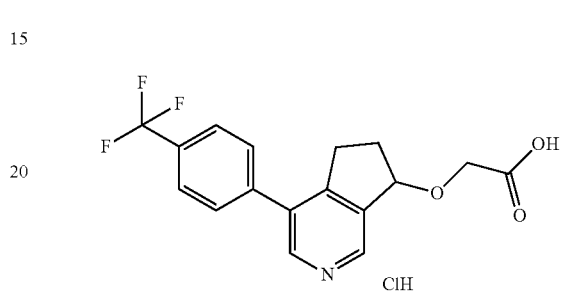

To a cooled (0° C.) solution of (rac)-tert-butyl 2-(4-(4-(trifluoromethyl)phenyl)-6,7-dihydro-5H-cyclopenta[c]pyridin-7-yloxy)acetate (example 97) (235 mg, 0.597 mmol) in $CH_2Cl_2$ (2 mL) was added 4M HCl in dioxane (1.49 mL, 5.97 mmol) and the reaction mixture was stirred at room temperature for 16 h. The mixture was evaporated to dryness to give the title compound (221 mg, 99%) as a grey solid. MS: 338.5 (M+H+).

Example 100

(rac)-N-Methyl-2-(4-(4-(trifluoromethyl)phenyl)-6,7-dihydro-5H-cyclopenta[c]pyridin-7-yloxy)acetamide

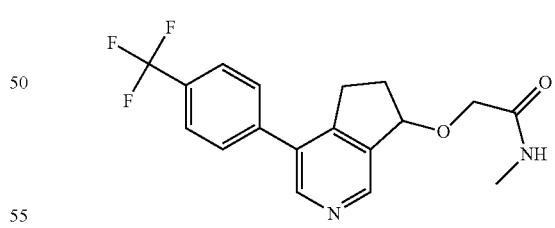

To a solution of (rac)-2-(4-(4-(trifluoromethyl)phenyl)-6,7-dihydro-5H-cyclopenta[c]pyridin-7-yloxy)acetic acid hydrochloride (example 99) (70 mg, 0.19 mmol) in THF (0.6 mL) was added N,N-diisopropylethylamine (131 µL, 0.75 mmol), 8M methylamine in EtOH (47 µL, 0.38 mmol) and 1-propanephosphonic acid cyclic anhydride (284 µL, 0.47 mmol). The reaction was stirred at room temperature for 16 h. The mixture was evaporated and purified by flash chromatography (20 g $SiO_2$, Telos-cartridge, 2 to 10% 2-propanol in

Example 101

(rac)-N,N-Dimethyl-2-(4-(4-(trifluoromethyl)phenyl)-6,7-dihydro-5H-cyclopenta[c]pyridin-7-yloxy)acetamide

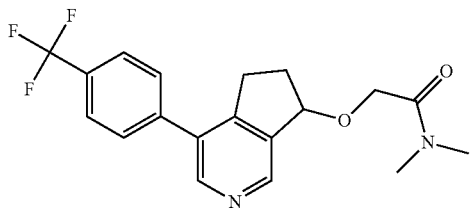 [SMILES: CN(C)C(=O)COC1CCc2c(-c3ccc(C(F)(F)F)cc3)cncc21]

To a solution of (rac)-2-(4-(4-(trifluoromethyl)phenyl)-6,7-dihydro-5H-cyclopenta[c]pyridin-7-yloxy)acetic acid hydrochloride (example 99) (70 mg, 0.19 mmol) in THF (0.6 mL) was added N,N-diisopropylethylamine (131 µL, 0.75 mmol), N,N-dimethylamine 33% solution in EtOH (67 µL, 0.38 mmol) and 1-propanephosphonic acid cyclic anhydride (284 µL, 0.47 mmol). The reaction was stirred at room temperature for 16 h. The mixture was evaporated and purified by flash chromatography (20 g SiO$_2$, Telos-cartridge, 4% 2-propanol in CH$_2$Cl$_2$) to give the title compound (49 mg, 72%) as yellow oil. MS: 365.6 (M+H$^+$).

Example 102

(rac)-2-(4-(4-(Trifluoromethyl)phenyl)-6,7-dihydro-5H-cyclopenta[c]pyridin-7-yloxy)acetamide

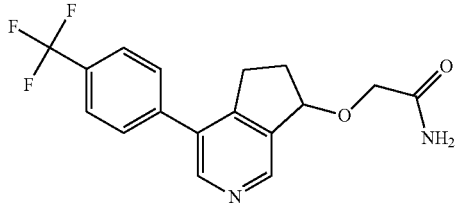 [SMILES: NC(=O)COC1CCc2c(-c3ccc(C(F)(F)F)cc3)cncc21]

To a solution of (rac)-2-(4-(4-(trifluoromethyl)phenyl)-6,7-dihydro-5H-cyclopenta[c]pyridin-7-yloxy)acetic acid hydrochloride (example 99) (34.6 mg, 0.093 mmol) in DMF (1 mL) was added N,N-triethylamine (31 µL, 0.22 mmol) and 1,1'-carbonyldiimidazole (18.0 mg, 0.11 mmol). The reaction was stirred at room temperature for 2 h, cooled (0°) and treated with aq. 25% ammonia solution (0.87 mL, 5.55 mmol) and evaporated after 30 min to give a 1:1 mixture of starting material and product. The residue was dissolved in CH$_2$Cl$_2$, dried (Na$_2$SO$_4$) and evaporated. The oil was again dissolved in DMF (1 mL) and N,N-triethylamine (15.5 µL, 0.11 mmol) and 1,1'-carbonyldiimidazole (18.0 mg, 0.11 mmol) were added. The reaction was stirred at room temperature for 2 h, cooled (0°) and treated with aq. 25% ammonia solution (0.87 mL, 5.55 mmol) and evaporated after 30 min at room temperature. The solution was evaporated, dried in vacuo and purified by flash chromatography (20 g SiO$_2$, Telos-cartridge, 3% MeOH in CH$_2$Cl$_2$) to give the title compound (15 mg, 48%) as off-white solid. MS: 337.1 (M+H$^+$).

Example 103

(rac)-7-((3-Methyloxetan-3-yl)methoxy)-4-(4-(trifluoromethyl)phenyl)-6,7-dihydro-5H-cyclopenta[c]pyridine

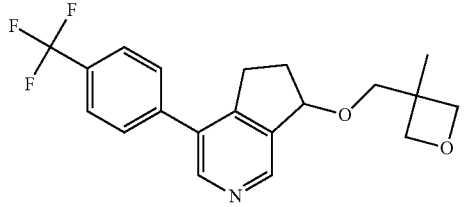 [SMILES: CC1(COC2CCc3c(-c4ccc(C(F)(F)F)cc4)cncc32)COC1]

A cooled (0° C.) solution of (rac)-4-(4-(trifluoromethyl)phenyl)-6,7-dihydro-5H-cyclopenta[c]pyridin-7-ol (example 83) (75 mg, 0.27 mmol) in DMF (1.4 mL) was treated with NaH (55% in oil, 18.7 mg, 0.43 mmol) and after ½ h with 3-(iodomethyl)-3-methyloxetane (209 mg, 0.59 mmol, synthesized by refluxing 3-(chloromethyl)-3-methyloxetane with 5 eq. sodium iodide in acetone overnight) in DMF (1 mL). After warming up to room temperature over 5 h, the reaction mixture was poured on aq. 10% KH$_2$PO$_4$ solution followed by extraction with Et$_2$O (3×). The organic phases were washed once with aq. 10% NaCl solution. The combined organic phases were dried (Na$_2$SO$_4$), filtered and purified by flash chromatography (20 g SiO$_2$, Telos-cartridge, 1 to 3% 2-propanol in CH$_2$Cl$_2$) to give the title compound (28 mg, 29%) as brown oil. MS: 364.5 (M+H$^+$).

Example 104

(rac)-4-(4-(Trifluoromethyl)phenyl)-5,6,7,8-tetrahydroisoquinolin-8-ol

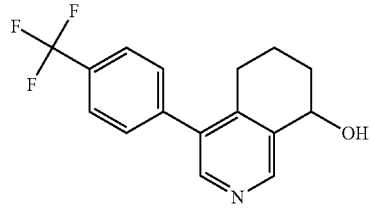

In analogy to the procedure described for the preparation of example 1 (rac)-4-bromo-5,6,7,8-tetrahydroisoquinolin-8-ol (intermediate A-2) was reacted with 4-(trifluoromethyl)phenylboronic acid to give the title compound as white solid in 86% yield. MS: 294.1 (M+H$^+$).

Example 105 and Example 106

(−)-(S or R)-4-(4-(Trifluoromethyl)phenyl)-5,6,7,8-tetrahydroisoquinolin-8-ol and (+)-(R or S)-4-(4-(Trifluoromethyl)phenyl)-5,6,7,8-tetrahydroisoquinolin-8-ol Example 105

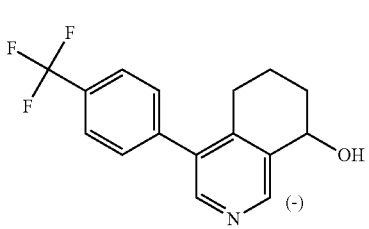 [SMILES: OC1CCCc2c(-c3ccc(C(F)(F)F)cc3)cncc21]

95

-continued

Example 106

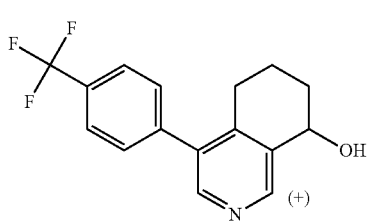

The title compounds were prepared by chiral separation of (rac)-4-(4-(trifluoromethyl)phenyl)-5,6,7,8-tetrahydroisoquinolin-8-ol (example 104) on a Chiralpak AD with 40% ethanol/n-heptane as eluent to give after precipitation from $CH_2Cl_2$ with n-pentane 44% of (+)-(R or S)-4-(4-(trifluoromethyl)phenyl)-5,6,7,8-tetrahydroisoquinolin-8-ol (example 106) as off-white solid, MS: 294.1 (M+H$^+$) and 45% of (−)-(S or R)-4-(4-(trifluoromethyl)phenyl)-5,6,7,8-tetrahydroisoquinolin-8-ol (example 105) as off-white solid. MS: 294.1 (M+H$^+$).

Example 107

(R)—N-(4-(2-Cyclopropyl-4-(trifluoromethyl)phenyl)-5,6,7,8-tetrahydroisoquinolin-8-yl)propionamide

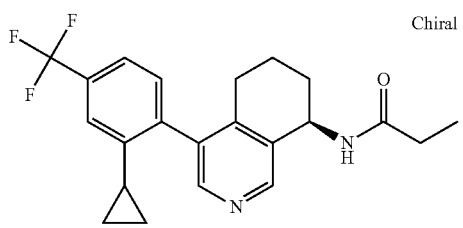 [SMILES: CCC(=O)N[C@@H]1CCCc2c(-c3ccc(C(F)(F)F)cc3C3CC3)cncc21]

In analogy to the procedure described for the preparation of example 1, (R)—N-(4-bromo-5,6,7,8-tetrahydroisoquinolin-8-yl)propionamide (intermediate A-16) was reacted with 4-trifluoromethyl-6-cyclopropylphenylboronic acid pinacol ester acid to give the title compound as colorless oil in 84% yield. MS: 389.2 (M+H$^+$).

Example 108 and Example 109

(+)-(7R or 7S)-4-[3-Fluoro-4-(trifluoromethyl)phenyl]-6,6-dimethyl-5,7-dihydrocyclopenta[c]-pyridin-7-ol and (−)-(7S or 7R)-4-[3-Fluoro-4-(trifluoromethyl)phenyl]-6,6-dimethyl-5,7-dihydrocyclopenta[c]-pyridin-7-ol

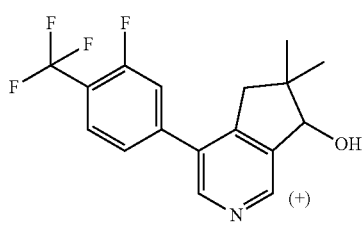

Example 108

96

-continued

Example 109

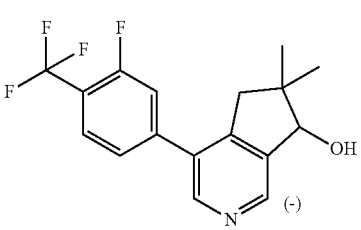

In analogy to the procedure described for the preparation of examples 85 and 86, 4-bromo-6,6-dimethyl-6,7-dihydro-5H-cyclopenta[c]pyridin-7-ol (intermediate A-17) and 3-fluoro-4-trifluoromethyl-phenylboronic acid gave racemic 4-[3-fluoro-4-(trifluoromethyl)phenyl]-6,6-dimethyl-5,7-dihydrocyclopenta[c]pyridin-7-ol. SFC separation afforded (+)-(7R)-4-[3-fluoro-4-(trifluoromethyl)phenyl]-6,6-dimethyl-5,7-dihydrocyclopenta[c]pyridin-7-ol (example 108) and (−)-(7S)-4-[3-fluoro-4-(trifluoromethyl)phenyl]-6,6-dimethyl-5,7-dihydrocyclopenta[c]-pyridin-7-ol (example 109) as white solids. MS: 309.0 (M+H$^+$).

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound of formula (I)

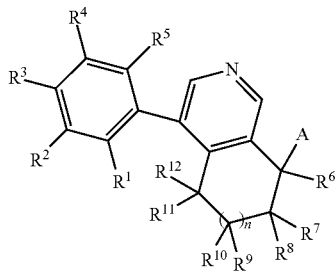

(I)

wherein $R^1$, $R^2$, $R^3$ and $R^4$ are independently selected from H, halogen, cyano, nitro, alkoxycarbonyl, cycloalkoxycarbonyl, substituted aminocarbonyl, substituted aminosulfonyl, alkyl, haloalkyl, cycloalkyl, alkoxy, haloalkoxy and cycloalkoxy, wherein substituted aminocarbonyl and substituted aminosulfonyl are substituted on the nitrogen atom with one to two substituents independently selected from H, alkyl, cycloalkyl, hydroxyalkyl and alkoxyalkyl;

$R^5$ is H, halogen, alkyl or cycloalkyl;

$R^6$ is H, alkyl, haloalkyl, cycloalkyl, substituted aryl or substituted heteroaryl, wherein substituted aryl or substituted heteroaryl are substituted with $R^{19}$, $R^{20}$ and $R^{21}$;

$R^7$, $R^8$, $R^9$, $R^{10}$, $R^{11}$ and $R^{12}$ are independently selected from H, halogen, alkyl and haloalkyl;

A is $-(CR^{13}R^{14})_p-NR^{15}R^{16}$ or $-(CR^{13}R^{14})_p-OR^{16}$;

$R^{13}$ and $R^{14}$ are independently selected from H, alkyl, haloalkyl, cycloalkyl and halocycloalkyl;

$R^{15}$ is H, alkyl, haloalkyl, cycloalkyl, hydroxyalkyl, alkoxyalkyl or haloalkoxyalkyl;

$R^{16}$ is H, alkyl, haloalkyl, cycloalkyl, hydroxyalkyl, alkoxyalkyl, haloalkoxyalkyl, oxetanylalkyl, $-CH_2-C(O)OH$, $-CH_2-C(O)OR^{17}$, $-CH_2-C(O)-NR^{17}R^{18}$, $-S(O)R^{17}$, $-S(O)_2R^{17}$, $-S(O)_2OR^{17}$, $-S(O)_2NR^{17}R^{18}$, $-C(O)R^{17}$, $-C(O)OR^{17}$ or $-C(O)NR^{17}R^{18}$;

$R^{17}$ is alkyl, hydroxyalkyl, haloalkyl, cycloalkyl, alkylcycloalkyl, alkylcycloalkylalkyl, cycloalkylalkyl, cycloalkoxyalkyl, cycloalkylalkoxyalkyl, alkoxyalkyl, haloalkoxyalkyl, alkoxyalkoxyalkyl or substituted heteroaryl, wherein substituted heteroaryl is substituted with $R^{22}$, $R^{23}$ and $R^{24}$;

$R^{18}$ is H, alkyl, haloalkyl, cycloalkyl, alkoxyalkyl, haloalkoxyalkyl or hydroxyalkyl;

$R^{19}$, $R^{20}$, $R^{21}$, $R^{22}$, $R^{23}$ and $R^{24}$ are independently selected from H, halogen, alkyl, haloalkyl, cycloalkyl, alkoxy and haloalkoxy;

n is zero, 1 or 2;

p is zero or 1;

or a pharmaceutically acceptable salt or ester thereof.

2. A compound of formula (I)

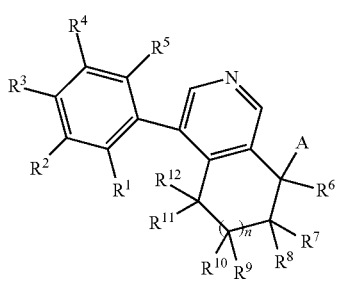

(I)

wherein $R^1$, $R^2$, $R^3$ and $R^4$ are independently selected from H, halogen, cyano, nitro, alkoxycarbonyl, cycloalkoxycarbonyl, substituted aminocarbonyl, substituted aminosulfonyl, alkyl, haloalkyl, cycloalkyl, alkoxy, haloalkoxy and cycloalkoxy, wherein substituted aminocarbonyl and substituted aminosulfonyl are substituted on the nitrogen atom with one to two substituents independently selected from H, alkyl, cycloalkyl, hydroxyalkyl and alkoxyalkyl;

$R^5$ is H, halogen, alkyl or cycloalkyl;

$R^6$ is H, alkyl, haloalkyl, cycloalkyl, substituted aryl or substituted heteroaryl, wherein substituted aryl or substituted heteroaryl are substituted with $R^{19}$, $R^{20}$ and $R^{21}$;

$R^7$, $R^8$, $R^9$, $R^{10}$, $R^{11}$ and $R^{12}$ are independently selected from H, halogen, alkyl and haloalkyl;

A is $-(CR^{13}R^{14})_p-NR^{15}R^{16}$ or $-(CR^{13}R^{14})_p-OR^{16}$;

$R^{13}$ and $R^{14}$ are independently selected from H, alkyl, haloalkyl, cycloalkyl and halocycloalkyl;

$R^{15}$ is H, alkyl, haloalkyl, cycloalkyl, hydroxyalkyl, alkoxyalkyl or haloalkoxyalkyl;

$R^{16}$ is H, alkyl, haloalkyl, cycloalkyl, hydroxyalkyl, alkoxyalkyl, haloalkoxyalkyl, $-S(O)R^{17}$, $-S(O)_2R^{17}$, $-S(O)_2OR^{17}$, $-S(O)_2NR^{17}R^{18}$, $-C(O)R^{17}$, $-C(O)OR^{17}$ or $-C(O)NR^{17}R^{18}$;

$R^{17}$ is alkyl, hydroxyalkyl, haloalkyl, cycloalkyl, alkylcycloalkyl, alkylcycloalkylalkyl, cycloalkylalkyl, cycloalkoxyalkyl, cycloalkylalkoxyalkyl, alkoxyalkyl, haloalkoxyalkyl, alkoxyalkoxyalkyl or substituted heteroaryl, wherein substituted heteroaryl is substituted with $R^{22}$, $R^{23}$ and $R^{24}$;

$R^{18}$ is H, alkyl, haloalkyl, cycloalkyl, alkoxyalkyl, haloalkoxyalkyl or hydroxyalkyl;

$R^{19}$, $R^{20}$, $R^{21}$, $R^{22}$, $R^{23}$ and $R^{24}$ are independently selected from H, halogen, alkyl, haloalkyl, cycloalkyl, alkoxy and haloalkoxy;

n is zero, 1 or 2;

p is zero or 1;

or a pharmaceutically acceptable salt or ester thereof.

3. A compound according to claim 1, wherein $R^1$, $R^2$, $R^3$ and $R^4$ are independently selected from H, halogen, cyano, alkyl and haloalkyl.

4. A compound according to claim 1, wherein $R^1$ is H or halogen.

5. A compound according to claim 1, wherein $R^2$ is H, alkyl or halogen.

6. A compound according to claim 1, wherein $R^2$ is H or halogen.

7. A compound according to claim 1, wherein $R^3$ is halogen, cyano or haloalkyl.

8. A compound according to claim 1, wherein $R^3$ is cyano or haloalkyl.

9. A compound according to claim 1, wherein $R^3$ is haloalkyl.

10. A compound according to claim 1, wherein $R^4$ is H or halogen.

11. A compound according to claim 1, wherein $R^4$ is H.

12. A compound according to claim 1, wherein $R^5$ is H.

13. A compound according to claim 1, wherein $R^6$ is H or aryl substituted with $R^{19}$, $R^{20}$ and $R^{21}$.

14. A compound according to claim 1, wherein $R^6$ is H.

15. A compound according to claim 1, wherein $R^7$, $R^8$, $R^9$, $R^{10}$, $R^{11}$ and $R^{12}$ are independently selected from H and alkyl.

16. A compound according to claim 1, wherein $R^7$ is H or alkyl.

17. A compound according to claim 1, wherein $R^8$, $R^9$, $R^{10}$, $R^{11}$ and $R^{12}$ are H.

18. A compound according to claim 1, wherein A is $-(CR^{13}R^{14})_p-NR^{15}R^{16}$.

19. A compound according to claim 1, wherein A is $-(CR^{13}R^{14})_p-OR^{16}$.

20. A compound according to claim 1, wherein $R^{15}$ is H.

21. A compound according to claim 1, wherein $R^{16}$ is H, alkyl, $-S(O)_2R^{17}$, $-S(O)_2NR^{17}R^{18}$, $-C(O)R^{17}$, $-C(O)OR^{17}$ or $-C(O)NR^{17}R^{18}$.

22. A compound according to claim 1, wherein A is —(CR$^{13}$R$^{14}$)$_p$—NR$^{15}$R$^{16}$, and R$^{16}$ is H, —S(O)$_2$R$^{17}$, —S(O)$_2$ NR$^{17}$R$^{18}$, C(O)R$^{17}$, —C(O)OR$^{17}$ or —C(O)NR$^{17}$R$^{18}$.

23. A compound according to claim 1, wherein A is —(CR$^{13}$R$^{14}$)$_p$—OR$^{16}$, and R$^{16}$ is H, alkyl or —C(O)NR$^{17}$R$^{18}$.

24. A compound according to claim 1, wherein R$^{16}$ is —S(O)$_2$R$^{17}$ or —C(O)R$^{17}$.

25. A compound according to claim 1, wherein R$^{16}$ is —C(O)R$^{17}$.

26. A compound according to claim 1, wherein R$^{16}$ is —S(O)$_2$R$^{17}$.

27. A compound according to claim 1, wherein R$^{17}$ is alkyl or hydroxyalkyl.

28. A compound according to claim 1, wherein R$^{18}$ is H.

29. A compound according to claim 1, wherein R$^{19}$, R$^{20}$ and R$^{21}$ are independently selected from H and alkyl.

30. A compound according to claim 1, wherein R$^{19}$ is H or alkyl.

31. A compound according to claim 1, wherein R$^{20}$ is H or alkyl.

32. A compound according to claim 1, wherein R$^{21}$ is H.

33. A compound according to claim 1, wherein n is zero or 1.

34. A compound according to claim 1, wherein n is zero.

35. A compound according to claim 1, wherein n is 1.

36. A compound according to claim 1, wherein p is 0.

37. A compound according to claim 1, selected from (rac)-4-(8-Amino-5,6,7,8-tetrahydroisoquinolin-4-yl)benzonitrile;
(rac)-N-(4-(4-Cyanophenyl)-5,6,7,8-tetrahydroisoquinolin-8-yl)ethanesulfonamide;
(rac)-N-[4-(4-Cyanophenyl)-5,6,7,8-tetrahydroisoquinolin-8-yl]-N'-propylsulfuric diamide;
(rac)-1-(4-(4-Cyanophenyl)-5,6,7,8-tetrahydroisoquinolin-8-yl)-3-ethylurea;
(rac)-N-(4-(4-Cyanophenyl)-5,6,7,8-tetrahydroisoquinolin-8-yl)propionamide;
(−)-(S or R)—N-(4-(4-Cyanophenyl)-5,6,7,8-tetrahydroisoquinolin-8-yl)propionamide;
(+)-(R or S)—N-(4-(4-Cyanophenyl)-5,6,7,8-tetrahydroisoquinolin-8-yl)propionamide;
(rac)-N-(4-(4-Cyanophenyl)-5,6,7,8-tetrahydroisoquinolin-8-yl)acetamide;
(rac)-N-(4-(4-Cyanophenyl)-5,6,7,8-tetrahydroisoquinolin-8-yl)isobutyramide;
(rac)-Ethyl 4-(4-cyanophenyl)-5,6,7,8-tetrahydroisoquinolin-8-ylcarbamate;
(rac)-4-(8-Hydroxy-5,6,7,8-tetrahydroisoquinolin-4-yl)benzonitrile;
(rac)-4-(4-Cyanophenyl)-5,6,7,8-tetrahydroisoquinolin-8-yl ethylcarbamate;
(rac)-4-(8-Methoxy-5,6,7,8-tetrahydroisoquinolin-4-yl)benzonitrile;
(rac)-4-(8-(3,4-Dimethylphenyl)-8-hydroxy-5,6,7,8-tetrahydroisoquinolin-4-yl)benzonitrile;
(+)-(S or R)-4-(8-(3,4-Dimethylphenyl)-8-hydroxy-5,6,7,8-tetrahydroisoquinolin-4-yl)benzonitrile;
(−)-(R or S)-4-(8-(3,4-Dimethylphenyl)-8-hydroxy-5,6,7,8-tetrahydroisoquinolin-4-yl)benzonitrile;
(rac)-N-(4-(4-Cyanophenyl)-6,7-dihydro-5H-cyclopenta[c]pyridin-7-yl)propionamide;
(−)-(S or R)—N-(4-(4-Cyanophenyl)-6,7-dihydro-5H-cyclopenta[c]pyridin-7-yl)propionamide;
(+)-(R or S)—N-(4-(4-Cyanophenyl)-6,7-dihydro-5H-cyclopenta[c]pyridin-7-yl)propionamide;
(rac)-N-(4-(3-Chloro-4-fluorophenyl)-5,6,7,8-tetrahydroisoquinolin-8-yl)propionamide;
(rac)-N-(4-(4-(Trifluoromethyl)phenyl)-5,6,7,8-tetrahydroisoquinolin-8-yl)propionamide;
(−)-(S or R)—N-(4-(4-(Trifluoromethyl)phenyl)-5,6,7,8-tetrahydroisoquinolin-8-yl)propionamide;
(+)-(R or S)—N-(4-(4-(Trifluoromethyl)phenyl)-5,6,7,8-tetrahydroisoquinolin-8-yl)propionamide;
(rac)-N-(4-(4-Chlorophenyl)-5,6,7,8-tetrahydroisoquinolin-8-yl)propionamide;
(−)-(S or R)—N-(4-(4-Chlorophenyl)-5,6,7,8-tetrahydroisoquinolin-8-yl)propionamide;
(+)-(R or S)—N-(4-(4-Chlorophenyl)-5,6,7,8-tetrahydroisoquinolin-8-yl)propionamide;
(rac)-N-(4-(4-Fluoro-3-methylphenyl)-5,6,7,8-tetrahydroisoquinolin-8-yl)propionamide;
(−)-(S or R)—N-(4-(4-Fluoro-3-methylphenyl)-5,6,7,8-tetrahydroisoquinolin-8-yl)propionamide;
(+)-(R or S)—N-(4-(4-Fluoro-3-methylphenyl)-5,6,7,8-tetrahydroisoquinolin-8-yl)propionamide;
(rac)-N-(4-(4-Chloro-2-fluorophenyl)-5,6,7,8-tetrahydroisoquinolin-8-yl)propionamide;
(−)-(S or R)—N-(4-(4-Chloro-2-fluorophenyl)-5,6,7,8-tetrahydroisoquinolin-8-yl)propionamide;
(+)-(R or S)—N-(4-(4-Chloro-2-fluorophenyl)-5,6,7,8-tetrahydroisoquinolin-8-yl)propionamide;
(rac)-N-(4-(2-Fluoro-4-(trifluoromethyl)phenyl)-5,6,7,8-tetrahydroisoquinolin-8-yl)propionamide;
(−)-(S or R)—N-(4-(2-Fluoro-4-(trifluoromethyl)phenyl)-5,6,7,8-tetrahydroisoquinolin-8-yl)propionamide;
(+)-(R or S)—N-(4-(2-Fluoro-4-(trifluoromethyl)phenyl)-5,6,7,8-tetrahydroisoquinolin-8-yl)propionamide;
(rac)-N-(4-(4-Chloro-3-fluorophenyl)-5,6,7,8-tetrahydroisoquinolin-8-yl)propionamide;
(−)-(S or R)—N-(4-(4-Chloro-3-fluorophenyl)-5,6,7,8-tetrahydroisoquinolin-8-yl)propionamide;
(+)-(R or S)—N-(4-(4-Chloro-3-fluorophenyl)-5,6,7,8-tetrahydroisoquinolin-8-yl)propionamide;
(rac)-N-(4-(3-Fluoro-4-(trifluoromethyl)phenyl)-5,6,7,8-tetrahydroisoquinolin-8-yl)propionamide;
(−)-(S or R)—N-(4-(3-Fluoro-4-(trifluoromethyl)phenyl)-5,6,7,8-tetrahydroisoquinolin-8-yl)propionamide;
(+)-(R or S)—N-(4-(3-Fluoro-4-(trifluoromethyl)phenyl)-5,6,7,8-tetrahydroisoquinolin-8-yl)propionamide;
(rac)-N-(4-(2,4-Difluorophenyl)-5,6,7,8-tetrahydroisoquinolin-8-yl)propionamide;
(rac)-N-(4-(2,4,5-Trifluorophenyl)-5,6,7,8-tetrahydroisoquinolin-8-yl)propionamide;
(rac)-N-(4-(3,4-Difluorophenyl)-5,6,7,8-tetrahydroisoquinolin-8-yl)propionamide;
(rac)-N-(4-(3,4-Dichlorophenyl)-5,6,7,8-tetrahydroisoquinolin-8-yl)propionamide;
(R)-2-Hydroxy-N—[(S,R)-4-(4-trifluoromethyl-phenyl)-5,6,7,8-tetrahydro-isoquinolin-8-yl]-propionamide;
(+)-(R)-2-Hydroxy-N—[(R or S)-4-(4-trifluoromethyl-phenyl)-5,6,7,8-tetrahydro-isoquinolin-8-yl]-propionamide;
(−)-(R)-2-Hydroxy-N—[(S or R)-4-(4-trifluoromethyl-phenyl)-5,6,7,8-tetrahydro-isoquinolin-8-yl]-propionamide;
(rac)-N-(4-(4-(Trifluoromethyl)phenyl)-6,7-dihydro-5H-cyclopenta[c]pyridin-7-yl)propionamide;
(−)-(S or R)—N-(4-(4-(Trifluoromethyl)phenyl)-6,7-dihydro-5H-cyclopenta[c]pyridin-7-yl)propionamide;
(+)-(R or S)—N-(4-(4-(Trifluoromethyl)phenyl)-6,7-dihydro-5H-cyclopenta[c]pyridin-7-yl)propionamide;

(R)-2-Hydroxy-N—((R,S)-4-(4-(trifluoromethyl)phenyl)-6,7-dihydro-5H-cyclopenta[c]pyridin-7-yl)propanamide;
(−)-(R)-2-Hydroxy-N—((S or R)-4-(4-(trifluoromethyl)phenyl)-6,7-dihydro-5H-cyclopenta[c]pyridin-7-yl) propanamide;
(+)-(R)-2-Hydroxy-N—((R or S)-4-(4-(trifluoromethyl)phenyl)-6,7-dihydro-5H-cyclopenta[c]pyridin-7-yl) propanamide;
(rac)-N-(4-(4-Chloro-3-fluorophenyl)-6,7-dihydro-5H-cyclopenta[c]pyridin-7-yl)propionamide;
(−)-(S or R)—N-(4-(4-Chloro-3-fluorophenyl)-6,7-dihydro-5H-cyclopenta[c]pyridin-7-yl)propionamide;
(+)-(R or S)—N-(4-(4-Chloro-3-fluorophenyl)-6,7-dihydro-5H-cyclopenta[c]pyridin-7-yl)propionamide;
(rac)-N-(4-(4-Fluoro-3-methylphenyl)-6,7-dihydro-5H-cyclopenta[c]pyridin-7-yl)propionamide;
(−)-(S or R)—N-(4-(4-Fluoro-3-methylphenyl)-6,7-dihydro-5H-cyclopenta[c]pyridin-7-yl)propionamide;
(+)-(R or S)—N-(4-(4-Fluoro-3-methylphenyl)-6,7-dihydro-5H-cyclopenta[c]pyridin-7-yl)propionamide;
(rac)-N-(4-(2-Fluoro-4-(trifluoromethyl)phenyl)-6,7-dihydro-5H-cyclopenta[c]pyridin-7-yl)propionamide;
(−)-(S or R)—N-(4-(2-Fluoro-4-(trifluoromethyl)phenyl)-6,7-dihydro-5H-cyclopenta[c]pyridin-7-yl)propionamide;
(+)-(R or S)—N-(4-(2-Fluoro-4-(trifluoromethyl)phenyl)-6,7-dihydro-5H-cyclopenta[c]pyridin-7-yl)propionamide;
(rac)-N-(4-(4-(Trifluoromethyl)phenyl)-6,7-dihydro-5H-cyclopenta[c]pyridin-7-yl)ethanesulfonamide;
(−)-(S or R)—N-(4-(4-(Trifluoromethyl)phenyl)-6,7-dihydro-5H-cyclopenta[c]pyridin-7-yl)ethanesulfonamide;
(+)-(R or S)—N-(4-(4-(Trifluoromethyl)phenyl)-6,7-dihydro-5H-cyclopenta[c]pyridin-7-yl)ethanesulfonamide;
N-[(7R,8S or 7S,8R)-7-Methyl-4-(4-trifluoromethyl-phenyl)-5,6,7,8-tetrahydro-isoquinolin-8-yl]-propionamide;
N-[(7S,8S or 7R,8R)-7-Methyl-4-(4-trifluoromethyl-phenyl)-5,6,7,8-tetrahydro-isoquinolin-8-yl]-propionamide;
N-[(7S,8R or 7R,8S)-7-Methyl-4-(4-trifluoromethyl-phenyl)-5,6,7,8-tetrahydro-isoquinolin-8-yl]-propionamide;
N-[(7R,8R or 7S,8S)-7-Methyl-4-(4-trifluoromethyl-phenyl)-5,6,7,8-tetrahydro-isoquinolin-8-yl]-propionamide;
or a pharmaceutically acceptable salt thereof.

38. A compound according to claim 1, selected from
(rac)-N-(4-(3-Fluoro-4-(trifluoromethyl)phenyl)-6,7-dihydro-5H-cyclopenta[c]pyridin-7-yl)ethanesulfonamide;
(−)-(S or R)—N-(4-(3-Fluoro-4-(trifluoromethyl)phenyl)-6,7-dihydro-5H-cyclopenta[c]pyridin-7-yl)ethanesulfonamide;
(+)-(R or S)—N-(4-(3-Fluoro-4-(trifluoromethyl)phenyl)-6,7-dihydro-5H-cyclopenta[c]pyridin-7-yl)ethanesulfonamide;
(+)-(R)-4-(2-Fluoro-4-(trifluoromethyl)phenyl)-5,6,7,8-tetrahydroisoquinolin-8-amine;
(+)-(R)—N-(4-(2-Fluoro-4-(trifluoromethyl)phenyl)-5,6,7,8-tetrahydroisoquinolin-8-yl)acetamide;
(+)-(R)—N-(4-(2-Fluoro-4-(trifluoromethyl)phenyl)-5,6,7,8-tetrahydroisoquinolin-8-yl)methanesulfonamide;
(+)-(R)—N-(4-(4-(Trifluoromethyl)phenyl)-5,6,7,8-tetrahydroisoquinolin-8-yl)acetamide;
(+)-(R)—N-(4-(4-Cyanophenyl)-5,6,7,8-tetrahydroisoquinolin-8-yl)acetamide;
(+)-(R)—N-(4-(3-Fluoro-4-(trifluoromethyl)phenyl)-5,6,7,8-tetrahydroisoquinolin-8-yl)acetamide;
(rac)-4-(2-Fluoro-4-(trifluoromethyl)phenyl)-6,7-dihydro-5H-cyclopenta[c]pyridin-7-ol;
(rac)-4-(7-Hydroxy-6,7-dihydro-5H-cyclopenta[c]pyridin-4-yl)benzonitrile;
(rac)-4-(3-Fluoro-4-(trifluoromethyl)phenyl)-6,7-dihydro-5H-cyclopenta[c]pyridin-7-ol;
(rac)-4-(4-(Trifluoromethyl)phenyl)-6,7-dihydro-5H-cyclopenta[c]pyridin-7-ol;
(rac)-7-methyl-4-(4-(Trifluoromethyl)phenyl)-6,7-dihydro-5H-cyclopenta[c]pyridin-7-ol;
(+)-(7R or 7S)-6,6-Dimethyl-4-[4-(trifluoromethyl)phenyl]-5,7-dihydrocyclopenta[c]pyridin-7-ol;
(−)-(7S or 7R)-6,6-Dimethyl-4-[4-(trifluoromethyl)phenyl]-5,7-dihydrocyclopenta[c]pyridin-7-ol;
(+)-4-[(7R or 7S)-7-Hydroxy-6,6-dimethyl-5,7-dihydrocyclopenta[c]pyridin-4-yl]benzonitrile;
(−)-4-[(7S or 7R)-7-Hydroxy-6,6-dimethyl-5,7-dihydrocyclopenta[c]pyridin-4-yl]benzonitrile;
(rac)-4-(3-Fluoro-4-trifluoromethyl-phenyl)-6,7-dihydro-5H-[2]pyrindin-7-ylamine;
(rac)-N-(4-(3-Fluoro-4-(trifluoromethyl)phenyl)-6,7-dihydro-5H-cyclopenta[c]pyridin-7-yl)propionamide;
(rac)-Cyclopropanesulfonic acid [4-(3-fluoro-4-trifluoromethyl-phenyl)-6,7-dihydro-5H-[2]pyrindin-7-yl]-amide;
(rac)-Propionic acid 4-(3-fluoro-4-trifluoromethyl-phenyl)-6,7-dihydro-5H-[2]pyrindin-7-yl ester;
(rac)-4-(4-(Trifluoromethyl)phenyl)-6,7-dihydro-5H-cyclopenta[c]pyridin-7-amine;
(rac)-N-(4-(4-(Trifluoromethyl)phenyl)-6,7-dihydro-5H-cyclopenta[c]pyridin-7-yl)cyclopropanesulfonamide;
(rac)-N-(4-(4-(Trifluoromethyl)phenyl)-6,7-dihydro-5H-cyclopenta[c]pyridin-7-yl)methanesulfonamide;
(rac)-N-(4-(4-(Trifluoromethyl)phenyl)-6,7-dihydro-5H-cyclopenta[c]pyridin-7-yl)propane-1-sulfonamide;
(rac)-tert-Butyl 2-(4-(4-(trifluoromethyl)phenyl)-6,7-dihydro-5H-cyclopenta[c]pyridin-7-yloxy)acetate;
(rac)-Methyl 2-(4-(4-(trifluoromethyl)phenyl)-6,7-dihydro-5H-cyclopenta[c]pyridin-7-yloxy)acetate;
(rac)-2-(4-(4-(Trifluoromethyl)phenyl)-6,7-dihydro-5H-cyclopenta[c]pyridin-7-yloxy)acetic acid hydrochloride;
(rac)-N-Methyl-2-(4-(4-(trifluoromethyl)phenyl)-6,7-dihydro-5H-cyclopenta[c]pyridin-7-yloxy)acetamide;
(rac)-N,N-Dimethyl-2-(4-(4-(trifluoromethyl)phenyl)-6,7-dihydro-5H-cyclopenta[c]pyridin-7-yloxy)acetamide;
(rac)-2-(4-(4-(Trifluoromethyl)phenyl)-6,7-dihydro-5H-cyclopenta[c]pyridin-7-yloxy)acetamide;
(rac)-7-(3-Methyloxetan-3-yl)methoxy)-4-(4-(trifluoromethyl)phenyl)-6,7-dihydro-5H-cyclopenta[c]pyridine;
(rac)-4-(4-(Trifluoromethyl)phenyl)-5,6,7,8-tetrahydroisoquinolin-8-ol;
(−)-(S)-4-(4-(Trifluoromethyl)phenyl)-5,6,7,8-tetrahydroisoquinolin-8-ol;
(+)-(R)-4-(4-(Trifluoromethyl)phenyl)-5,6,7,8-tetrahydroisoquinolin-8-ol;
(R)—N-(4-(2-Cyclopropyl-4-(trifluoromethyl)phenyl)-5,6,7,8-tetrahydroisoquinolin-8-yl)propionamide;
(+)-(7R or 7S)-4-[3-Fluoro-4-(trifluoromethyl)phenyl]-6,6-dimethyl-5,7-dihydrocyclopenta[c]-pyridin-7-ol;

(−)-(7S or 7R)-4-[3-Fluoro-4-(trifluoromethyl)phenyl]-6,6-dimethyl-5,7-dihydrocyclopenta[c]-pyridin-7-ol;
or a pharmaceutically acceptable salt thereof.

39. A compound according to claim 1, selected from
(+)-(R or S)—N-(4-(4-Cyanophenyl)-5,6,7,8-tetrahydroisoquinolin-8-yl)propionamide;
(+)-(R or S)—N-(4-(4-(Trifluoromethyl)phenyl)-5,6,7,8-tetrahydroisoquinolin-8-yl)propionamide;
(+)-(R or S)—N-(4-(2-Fluoro-4-(trifluoromethyl)phenyl)-5,6,7,8-tetrahydroisoquinolin-8-yl)propionamide;
(+)-(R or S)—N-(4-(3-Fluoro-4-(trifluoromethyl)phenyl)-5,6,7,8-tetrahydroisoquinolin-8-yl)propionamide;
(+)-(R or S)—N-(4-(4-(Trifluoromethyl)phenyl)-6,7-dihydro-5H-cyclopenta[c]pyridin-7-yl)propionamide;
(+)-(R or S)—N-(4-(2-Fluoro-4-(trifluoromethyl)phenyl)-6,7-dihydro-5H-cyclopenta[c]pyridin-7-yl)propionamide;
N-[(7S,8R or 7R,8S)-7-Methyl-4-(4-trifluoromethyl-phenyl)-5,6,7,8-tetrahydro-isoquinolin-8-yl]-propionamide;
or a pharmaceutically acceptable salt thereof.

40. A compound according to claim 1, selected from
(rac)-4-(2-Fluoro-4-(trifluoromethyl)phenyl)-6,7-dihydro-5H-cyclopenta[c]pyridin-7-ol;
(+)-(7R or 7S)-6,6-Dimethyl-4-[4-(trifluoromethyl)phenyl]-5,7-dihydrocyclopenta[c]pyridin-7-ol;
(rac)-N-(4-(3-Fluoro-4-(trifluoromethyl)phenyl)-6,7-dihydro-5H-cyclopenta[c]pyridin-7-yl)propionamide;
(rac)-N,N-Dimethyl-2-(4-(4-(trifluoromethyl)phenyl)-6,7-dihydro-5H-cyclopenta[c]pyridin-7-yloxy)acetamide;
(+)-(7R or 7S)-4-[3-Fluoro-4-(trifluoromethyl)phenyl]-6,6-dimethyl-5,7-dihydrocyclopenta[c]pyridin-7-ol;
or a pharmaceutically acceptable salt thereof.

41. A process to prepare a compound according to claim 1 comprising the reaction of a compound of formula (II) in the presence of a compound of formula (III);

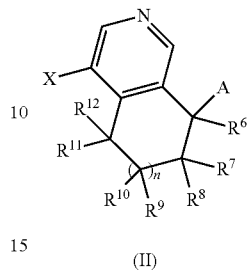

(II)

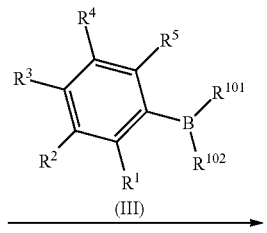

(III)

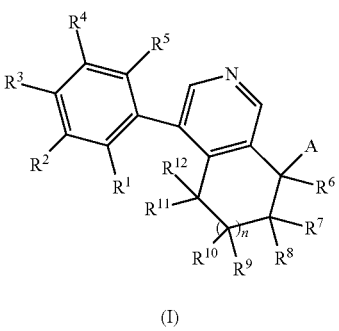

(I)

wherein $R^1, R^2, R^3, R^4, R^5, R^6, R^7, R^8, R^9, R^{10}, R^{11}, R^{12}$, A and n are as defined above, $R^{101}$ and $R^{102}$ are independently selected from alkyl and cycloalkyl, or $R^{101}$ and $R^{102}$ together with the boron atom to which they are attached form a borolane and X is halogen or triflate.

42. A pharmaceutical composition comprising a compound according to claim 1 and a therapeutically inert carrier.

* * * * *